(12) United States Patent
Heron et al.

(10) Patent No.: US 10,385,389 B2
(45) Date of Patent: Aug. 20, 2019

(54) METHOD FOR ATTACHING ONE OR MORE POLYNUCLEOTIDE BINDING PROTEINS TO A TARGET POLYNUCLEOTIDE

(71) Applicant: Oxford Nanopore Technologies Ltd., Oxford (GB)

(72) Inventors: Andrew John Heron, Oxford (GB); Clive Gavin Brown, Cambridge (GB); Rebecca Victoria Bowen, Oxford (GB); James White, Oxford (GB); Daniel John Turner, Oxford (GB); Joseph Hargreaves Lloyd, Oxford (GB); Christopher Peter Youd, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 89 days.

(21) Appl. No.: 15/113,207

(22) PCT Filed: Jan. 22, 2015

(86) PCT No.: PCT/GB2015/050140
§ 371 (c)(1),
(2) Date: Jul. 21, 2016

(87) PCT Pub. No.: WO2015/110813
PCT Pub. Date: Jul. 30, 2015

(65) Prior Publication Data
US 2017/0107569 A1    Apr. 20, 2017

Related U.S. Application Data

(63) Continuation-in-part of application No. PCT/GB2014/050175, filed on Jan. 22, 2014.

(30) Foreign Application Priority Data

Apr. 4, 2014 (GB) .................................. 1406151.9
Apr. 4, 2014 (GB) .................................. 1406155.0
Sep. 12, 2014 (GB) ................................ 1416197.0

(51) Int. Cl.
C12Q 1/68 (2018.01)
C12Q 1/6869 (2018.01)
C12N 9/00 (2006.01)
C12Q 1/6816 (2018.01)
C12Q 1/6834 (2018.01)

(52) U.S. Cl.
CPC ............ *C12Q 1/6869* (2013.01); *C12N 9/93* (2013.01); *C12Q 1/6816* (2013.01); *C12Q 1/6834* (2013.01); *C12Y 605/01001* (2013.01); *C12Q 2565/631* (2013.01)

(58) Field of Classification Search
None
See application file for complete search history.

(56) References Cited

U.S. PATENT DOCUMENTS

| | | |
|---|---|---|
| 6,426,231 B1 | 7/2002 | Bayley et al. |
| 6,627,067 B1 | 9/2003 | Branton et al. |
| 6,916,665 B2 | 7/2005 | Bayley et al. |
| 7,189,503 B2 | 3/2007 | Akeson et al. |
| 8,105,846 B2 | 1/2012 | Bayley et al. |
| 8,785,211 B2 | 7/2014 | Bayley et al. |
| 8,822,160 B2 | 9/2014 | Bayley et al. |
| 8,828,208 B2 | 9/2014 | Canas et al. |
| 10,167,503 B2 | 1/2019 | Clarke et al. |
| 2002/0094526 A1 | 7/2002 | Bayley et al. |
| 2002/0197614 A1* | 12/2002 | Weir ............... C12Q 1/6834 435/6.12 |
| 2003/0099951 A1 | 5/2003 | Akeson et al. |
| 2005/0053961 A1 | 3/2005 | Akeson et al. |
| 2006/0063171 A1 | 3/2006 | Akeson et al. |
| 2006/0105461 A1 | 5/2006 | Tom-Moy et al. |
| 2009/0298075 A1 | 12/2009 | Travers et al. |
| 2010/0120098 A1 | 5/2010 | Grunenwald et al. |
| 2010/0297638 A1 | 11/2010 | Bayley et al. |
| 2011/0177498 A1 | 7/2011 | Clarke et al. |
| 2011/0229877 A1 | 9/2011 | Jayasinghe et al. |
| 2012/0058468 A1 | 3/2012 | McKeown |
| 2012/0107802 A1 | 5/2012 | Stoddart et al. |
| 2014/0051069 A1 | 2/2014 | Jayasinghe et al. |
| 2014/0262784 A1 | 9/2014 | Clarke et al. |
| 2015/0031020 A1 | 1/2015 | Jayasinghe et al. |
| 2016/0010147 A1 | 1/2016 | Heron et al. |
| 2018/0148481 A2 | 5/2018 | Howorka et al. |
| 2018/0208632 A1 | 7/2018 | Bruce et al. |
| 2018/0334707 A1 | 11/2018 | Stoddart et al. |

(Continued)

FOREIGN PATENT DOCUMENTS

| | | |
|---|---|---|
| CA | 2381139 | 3/2001 |
| EP | 2682460 | 1/2014 |
| GB | 2453377 | 4/2009 |

(Continued)

OTHER PUBLICATIONS

Ahern, The Scientist 9 (15), 20 (1995).*
Astier et al., Stochastic detection of motor protein-RNA complexes by single-channel current recording. Chemphyschem. Oct. 22, 2007;8(15):2189-94.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

(Continued)

*Primary Examiner* — James Martinell
(74) *Attorney, Agent, or Firm* — Wolf, Greenfield & Sacks, P.C.

(57) ABSTRACT

The invention relates to new methods of attaching one or more polynucleotide binding proteins to a target polynucleotide. The invention also relates to new methods of characterizing target polynucleotides.

20 Claims, 21 Drawing Sheets
Specification includes a Sequence Listing.

(56) References Cited

U.S. PATENT DOCUMENTS

2018/0335425 A1 11/2018 Maglia et al.
2018/0364214 A1 12/2018 Maglia et al.

FOREIGN PATENT DOCUMENTS

| WO | WO 2001/059453 | 8/2001 |
|---|---|---|
| WO | WO 2006/028508 | 3/2006 |
| WO | WO 2007/057668 | 5/2007 |
| WO | WO 2008/124107 | 10/2008 |
| WO | WO 2009/044170 | 4/2009 |
| WO | WO 2009/077734 | 6/2009 |
| WO | WO 2009/143425 | 11/2009 |
| WO | WO 2010/004265 | 1/2010 |
| WO | WO 2010/086622 | 8/2010 |
| WO | WO 2012/164270 | 12/2012 |
| WO | WO 2013/014451 | 1/2013 |
| WO | WO 2013/057495 | 4/2013 |
| WO | WO 2013/098561 | 7/2013 |
| WO | WO 2013/098562 | 7/2013 |
| WO | WO 2013/153359 | 10/2013 |
| WO | WO 2014/013259 | 1/2014 |
| WO | WO 2014/013262 | 1/2014 |
| WO | WO 2014/135838 | 9/2014 |
| WO | WO 2016/055778 | 4/2016 |

OTHER PUBLICATIONS

Benner et al., Sequence-specific detection of individual DNA polymerase complexes in real time using a nanopore. Nat Nanotechnol. Nov. 2007;2(11):718-24. doi: 10.1038/nnano.2007.344. Epub Oct. 28, 2007.

Braha et al., Carriers versus adapters in stochastic sensing. Chemphyschem. May 2005;6(5):889-92.

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.

Eid et al., Real-time DNA sequencing from single polymerase molecules. Science. Jan. 2, 2009;323(5910):133-8. doi:10.1126/science.1162986. Epub Nov. 20, 2008.

Franceschini et al., DNA Translocation through Nanopores at Physiological Ionic Strengths Requires Precise Nanoscale Engineering. ACS Nano. Sep. 27, 2016;10(9):8394-402. doi: 10.1021/acsnano.6b03159. Epub Aug. 15, 2016.

Haque et al., Solid-State and Biological Nanopore for Real-Time Sensing of Single Chemical and Sequencing of DNA. Nano Today. Feb. 2013;8(1):56-74.

Hornblower et al., Single-molecule analysis of DNA-protein complexes using nanopores. Nat Methods. Apr. 2007;4(4):315-7. Epub Mar. 4, 2007.

Howorka et al., Nanopores as protein sensors. Nat Biotechnol. Jun. 7, 2012;30(6):506-7. doi: 10.1038/nbt.2264.

Huff et al., Functions of the periplasmic loop of the porin MspA from *Mycobacterium smegmatis*. J Biol Chem. Apr. 10, 2009;284(15):10223-31. doi: 10.1074/jbc.M808599200. Epub Feb. 10, 2009.

Johnston et al., Coexpression of proteins in bacteria using T7-based expression plasmids: expression of heteromeric cell-cycle and transcriptional regulatory complexes. Protein Expr Purif. Dec. 2000;20(3):435-43.

Kang et al., Single protein pores containing molecular adapters at high temperatures. Angew Chem Int Ed Engl. Feb. 25, 2005;44(10):1495-9.

Kumar et al., Peg-labeled nucleotides and nanopore detection for single molecule DNA sequencing by synthesis. Sci Rep. 2012;2:684. Epub Sep. 21, 2012.

Mitchell et al., Chemical tags facilitate the sensing of individual DNA strands with nanopores. Angew Chem Int Ed Engl. 2008;47(30):5565-8. doi:10.1002/anie.200800183.

Nakane et al., A nanosensor for transmembrane capture and identification of single nucleic Acid molecules. Biophys J. Jul. 2004;87(1):615-21. Erratum in: Biophys J. Nov. 2004;87(5):3618.

Nakane et al., Nanopore sensors for nucleic acid analysis. J. Phys.: Condens. Matter. 2003;15: R1365-R1393.

Rhee et al., Nanopore sequencing technology: research trends and applications. Trends Biotechnol. Dec. 2006;24(12):580-6. Epub Oct. 19, 2006.

Rotem et al., Protein detection by nanopores equipped with aptamers. J Am Chem Soc. Feb. 8, 2012;134(5):2781-7. doi:10.1021/ja2105653. Epub Jan. 26, 2012.

Saariaho et al., Characteristics of MuA transposase-catalyzed processing of model transposon end DNA hairpin substrates. Nucleic Acids Res. Jun. 6, 2006;34(10):3139-49.

Sanchez-Quesada et al., Cyclic Peptides as Molecular Adapters for a Pore-Forming Protein. Journal American Chemical Society, vol. 122(48):11757-11766 (2000).

Stoddart et al., Multiple base-recognition sites in a biological nanopore: two heads are better than one. Angew Chem Int Ed Engl. 2010;49(3):556-9. doi: 10.1002/anie.200905483.

Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.

Wanunu, Nanopores: A journey towards DNA sequencing. Phys Life Rev. Jun. 2012;9(2):125-58. doi:10.1016/j.plrev.2012.05.010. Epub May 18, 2012.

Wu et al., Protein nanopores with covalently attached molecular adapters. J Am Chem Soc. Dec. 26, 2007;129(51):16142-8. Epub Nov. 30, 2007.

\* cited by examiner

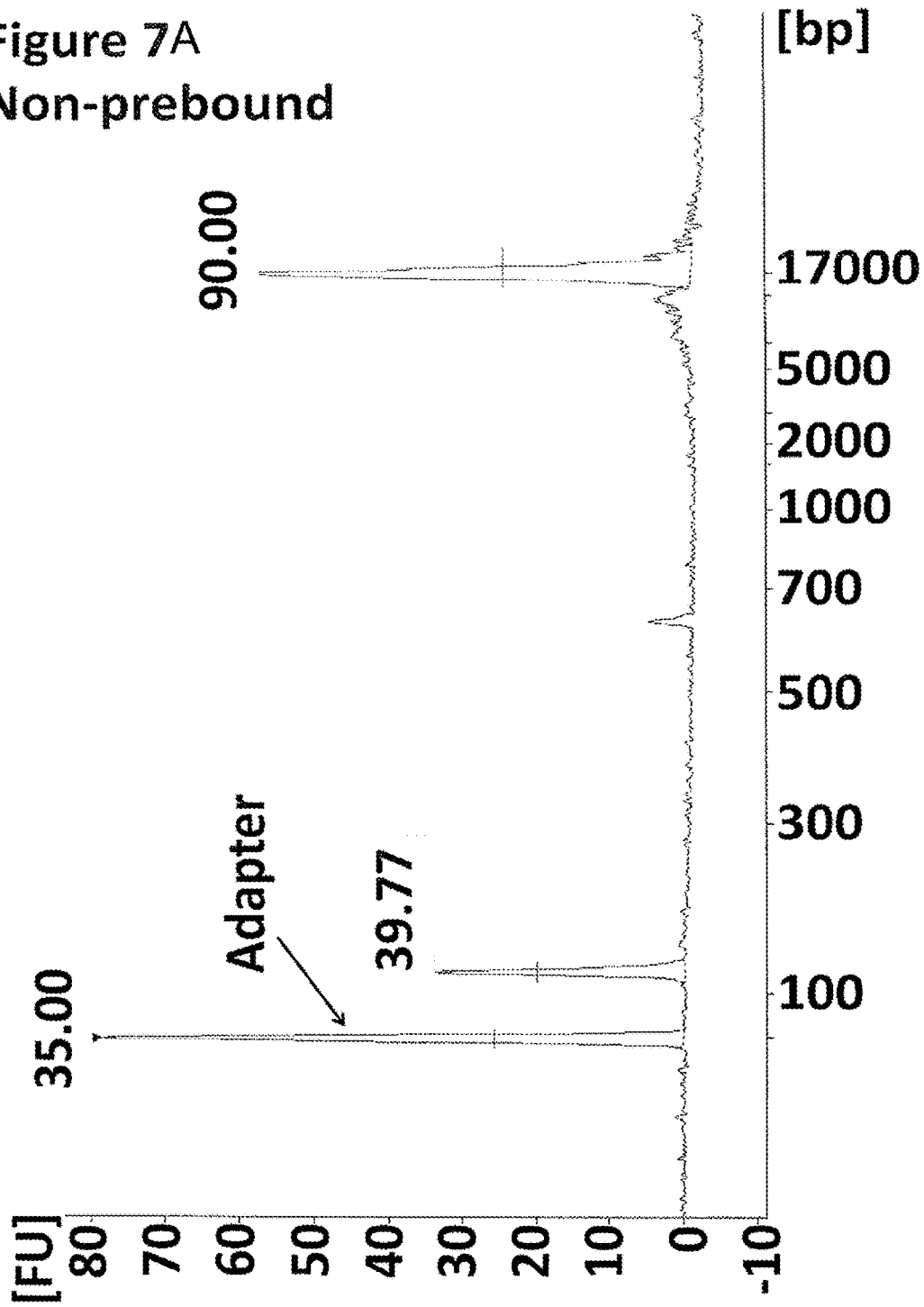

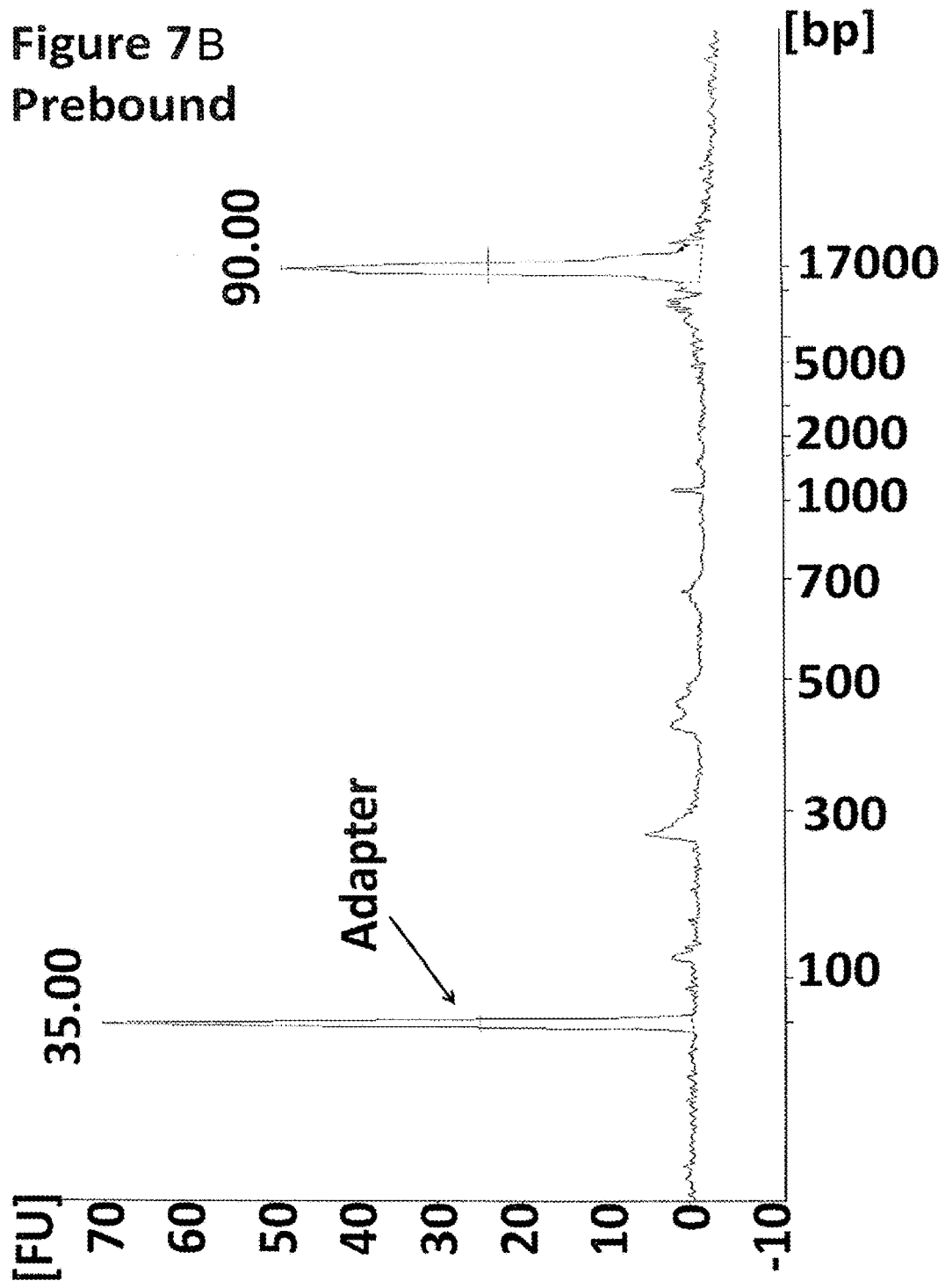

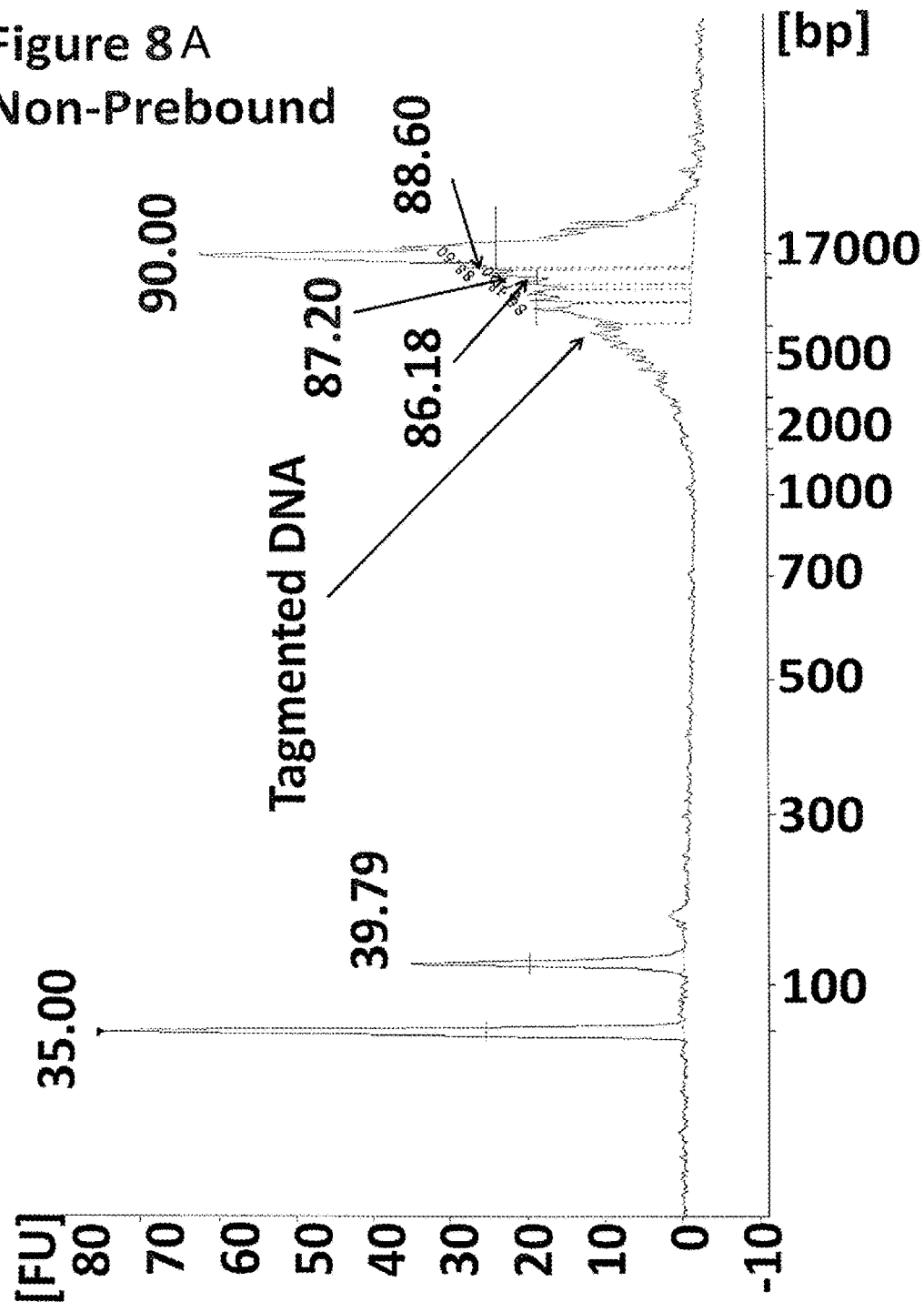

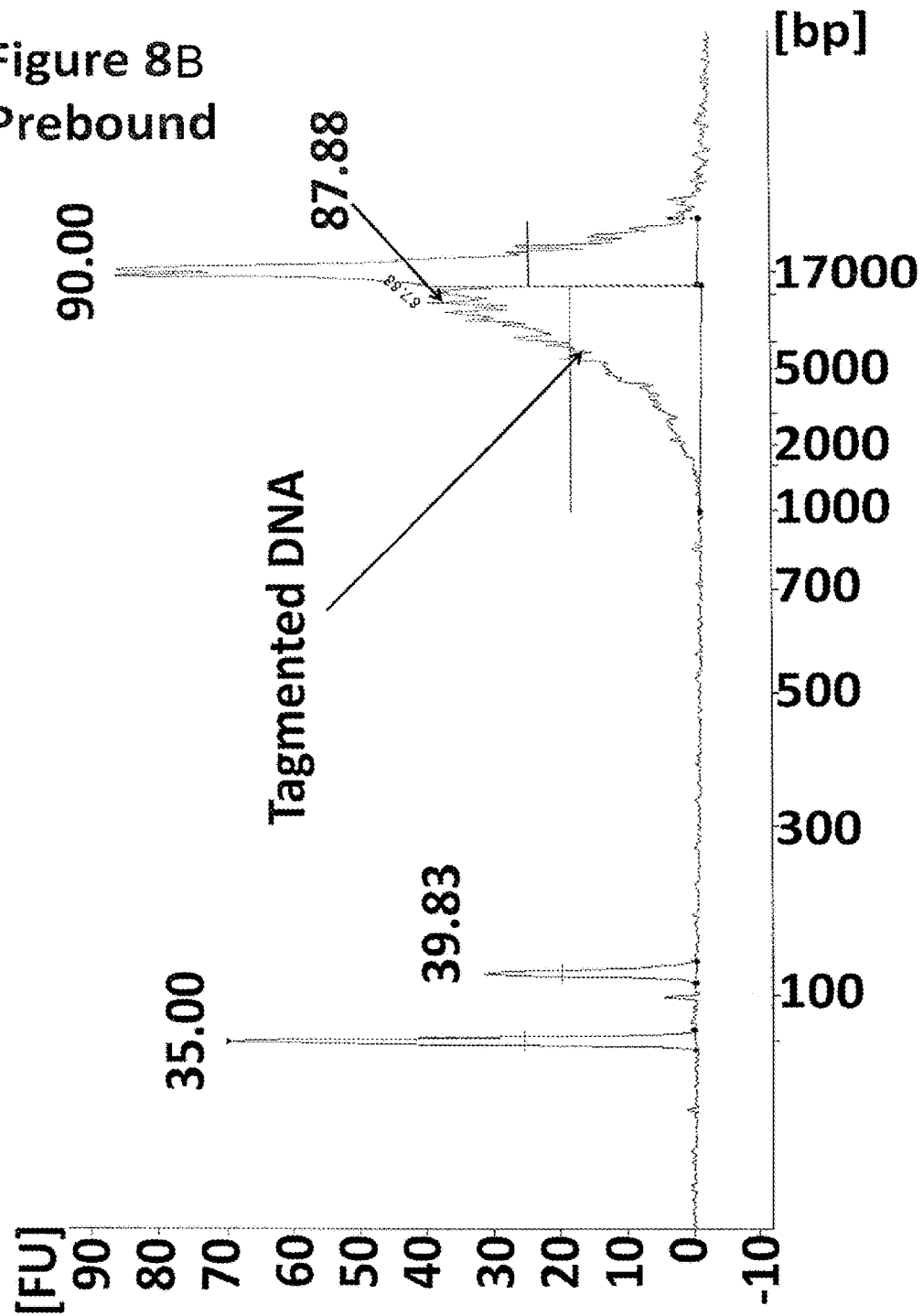

SEQUENCE LISTING

```
<160> NUMBER OF SEQ ID NOS: 47

<210> SEQ ID NO 1
<211> LENGTH: 558
<212> TYPE: DNA
<213> ORGANISM: Artificial Sequence
<220> FEATURE:
<223> OTHER INFORMATION: Mycobacterium smegmatis porin A mutant
      (D90N/D91N/D93N/D118R/D134R/E193K)

<400> SEQUENCE: 1
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccggggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                   558

<210> SEQ ID NO 2
<211> LENGTH: 184
<212> TYPE: PRT
<213> ORGANISM: Artificial Sequence
<220> FEATURE:
<223> OTHER INFORMATION: Mycobacterium smegmatis porin A mutant
      (D90N/D91N/D93N/D118R/D134R/E139K)

<400> SEQUENCE: 2

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
```

```
              115                 120                 125
Ala Thr Phe Ser Val Arg Val Ser Gly Ala Lys Gly Val Ala Val
              130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                    165                 170                 175

Tyr Gly Glu Pro Trp Asn Met Asn
                180

<210> SEQ ID NO 3
<211> LENGTH: 885
<212> TYPE: DNA
<213> ORGANISM: Artificial Sequence
<220> FEATURE:
<223> OTHER INFORMATION: alpha-hemolysin mutant (E111N/K147N)

<400> SEQUENCE: 3
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagtttta tcgatgataa aaatcacaat aaaaaactgc tagttattag aacaaaaggt     180
accattgctg gtcaatatag agtttatagc gaagaaggtg ctaacaaaag tggtttagcc     240
tggccttcag cctttaaggt acagttgcaa ctacctgata tgaagtagc tcaaatatct     300 gattactatc caagaaattc gattgataca aaaaactata tgagtacttt aacttatgga     360
ttcaacggta atgttactgg tgatgataca ggaaaaattg gcggccttat tggtgcaaat     420
gtttcgattg gtcatacact gaactatgtt caacctgatt tcaaaacaat tttagagagc     480
ccaactgata aaaagtagg ctggaaagtg atatttaaca atatggtgaa tcaaaattgg     540
ggaccatacg atcgagattc ttggaacccg gtatatggca atcaactttt catgaaaact     600
agaaatggtt ctatgaaagc agcagataac ttccttgatc ctaacaaagc aagttctcta     660
ttatcttcag ggttttcacc agacttcgct acagttatta ctatggatag aaaagcatcc     720
aaacaacaaa caaatataga gtaatatac gaacagttc gtgatgatta ccaattgcat     780
tggacttcaa caaattggaa aggtaccaat actaaagata atggacaga tcgttcttca     840 gaaagatata aaatcgattg ggaaaaagaa gaaatgacaa attaa                     885

<210> SEQ ID NO 4
<211> LENGTH: 293
<212> TYPE: PRT
<213> ORGANISM: Artificial Sequence
<220> FEATURE:
<223> OTHER INFORMATION: alpha-hemolysin mutant (E111N/K147N)

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80
```

```
Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 5
<211> LENGTH: 184
<212> TYPE: PRT
<213> ORGANISM: Mycobacterium smegmatis

<400> SEQUENCE: 5

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
            35                  40                  45

Ile Val Ala Gly Pro Gly Ala Asp Glu Phe Glu Gly Thr Leu Glu Leu
        50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160
```

```
Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 6
<211> LENGTH: 184
<212> TYPE: PRT
<213> ORGANISM: Mycobacterium smegmatis

<400> SEQUENCE: 6

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

Arg Asn Arg Leu Thr Arg Glu Trp Phe His Ser Gly Arg Ala Lys Tyr
            35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65              70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 7
<211> LENGTH: 183
<212> TYPE: PRT
<213> ORGANISM: Mycobacterium smegmatis

<400> SEQUENCE: 7

```
Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
                20                  25                  30

Asn Arg Leu Thr Arg Glu Trp Phe His Ser Gly Arg Ala Thr Tyr His
            35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65              70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110
```

Ser Ile Ser Ala Asp Leu Gly Asn Gly Pro Gly Ile Gln Glu Val Ala
    115                 120                 125

Thr Phe Ser Val Asp Val Lys Gly Ala Lys Gly Ala Val Ala Val Ser
130                 135                 140

Asn Ala His Gly Thr Val Thr Gly Ala Ala Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180

<210> SEQ ID NO 8
<211> LENGTH: 1830
<212> TYPE: DNA
<213> ORGANISM: Bacillus subtilis phage phi29

<400> SEQUENCE: 8

| | |
|---|---|
| atgaaacaca tgccgcgtaa aatgtatagc tgcgcgtttg aaaccacgac caaagtggaa | 60 |
| gattgtcgcg tttgggccta tggctacatg aacatcgaag atcattctga atacaaaatc | 120 |
| ggtaacagtc tggatgaatt tatggcatgg gtgctgaaaa ttcaggcgga tctgtacttc | 180 |
| cacaacctga atttgatgg cgcattcatt atcaactggc tggaacgtaa tggctttaaa | 240 |
| tggagcgcga tggtctgcc gaacacgtat aataccatta tctctcgtat gggccagtgg | 300 |
| tatatgattg atatctgcct gggctacaaa ggtaaacgca aaattcatac cgtgatctat | 360 |
| gatagcctga aaaactgcc gtttccggtg aagaaaattg cgaaagattt caaactgacg | 420 |
| gttctgaaag cgatattga ttatcacaaa gaacgtccgg ttggttacaa aatcaccccg | 480 |
| gaagaatacg catacatcaa aaacgatatc cagatcatcg cagaagcgct gctgattcag | 540 |
| tttaaacagg gcctggatcg catgaccgcg ggcagtgata gcctgaaagg tttcaaagat | 600 |
| atcatcacga ccaaaaaatt caaaaaagtg ttcccgacgc tgagcctggg tctggataaa | 660 |
| gaagttcgtt atgcctaccg cggcggtttt acctggctga cgatcgtttt caaagaaaaa | 720 |
| gaaattggcg agggtatggt gtttgatgtt aatagtctgt atccggcaca gatgtacagc | 780 |
| cgcctgctgc cgtatggcga accgatcgtg ttcgagggta aatatgtttg ggatgaagat | 840 |
| tacccgctgc atattcagca catccgttgt gaatttgaac tgaaagaagg ctatattccg | 900 |
| accattcaga tcaaacgtag tcgcttctat aagggtaacg aatacctgaa aagctctggc | 960 |
| ggtgaaatcg cggatctgtg gctgagtaac gtggatctgg aactgatgaa agaacactac | 1020 |
| gatctgtaca cgttgaata catcagcggc ctgaaattta agccacgac cggtctgttc | 1080 |
| aaagatttca tcgataaatg gacctacatc aaaacgacct ctgaaggcgc gattaaacag | 1140 |
| ctggccaaac tgatgctgaa cagcctgtat ggcaaattcg cctctaatcc ggatgtgacc | 1200 |
| ggtaaagttc cgtacctgaa agaaaatggc gcactgggtt ttcgcctggg cgaagaagaa | 1260 |
| acgaaagatc cggtgtatac cccgatgggt gttttcatta cggcctgggc acgttacacg | 1320 |
| accatcaccg cggcccaggc atgctatgat cgcattatct actgtgatac cgattctatt | 1380 |
| catctgacgg gcaccgaaat cccggatgtg attaaagata tcgttgatcc gaaaaaactg | 1440 |
| ggttattggg cccacgaaag tacgtttaaa cgtgcaaaat acctgcgcca gaaaacctac | 1500 |
| atccaggata tctacatgaa agaagtggat ggcaaactgg ttgaaggttc tccggatgat | 1560 |
| tacaccgata tcaaattcag tgtgaaatgc gccggcatga cggataaaat caaaaaagaa | 1620 |
| gtgacccttcg aaaacttcaa agttggtttc agccgcaaaa tgaaaccgaa accggtgcag | 1680 |

```
gttccgggcg gtgtggttct ggtggatgat acgtttacca ttaaatctgg cggtagtgcg   1740
tggagccatc cgcagttcga aaaggcggt ggctctggtg gcggttctgg cggtagtgcc   1800
tggagccacc cgcagtttga aaataataa                                    1830
```

<210> SEQ ID NO 9
<211> LENGTH: 608
<212> TYPE: PRT
<213> ORGANISM: Bacillus subtilis phage phi29

<400> SEQUENCE: 9

```
Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
```

Phe Lys Ala Thr Thr Gly Leu Phe Lys Asp Phe Ile Asp Lys Trp Thr
            355                 360                 365
Tyr Ile Lys Thr Thr Ser Glu Gly Ala Ile Lys Gln Leu Ala Lys Leu
    370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
            420                 425                 430
Ile Thr Ala Trp Ala Arg Tyr Thr Thr Ile Thr Ala Ala Gln Ala Cys
            435                 440                 445
Tyr Asp Arg Ile Ile Tyr Cys Asp Thr Asp Ser Ile His Leu Thr Gly
    450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Gln Lys Thr Tyr Ile Gln Asp Ile Tyr Met Lys Glu Val Asp Gly Lys
            500                 505                 510
Leu Val Glu Gly Ser Pro Asp Asp Tyr Thr Asp Ile Lys Phe Ser Val
            515                 520                 525
Lys Cys Ala Gly Met Thr Asp Lys Ile Lys Lys Glu Val Thr Phe Glu
    530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys Ser
                565                 570                 575
Gly Gly Ser Ala Trp Ser His Pro Gln Phe Glu Lys Gly Gly Ser
            580                 585                 590
Gly Gly Gly Ser Gly Gly Ser Ala Trp Ser His Pro Gln Phe Glu Lys
        595                 600                 605

<210> SEQ ID NO 10
<211> LENGTH: 1390
<212> TYPE: DNA
<213> ORGANISM: Escherichia coli

<400> SEQUENCE: 10
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg cgaaccgga agtgttttat tgcaaaccgg ccgatgatta tctgccgcag     180
ccgggtgcgg tgctgattac cggtattacc ccgcaggaag cgcgcgcgaa aggtgaaaac     240
gaagcggcgt tgccgcgcg cattcatagc ctgtttaccg tgccgaaaac ctgcattctg     300
ggctataaca atgtgcgctt cgatgatgaa gttacccgta atatctttta cgtaactttt     360
tatgatccgt atgcgtggag ctggcagcat gataacagcc gttgggatct gctggatgtg     420
atgcgcgcgt gctatgcgct cgccccggaa ggcattaatt ggccggaaaa cgatgatggc     480
ctgccgagct ttcgtctgga acatctgacc aaagccaacg gcattgaaca tagcaatgcc     540
catgatgcga tggccgatgt ttatgcgacc attgcgatgg cgaaactggt taaaccccgt     600
cagccgcgcc tgtttgatta tctgtttacc accgtaaca aacacaaact gatggcgctg     660

```
attgatgttc cgcagatgaa accgctggtg catgtgagcg gcatgtttgg cgcctggcgc    720
ggcaacacca gctgggtggc cccgctggcc tggcacccgg aaaatcgtaa cgccgtgatt    780
atggttgatc tggccggtga tattagcccg ctgctggaac tggatagcga taccctgcgt    840
gaacgcctgt ataccgccaa aaccgatctg gcgataatg ccgccgtgcc ggtgaaactg     900
gttcacatta caaatgccc ggtgctggcc caggcgaaca ccctgcgccc ggaagatgcg     960
gatcgtctgg gtattaatcg ccagcattgt ctggataatc tgaaaatcct gcgtgaaaac   1020
ccgcaggtgc gtgaaaaagt ggtggcgatc ttcgcggaag cggaaccgtt caccccgagc   1080
gataacgtgg atgcgcagct gtataacggc ttctttagcg atgccgatcg cgcggcgatg   1140
aaaatcgttc tggaaaccga accgcgcaat ctgccggcgc tggatattac ctttgttgat   1200
aaacgtattg aaaaactgct gtttaattat cgtgcgcgca attttccggg taccctggat   1260
tatgccgaac agcagcgttg gctggaacat cgtcgtcagg ttttcacccc ggaatttctg   1320
cagggttatg cggatgaact gcagatgctg gttcagcagt atgccgatga taaagaaaaa   1380
gtggcgctgc                                                          1390
```

<210> SEQ ID NO 11
<211> LENGTH: 485
<212> TYPE: PRT
<213> ORGANISM: Escherichia coli

<400> SEQUENCE: 11

Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
            245                 250                 255

Asn Ala Val Ile Met Val Asp Leu Ala Gly Asp Ile Ser Pro Leu Leu
        260                 265                 270

Glu Leu Asp Ser Asp Thr Leu Arg Glu Arg Leu Tyr Thr Ala Lys Thr
    275                 280                 285

Asp Leu Gly Asp Asn Ala Ala Val Pro Val Lys Leu Val His Ile Asn
290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
            325                 330                 335

Leu Arg Glu Asn Pro Gln Val Arg Glu Lys Val Val Ala Ile Phe Ala
        340                 345                 350

Glu Ala Glu Pro Phe Thr Pro Ser Asp Asn Val Asp Ala Gln Leu Tyr
    355                 360                 365

Asn Gly Phe Phe Ser Asp Ala Asp Arg Ala Ala Met Lys Ile Val Leu
370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
            405                 410                 415

Gly Thr Leu Asp Tyr Ala Glu Gln Gln Arg Trp Leu Glu His Arg Arg
        420                 425                 430

Gln Val Phe Thr Pro Glu Phe Leu Gln Gly Tyr Ala Asp Glu Leu Gln
    435                 440                 445

Met Leu Val Gln Gln Tyr Ala Asp Asp Lys Lys Val Ala Leu Leu
450                 455                 460

Lys Ala Leu Trp Gln Tyr Ala Glu Glu Ile Val Ser Gly Ser Gly His
465                 470                 475                 480

His His His His
        485

<210> SEQ ID NO 12
<211> LENGTH: 804
<212> TYPE: DNA
<213> ORGANISM: Escherichia coli

<400> SEQUENCE: 12
atgaaatttg tctcttttaa tatcaacggc ctgcgcgcca gacctcacca gcttgaagcc        60
atcgtcgaaa agcaccaacc ggatgtgatt ggcctgcagg agacaaaagt tcatgacgat       120
atgtttccgc tcgaagaggt ggcgaagctc ggctacaacg tgttttatca cgggcagaaa       180
ggccattatg gcgtggcgct gctgaccaaa gagacgccga ttgccgtgcg tcgcggcttt       240
cccggtgacg acgaagaggc gcagcggcgg attattatgg cggaaatccc ctcactgctg       300
ggtaatgtca ccgtgatcaa cggttacttc ccgcagggtg aaagccgcga ccatccgata       360
aaattcccgg caaaagcgca gttttatcag aatctgcaaa actacctgga aaccgaactc       420
aaacgtgata tccggtact gattatgggc gatatgaata tcagccctac agatctggat       480
atcggcattg gcgaagaaaa ccgtaagcgc tggctgcgta ccggtaaatg ctctttcctg       540
ccggaagagc gcgaatggat ggacaggctg atgagctggg ggttggtcga taccttccgc       600
catgcgaatc cgcaaacagc agatcgtttc tcatggtttg attaccgctc aaaaggtttt       660

```
gacgataacc gtggtctgcg catcgacctg ctgctcgcca gccaaccgct ggcagaatgt    720
tgcgtagaaa ccggcatcga ctatgaaatc cgcagcatgg aaaaaccgtc cgatcacgcc    780
cccgtctggg cgaccttccg ccgc                                            804
```

<210> SEQ ID NO 13
<211> LENGTH: 268
<212> TYPE: PRT
<213> ORGANISM: Escherichia coli

<400> SEQUENCE: 13

```
Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265
```

<210> SEQ ID NO 14
<211> LENGTH: 1275
<212> TYPE: DNA
<213> ORGANISM: Thermus thermophilus

<400> SEQUENCE: 14

```
atgtttcgtc gtaaagaaga tctggatccg ccgctggcac tgctgccgct gaaaggcctg    60
cgcgaagccg ccgcactgct ggaagaagcg ctgcgtcaag gtaaacgcat tcgtgttcac   120
ggcgactatg atgcggatgg cctgaccggc accgcgatcc tggttcgtgg tctggccgcc   180
```

```
ctgggtgcgg atgttcatcc gtttatcccg caccgcctgg aagaaggcta tggtgtcctg      240
atggaacgcg tcccggaaca tctggaagcc tcggacctgt ttctgaccgt tgactgcggc      300
attaccaacc atgcggaact gcgcgaactg ctggaaaatg gcgtggaagt cattgttacc      360
gatcatcata cgccgggcaa aacgccgccg cgggtctggt cgtgcatcc ggcgctgacg       420 ccggatctga agaaaaaacc gaccggcgca ggcgtggcgt ttctgctgct gtgggcactg      480
catgaacgcc tgggcctgcc gccgccgctg gaatacgcgg acctggcagc cgttggcacc      540
attgccgacg ttgccccgct gtggggttgg aatcgtgcac tggtgaaaga aggtctggca      600
cgcatcccgg cttcatcttg ggtgggcctg cgtctgctgg ctgaagccgt gggctatacc      660
ggcaaagcgg tcgaagtcgc tttccgcatc gcgccgcgca tcaatgcggc ttcccgcctg      720
ggcgaagcgg aaaaagccct gcgcctgctg ctgacggatg atgcggcaga agctcaggcg      780
ctggtcggcg aactgcaccg tctgaacgcc cgtcgtcaga ccctggaaga agcgatgctg      840
cgcaaactgc tgccgcaggc cgaccccgaa gcgaaagcca tcgttctgct ggacccggaa      900
ggccatccgg tgttatggg tattgtggcc tctcgcatcc tggaagcgac cctgcgcccg      960
gtctttctgg tggcccaggg caaaggcacc gtgcgttcgc tggctccgat tccgccgtc    1020 gaagcactgc gcagcgcgga agatctgctg ctgcgttatg gtggtcataa agaagcggcg    1080
ggtttcgcaa tggatgaagc gctgtttccg gcgttcaaag cacgcgttga agcgtatgcc    1140 gcacgttttcc cggatccggt tcgtgaagtg gcactgctgg atctgctgcc ggaaccgggc    1200
ctgctgccgc aggtgttccg tgaactggca ctgctggaac cgtatggtga aggtaacccg    1260
gaaccgctgt cctg                                                      1275
```

<210> SEQ ID NO 15
<211> LENGTH: 425
<212> TYPE: PRT
<213> ORGANISM: Thermus thermophilus

<400> SEQUENCE: 15

```
Met Phe Arg Arg Lys Glu Asp Leu Asp Pro Pro Leu Ala Leu Leu Pro
1               5                   10                  15

Leu Lys Gly Leu Arg Glu Ala Ala Ala Leu Leu Glu Glu Ala Leu Arg
            20                  25                  30

Gln Gly Lys Arg Ile Arg Val His Gly Asp Tyr Asp Ala Asp Gly Leu
        35                  40                  45

Thr Gly Thr Ala Ile Leu Val Arg Gly Leu Ala Ala Leu Gly Ala Asp
    50                  55                  60

Val His Pro Phe Ile Pro His Arg Leu Glu Glu Gly Tyr Gly Val Leu
65                  70                  75                  80

Met Glu Arg Val Pro Glu His Leu Glu Ala Ser Asp Leu Phe Leu Thr
                85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
    130                 135                 140

Glu Lys Pro Thr Gly Ala Gly Val Ala Phe Leu Leu Leu Trp Ala Leu
145                 150                 155                 160

His Glu Arg Leu Gly Leu Pro Pro Pro Leu Glu Tyr Ala Asp Leu Ala
                165                 170                 175
```

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
        195                 200                 205

Gly Leu Arg Leu Leu Ala Glu Ala Val Gly Tyr Thr Gly Lys Ala Val
    210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
        275                 280                 285

Pro Glu Ala Lys Ala Ile Val Leu Asp Pro Glu Gly His Pro Gly
    290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
            340                 345                 350

Tyr Gly Gly His Lys Glu Ala Ala Gly Phe Ala Met Asp Glu Ala Leu
        355                 360                 365

Phe Pro Ala Phe Lys Ala Arg Val Glu Ala Tyr Ala Ala Arg Phe Pro
    370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
            420                 425

<210> SEQ ID NO 16
<211> LENGTH: 738
<212> TYPE: DNA
<213> ORGANISM: Bacteriophage lambda

<400> SEQUENCE: 16
tccggaagcg gctctggtag tggttctggc atgacaccgg acattatcct gcagcgtacc         60
gggatcgatg tgagagctgt cgaacagggg gatgatgcgt ggcacaaatt acggctcggc        120
gtcatcaccg cttcagaagt tcacaacgtg atagcaaaac cccgctccgg aaagaagtgg        180
cctgacatga aaatgtccta cttccacacc ctgcttgctg aggtttgcac cggtgtggct        240
ccggaagtta acgctaaagc actggcctgg gaaaaacagt acgagaacga cgccagaacc        300
ctgtttgaat tcacttccgg cgtgaatgtt actgaatccc cgatcatcta cgcgacgaa         360 agtatgcgta ccgcctgctc tcccgatggt ttatgcagtg acggcaacgg ccttgaactg        420
aaatgcccgt ttacctcccg ggatttcatg aagttccggc tcgtgggttt cgaggccata        480
aagtcagctt acatggccca ggtgcagtac agcatgtggg tgacgcgaaa aaatgcctgg        540
tactttgcca actatgaccc gcgtatgaag cgtgaaggcc tgcattatgt cgtgattgag        600
cgggatgaaa agtacatggc gagttttgac gagatcgtgc cggagttcat cgaaaaaatg        660
gacgaggcac tggctgaaat tggttttgta tttggggagc aatggcgatc tggctctggt        720
tccggcagcg gttccgga 738

<210> SEQ ID NO 17
<211> LENGTH: 226
<212> TYPE: PRT
<213> ORGANISM: Bacteriophage lambda

<400> SEQUENCE: 17

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225

<210> SEQ ID NO 18
<211> LENGTH: 760
<212> TYPE: PRT
<213> ORGANISM: Methanococcoides burtonii

<400> SEQUENCE: 18

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

```
Ser Glu Lys Phe Glu Arg Phe Lys Glu Leu Ala Pro Phe Gly Ile Lys
             85                  90                  95
Val Gly Ile Ser Thr Gly Asp Leu Asp Ser Arg Ala Asp Trp Leu Gly
            100                 105                 110
Val Asn Asp Ile Ile Val Ala Thr Ser Glu Lys Thr Asp Ser Leu Leu
            115                 120                 125
Arg Asn Gly Thr Ser Trp Met Asp Glu Ile Thr Thr Val Val Val Asp
    130                 135                 140
Glu Ile His Leu Leu Asp Ser Lys Asn Arg Gly Pro Thr Leu Glu Val
145                 150                 155                 160
Thr Ile Thr Lys Leu Met Arg Leu Asn Pro Asp Val Gln Val Val Ala
                165                 170                 175
Leu Ser Ala Thr Val Gly Asn Ala Arg Glu Met Ala Asp Trp Leu Gly
            180                 185                 190
Ala Ala Leu Val Leu Ser Glu Trp Arg Pro Thr Asp Leu His Glu Gly
            195                 200                 205
Val Leu Phe Gly Asp Ala Ile Asn Phe Pro Gly Ser Gln Lys Lys Ile
            210                 215                 220
Asp Arg Leu Glu Lys Asp Asp Ala Val Asn Leu Val Leu Asp Thr Ile
225                 230                 235                 240
Lys Ala Glu Gly Gln Cys Leu Val Phe Glu Ser Ser Arg Arg Asn Cys
                245                 250                 255
Ala Gly Phe Ala Lys Thr Ala Ser Ser Lys Val Ala Lys Ile Leu Asp
            260                 265                 270
Asn Asp Ile Met Ile Lys Leu Ala Gly Ile Ala Glu Glu Val Glu Ser
            275                 280                 285
Thr Gly Glu Thr Asp Thr Ala Ile Val Leu Ala Asn Cys Ile Arg Lys
            290                 295                 300
Gly Val Ala Phe His His Ala Gly Leu Asn Ser His Arg Lys Leu
305                 310                 315                 320
Val Glu Asn Gly Phe Arg Gln Asn Leu Ile Lys Val Ile Ser Ser Thr
                325                 330                 335
Pro Thr Leu Ala Ala Gly Leu Asn Leu Pro Ala Arg Arg Val Ile Ile
            340                 345                 350
Arg Ser Tyr Arg Arg Phe Asp Ser Asn Phe Gly Met Gln Pro Ile Pro
            355                 360                 365
Val Leu Glu Tyr Lys Gln Met Ala Gly Arg Ala Gly Arg Pro His Leu
            370                 375                 380
Asp Pro Tyr Gly Glu Ser Val Leu Leu Ala Lys Thr Tyr Asp Glu Phe
385                 390                 395                 400
Ala Gln Leu Met Glu Asn Tyr Val Glu Ala Asp Ala Glu Asp Ile Trp
                405                 410                 415
Ser Lys Leu Gly Thr Glu Asn Ala Leu Arg Thr His Val Leu Ser Thr
            420                 425                 430
Ile Val Asn Gly Phe Ala Ser Thr Arg Gln Glu Leu Phe Asp Phe Phe
            435                 440                 445
Gly Ala Thr Phe Phe Ala Tyr Gln Gln Asp Lys Trp Met Leu Glu Glu
            450                 455                 460
Val Ile Asn Asp Cys Leu Glu Phe Leu Ile Asp Lys Ala Met Val Ser
465                 470                 475                 480
Glu Thr Glu Asp Ile Glu Asp Ala Ser Lys Leu Phe Leu Arg Gly Thr
                485                 490                 495
Arg Leu Gly Ser Leu Val Ser Met Leu Tyr Ile Asp Pro Leu Ser Gly
```

```
                    500                 505                 510
Ser Lys Ile Val Asp Gly Phe Lys Asp Ile Gly Lys Ser Thr Gly Gly
            515                 520                 525

Asn Met Gly Ser Leu Glu Asp Lys Gly Asp Ile Thr Val Thr
        530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
            580                 585                 590

Asp Tyr Glu Trp Phe Met Gly Glu Val Lys Thr Ala Met Leu Leu Glu
        595                 600                 605

Glu Trp Val Thr Glu Val Ser Ala Glu Asp Ile Thr Arg His Phe Asn
        610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
            660                 665                 670

Asp Leu Met Glu Leu Val Gly Ile Arg Gly Val Gly Arg Val Arg Ala
        675                 680                 685

Arg Lys Leu Tyr Asn Ala Gly Phe Val Ser Val Ala Lys Leu Lys Gly
690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
        755                 760

<210> SEQ ID NO 19
<211> LENGTH: 707
<212> TYPE: PRT
<213> ORGANISM: Cenarchaeum symbiosum

<400> SEQUENCE: 19

Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30

Lys Ala Gly Leu Thr Asp Gly Lys Ser Val Leu Val Ser Ala Pro Thr
        35                  40                  45

Ala Ser Gly Lys Thr Leu Ile Ala Ala Ile Ala Met Ile Ser His Leu
    50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Gly Ile Pro Leu
                85                  90                  95

Gly Arg Pro Val Arg Val Gly Val Ser Thr Gly Asp Phe Glu Lys Ala
            100                 105                 110
```

```
Gly Arg Ser Leu Gly Asn Asn Asp Ile Leu Val Leu Thr Asn Glu Arg
            115                 120                 125

Met Asp Ser Leu Ile Arg Arg Pro Asp Trp Met Asp Glu Val Gly
130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
                180                 185                 190

Ala Gly Trp Leu Asp Cys Thr Leu Val His Ser Thr Trp Arg Pro Val
        195                 200                 205

Pro Leu Ser Glu Gly Val Tyr Gln Asp Gly Glu Val Ala Met Gly Asp
        210                 215                 220

Gly Ser Arg His Glu Val Ala Ala Thr Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
                260                 265                 270

Ile Pro Glu Ala Lys Gly Ala Asp Ala Ala Lys Leu Ala Ala Ala Ala
                275                 280                 285

Lys Lys Ile Ile Ser Ser Gly Gly Glu Thr Lys Leu Ala Lys Thr Leu
        290                 295                 300

Ala Glu Leu Val Glu Lys Gly Ala Ala Phe His His Ala Gly Leu Asn
305                 310                 315                 320

Gln Asp Cys Arg Ser Val Val Glu Glu Phe Arg Ser Gly Arg Ile
                325                 330                 335

Arg Leu Leu Ala Ser Thr Pro Thr Leu Ala Ala Gly Val Asn Leu Pro
                340                 345                 350

Ala Arg Arg Val Val Ile Ser Ser Val Met Arg Tyr Asn Ser Ser Ser
                355                 360                 365

Gly Met Ser Glu Pro Ile Ser Ile Leu Glu Tyr Lys Gln Leu Cys Gly
370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Gly Glu
                405                 410                 415

Pro Glu Pro Ile Arg Ser Ala Met Val Asp Asp Arg Ala Leu Arg Ile
                420                 425                 430

His Val Leu Ser Leu Val Thr Thr Ser Pro Gly Ile Lys Glu Asp Asp
                435                 440                 445

Val Thr Glu Phe Phe Leu Gly Thr Leu Gly Gly Gln Gln Ser Gly Glu
        450                 455                 460

Ser Thr Val Lys Phe Ser Val Ala Val Ala Leu Arg Phe Leu Gln Glu
465                 470                 475                 480

Glu Gly Met Leu Gly Arg Arg Gly Gly Arg Leu Ala Ala Thr Lys Met
                485                 490                 495

Gly Arg Leu Val Ser Arg Leu Tyr Met Asp Pro Met Thr Ala Val Thr
                500                 505                 510

Leu Arg Asp Ala Val Gly Glu Ala Ser Pro Gly Arg Met His Thr Leu
                515                 520                 525

Gly Phe Leu His Leu Val Ser Glu Cys Ser Glu Phe Met Pro Arg Phe
```

```
              530                 535                 540
Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575

Gly Leu Leu Ala Leu His Arg Trp Ile Gly Glu Ser Pro Glu Ala Lys
                580                 585                 590

Leu Ala Glu Asp Leu Lys Phe Glu Ser Gly Asp Val His Arg Met Val
                595                 600                 605

Glu Ser Ser Gly Trp Leu Leu Arg Cys Ile Trp Glu Ile Ser Lys His
                610                 615                 620

Gln Glu Arg Pro Asp Leu Leu Gly Glu Leu Asp Val Leu Arg Ser Arg
625                 630                 635                 640

Val Ala Tyr Gly Ile Lys Ala Glu Leu Val Pro Leu Val Ser Ile Lys
                645                 650                 655

Gly Ile Gly Arg Val Arg Ser Arg Arg Leu Phe Arg Gly Gly Ile Lys
                660                 665                 670

Gly Pro Gly Asp Leu Ala Ala Val Pro Val Glu Arg Leu Ser Arg Val
                675                 680                 685

Glu Gly Ile Gly Ala Thr Leu Ala Asn Asn Ile Lys Ser Gln Leu Arg
                690                 695                 700

Lys Gly Gly
705

<210> SEQ ID NO 20
<211> LENGTH: 720
<212> TYPE: PRT
<213> ORGANISM: Thermococcus gammatolerans

<400> SEQUENCE: 20

Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
                20                  25                  30

Lys Ser Gly Ala Leu Glu Gly Arg Asn Leu Val Leu Ala Ile Pro Thr
            35                  40                  45

Ala Ser Gly Lys Thr Leu Val Ser Glu Ile Val Met Val Asn Lys Leu
50                  55                  60

Ile Gln Glu Gly Gly Lys Ala Val Tyr Leu Val Pro Leu Lys Ala Leu
65                  70                  75                  80

Ala Glu Glu Lys Tyr Arg Glu Phe Lys Glu Trp Glu Lys Leu Gly Leu
                85                  90                  95

Lys Val Ala Ala Thr Thr Gly Asp Tyr Asp Ser Thr Asp Asp Trp Leu
                100                 105                 110

Gly Arg Tyr Asp Ile Ile Val Ala Thr Ala Glu Lys Phe Asp Ser Leu
                115                 120                 125

Leu Arg His Gly Ala Arg Trp Ile Asn Asp Val Lys Leu Val Val Ala
                130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
                180                 185                 190
```

```
Leu Val Val Ser Asp Trp Arg Pro Val Gln Leu Arg Gly Val Phe
            195                 200                 205

His Leu Gly Thr Leu Ile Trp Glu Asp Gly Lys Val Glu Ser Tyr Pro
    210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Ile Arg Asp Thr Lys Arg Tyr Ala Gly
                340                 345                 350

Phe Gly Trp Thr Asp Ile Pro Val Leu Glu Ile Gln Gln Met Met Gly
            355                 360                 365

Arg Ala Gly Arg Pro Arg Tyr Asp Lys Tyr Gly Glu Ala Ile Ile Val
        370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                405                 410                 415

Ser Gln Val Leu Ala Leu Ile Thr Asn Phe Gly Ile Arg Ser Phe Pro
            420                 425                 430

Glu Leu Val Arg Phe Leu Glu Arg Thr Phe Tyr Ala His Gln Arg Lys
        435                 440                 445

Asp Leu Ser Ser Leu Glu Tyr Lys Ala Lys Glu Val Val Tyr Phe Leu
450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
            500                 505                 510

Pro Phe Gly Ile Phe Gln Leu Ile Ala Ser Thr Pro Asp Met Ala Thr
        515                 520                 525

Leu Thr Ala Arg Arg Arg Glu Met Glu Asp Tyr Leu Asp Leu Ala Tyr
530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
            580                 585                 590

Ile Asp Pro Gly Asp Leu Tyr Arg Leu Leu Glu Leu Ala Asp Trp Leu
        595                 600                 605

Met Tyr Ser Leu Ile Glu Leu Tyr Lys Leu Phe Glu Pro Lys Glu Glu
```

```
                  610                 615                 620
Ile Leu Asn Tyr Leu Arg Asp Leu His Leu Arg Leu Arg His Gly Val
625                 630                 635                 640

Arg Glu Glu Leu Leu Glu Leu Val Arg Leu Pro Asn Ile Gly Arg Lys
                  645                 650                 655

Arg Ala Arg Ala Leu Tyr Asn Ala Gly Phe Arg Ser Val Glu Ala Ile
                  660                 665                 670

Ala Asn Ala Lys Pro Ala Glu Leu Leu Ala Val Glu Gly Ile Gly Ala
                  675                 680                 685

Lys Ile Leu Asp Gly Ile Tyr Arg His Leu Gly Ile Glu Lys Arg Val
                  690                 695                 700

Thr Glu Glu Lys Pro Lys Arg Lys Gly Thr Leu Glu Asp Phe Leu Arg
705                 710                 715                 720

<210> SEQ ID NO 21
<211> LENGTH: 799
<212> TYPE: PRT
<213> ORGANISM: Methanospirillum hungatei

<400> SEQUENCE: 21

Met Glu Ile Ala Ser Leu Pro Leu Pro Asp Ser Phe Ile Arg Ala Cys
1                   5                   10                  15

His Ala Lys Gly Ile Arg Ser Leu Tyr Pro Pro Gln Ala Glu Cys Ile
                  20                  25                  30

Glu Lys Gly Leu Leu Glu Gly Lys Asn Leu Leu Ile Ser Ile Pro Thr
                  35                  40                  45

Ala Ser Gly Lys Thr Leu Leu Ala Glu Met Ala Met Trp Ser Arg Ile
50                  55                  60

Ala Ala Gly Gly Lys Cys Leu Tyr Ile Val Pro Leu Arg Ala Leu Ala
65                  70                  75                  80

Ser Glu Lys Tyr Asp Glu Phe Ser Lys Lys Gly Val Ile Arg Val Gly
                  85                  90                  95

Ile Ala Thr Gly Asp Leu Asp Arg Thr Asp Ala Tyr Leu Gly Glu Asn
                  100                 105                 110

Asp Ile Ile Val Ala Thr Ser Glu Lys Thr Asp Ser Leu Leu Arg Asn
                  115                 120                 125

Arg Thr Pro Trp Leu Ser Gln Ile Thr Cys Ile Val Leu Asp Glu Val
                  130                 135                 140

His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Ile Gly Leu Ser
                  165                 170                 175

Ala Thr Ile Gly Asn Pro Ala Gln Leu Ala Glu Trp Leu Asp Ala Thr
                  180                 185                 190

Leu Ile Thr Ser Thr Trp Arg Pro Val Asp Leu Arg Gln Gly Val Tyr
                  195                 200                 205

Tyr Asn Gly Lys Ile Arg Phe Ser Asp Ser Glu Arg Pro Ile Gln Gly
                  210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Ser Arg Arg Asn Ala Glu Gly
                  245                 250                 255

Phe Ala Lys Lys Ala Ala Gly Ala Leu Lys Ala Gly Ser Pro Asp Ser
                  260                 265                 270
```

```
Lys Ala Leu Ala Gln Glu Leu Arg Arg Leu Arg Asp Arg Asp Glu Gly
            275                 280                 285

Asn Val Leu Ala Asp Cys Val Glu Arg Gly Ala Ala Phe His His Ala
        290                 295                 300

Gly Leu Ile Arg Gln Glu Arg Thr Ile Ile Glu Glu Gly Phe Arg Asn
305                 310                 315                 320

Gly Tyr Ile Glu Val Ile Ala Ala Thr Pro Thr Leu Ala Ala Gly Leu
                325                 330                 335

Asn Leu Pro Ala Arg Arg Val Ile Ile Arg Asp Tyr Asn Arg Phe Ala
            340                 345                 350

Ser Gly Leu Gly Met Val Pro Ile Pro Val Gly Glu Tyr His Gln Met
        355                 360                 365

Ala Gly Arg Ala Gly Arg Pro His Leu Asp Pro Tyr Gly Glu Ala Val
    370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
                405                 410                 415

Ser Leu Cys Ala His Ile Leu Ser Leu Ile Ala Thr Gly Phe Ala His
            420                 425                 430

Asp Gln Glu Ala Leu Ser Ser Phe Met Glu Arg Thr Phe Tyr Phe Phe
        435                 440                 445

Gln His Pro Lys Thr Arg Ser Leu Pro Arg Leu Val Ala Asp Ala Ile
    450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
                485                 490                 495

Cys Thr Ala Arg Leu Ile Leu Asp Ser Leu Lys Ser Cys Lys Thr Pro
            500                 505                 510

Thr Leu Ile Gly Leu Leu His Val Ile Cys Val Ser Pro Asp Met Gln
        515                 520                 525

Arg Leu Tyr Leu Lys Ala Ala Asp Thr Gln Leu Leu Arg Thr Phe Leu
    530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Glu Arg Tyr Gly
            580                 585                 590

Ile Gly Ala Gly Asp Leu Tyr Asn Ile Val Asp Ser Gly Lys Trp Leu
        595                 600                 605

Leu His Gly Thr Glu Arg Leu Val Ser Val Glu Met Pro Glu Met Ser
    610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
            660                 665                 670

Ala Gly Leu Ser Thr Ile Ala Arg Ile Ile Gly Glu Gly Ile Ala Arg
        675                 680                 685

Gln Val Ile Asp Glu Ile Thr Gly Val Lys Arg Ser Gly Ile His Ser
```

```
            690                 695                 700
Ser Asp Asp Tyr Gln Gln Lys Thr Pro Glu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
                740                 745                 750

Val Leu Gly Ala Ala Arg Ala Arg Lys Val Leu Ala Phe Leu Ser Asn
                755                 760                 765

Ser Glu Lys Glu Asn Ser Ser Ser Asp Lys Thr Glu Glu Ile Pro Asp
770                 775                 780

Thr Gln Lys Ile Arg Gly Gln Ser Ser Trp Glu Asp Phe Gly Cys
785                 790                 795
```

<210> SEQ ID NO 22
<211> LENGTH: 1756
<212> TYPE: PRT
<213> ORGANISM: Escherichia coli

<400> SEQUENCE: 22

```
Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
                20                  25                  30

Trp Ala Gly Lys Gly Ala Glu Gln Leu Gly Leu Gln Gly Ser Val Asp
            35                  40                  45

Lys Asp Val Phe Thr Arg Leu Leu Glu Gly Arg Leu Pro Asp Gly Ala
50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
                100                 105                 110

Ala Val Arg Gln Val Glu Ala Leu Ala Ser Thr Arg Val Met Thr Asp
            115                 120                 125

Gly Gln Ser Glu Thr Val Leu Thr Gly Asn Leu Val Met Ala Leu Phe
130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
                180                 185                 190

Gln Ile Ala Phe Gly Arg Leu Tyr Arg Glu Lys Leu Lys Glu Gln Val
            195                 200                 205

Glu Ala Leu Gly Tyr Glu Thr Glu Val Val Gly Lys His Gly Met Trp
210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
                245                 250                 255

Ala Ala Leu Asp Thr Arg Lys Ser Lys Gln His Val Asp Pro Glu Ile
                260                 265                 270
```

```
Arg Met Ala Glu Trp Met Gln Thr Leu Lys Glu Thr Gly Phe Asp Ile
            275                 280                 285

Arg Ala Tyr Arg Asp Ala Ala Asp Gln Arg Thr Glu Ile Arg Thr Gln
        290                 295                 300

Ala Pro Gly Pro Ala Ser Gln Asp Gly Pro Asp Val Gln Gln Ala Val
305                 310                 315                 320

Thr Gln Ala Ile Ala Gly Leu Ser Glu Arg Lys Val Gln Phe Thr Tyr
                325                 330                 335

Thr Asp Val Leu Ala Arg Thr Val Gly Ile Leu Pro Pro Glu Asn Gly
            340                 345                 350

Val Ile Glu Arg Ala Arg Ala Gly Ile Asp Glu Ala Ile Ser Arg Glu
        355                 360                 365

Gln Leu Ile Pro Leu Asp Arg Glu Lys Gly Leu Phe Thr Ser Gly Ile
    370                 375                 380

His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Gly Ala Ala Gly Gln Arg Glu Arg
        435                 440                 445

Val Ala Glu Leu Val Met Met Ala Arg Glu Gln Gly Arg Glu Val Gln
    450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Arg Gln Leu Leu Glu Gly
                485                 490                 495

Met Ala Phe Thr Pro Gly Ser Thr Val Ile Val Asp Gln Gly Glu Lys
            500                 505                 510

Leu Ser Leu Lys Glu Thr Leu Thr Leu Leu Asp Gly Ala Ala Arg His
        515                 520                 525

Asn Val Gln Val Leu Ile Thr Asp Ser Gly Gln Arg Thr Gly Thr Gly
    530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
                565                 570                 575

Asn Val Arg Tyr Ala Arg Leu Ala Gly Asp Phe Ala Ala Ser Val Lys
            580                 585                 590

Ala Gly Glu Glu Ser Val Ala Gln Val Ser Gly Val Arg Glu Gln Ala
        595                 600                 605

Ile Leu Thr Gln Ala Ile Arg Ser Glu Leu Lys Thr Gln Gly Val Leu
    610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
                645                 650                 655

Glu Gln Trp Asn Pro Glu Thr Arg Ser His Asp Arg Tyr Val Ile Asp
            660                 665                 670

Arg Val Thr Ala Gln Ser His Ser Leu Thr Leu Arg Asp Ala Gln Gly
        675                 680                 685

Glu Thr Gln Val Val Arg Ile Ser Ser Leu Asp Ser Ser Trp Ser Leu
```

```
      690             695             700
Phe Arg Pro Glu Lys Met Pro Val Ala Asp Gly Glu Arg Leu Arg Val
705             710             715             720
Thr Gly Lys Ile Pro Gly Leu Arg Val Ser Gly Gly Asp Arg Leu Gln
            725             730             735
Val Ala Ser Val Ser Glu Asp Ala Met Thr Val Val Pro Gly Arg
        740             745             750
Ala Glu Pro Ala Ser Leu Pro Val Ser Asp Ser Pro Phe Thr Ala Leu
    755             760             765
Lys Leu Glu Asn Gly Trp Val Glu Thr Pro Gly His Ser Val Ser Asp
    770             775             780
Ser Ala Thr Val Phe Ala Ser Val Thr Gln Met Ala Met Asp Asn Ala
785             790             795             800
Thr Leu Asn Gly Leu Ala Arg Ser Gly Arg Asp Val Arg Leu Tyr Ser
            805             810             815
Ser Leu Asp Glu Thr Arg Thr Ala Glu Lys Leu Ala Arg His Pro Ser
            820             825             830
Phe Thr Val Val Ser Glu Gln Ile Lys Ala Arg Ala Gly Glu Thr Leu
            835             840             845
Leu Glu Thr Ala Ile Ser Leu Gln Lys Ala Gly Leu His Thr Pro Ala
    850             855             860
Gln Gln Ala Ile His Leu Ala Leu Pro Val Leu Glu Ser Lys Asn Leu
865             870             875             880
Ala Phe Ser Met Val Asp Leu Leu Thr Glu Ala Lys Ser Phe Ala Ala
            885             890             895
Glu Gly Thr Gly Phe Thr Glu Leu Gly Gly Glu Ile Asn Ala Gln Ile
            900             905             910
Lys Arg Gly Asp Leu Leu Tyr Val Asp Val Ala Lys Gly Tyr Gly Thr
            915             920             925
Gly Leu Leu Val Ser Arg Ala Ser Tyr Glu Ala Glu Lys Ser Ile Leu
            930             935             940
Arg His Ile Leu Glu Gly Lys Glu Ala Val Thr Pro Leu Met Glu Arg
945             950             955             960
Val Pro Gly Glu Leu Met Glu Thr Leu Thr Ser Gly Gln Arg Ala Ala
            965             970             975
Thr Arg Met Ile Leu Glu Thr Ser Asp Arg Phe Thr Val Gln Gly
            980             985             990
Tyr Ala Gly Val Gly Lys Thr Thr  Gln Phe Arg Ala Val  Met Ser Ala
            995             1000            1005
Val Asn  Met Leu Pro Ala Ser  Glu Arg Pro Arg  Val Val Gly Leu
    1010            1015            1020
Gly Pro  Thr His Arg Ala Val  Gly Glu Met Arg  Ser Ala Gly Val
    1025            1030            1035
Asp Ala  Gln Thr Leu Ala Ser  Phe Leu His Asp  Thr Gln Leu Gln
    1040            1045            1050
Gln Arg  Ser Gly Glu Thr Pro  Asp Phe Ser Asn  Thr Leu Phe Leu
    1055            1060            1065
Leu Asp  Glu Ser Ser Met Val  Gly Asn Thr Glu  Met Ala Arg Ala
    1070            1075            1080
Tyr Ala  Leu Ile Ala Ala Gly  Gly Gly Arg Ala  Val Ala Ser Gly
    1085            1090            1095
Asp Thr  Asp Gln Leu Gln Ala  Ile Ala Pro Gly  Gln Ser Phe Arg
    1100            1105            1110
```

```
Leu Gln Gln Thr Arg Ser Ala Ala Asp Val Val Ile Met Lys Glu
    1115                1120                1125

Ile Val Arg Gln Thr Pro Glu Leu Arg Glu Ala Val Tyr Ser Leu
    1130                1135                1140

Ile Asn Arg Asp Val Glu Arg Ala Leu Ser Gly Leu Glu Ser Val
    1145                1150                1155

Lys Pro Ser Gln Val Pro Arg Leu Glu Gly Ala Trp Ala Pro Glu
    1160                1165                1170

His Ser Val Thr Glu Phe Ser His Ser Gln Glu Ala Lys Leu Ala
    1175                1180                1185

Glu Ala Gln Gln Lys Ala Met Leu Lys Gly Glu Ala Phe Pro Asp
    1190                1195                1200

Ile Pro Met Thr Leu Tyr Glu Ala Ile Val Arg Asp Tyr Thr Gly
    1205                1210                1215

Arg Thr Pro Glu Ala Arg Glu Gln Thr Leu Ile Val Thr His Leu
    1220                1225                1230

Asn Glu Asp Arg Arg Val Leu Asn Ser Met Ile His Asp Ala Arg
    1235                1240                1245

Glu Lys Ala Gly Glu Leu Gly Lys Glu Gln Val Met Val Pro Val
    1250                1255                1260

Leu Asn Thr Ala Asn Ile Arg Asp Gly Glu Leu Arg Arg Leu Ser
    1265                1270                1275

Thr Trp Glu Lys Asn Pro Asp Ala Leu Ala Leu Val Asp Asn Val
    1280                1285                1290

Tyr His Arg Ile Ala Gly Ile Ser Lys Asp Asp Gly Leu Ile Thr
    1295                1300                1305

Leu Gln Asp Ala Glu Gly Asn Thr Arg Leu Ile Ser Pro Arg Glu
    1310                1315                1320

Ala Val Ala Glu Gly Val Thr Leu Tyr Thr Pro Asp Lys Ile Arg
    1325                1330                1335

Val Gly Thr Gly Asp Arg Met Arg Phe Thr Lys Ser Asp Arg Glu
    1340                1345                1350

Arg Gly Tyr Val Ala Asn Ser Val Trp Thr Val Thr Ala Val Ser
    1355                1360                1365

Gly Asp Ser Val Thr Leu Ser Asp Gly Gln Gln Thr Arg Val Ile
    1370                1375                1380

Arg Pro Gly Gln Glu Arg Ala Glu Gln His Ile Asp Leu Ala Tyr
    1385                1390                1395

Ala Ile Thr Ala His Gly Ala Gln Gly Ala Ser Glu Thr Phe Ala
    1400                1405                1410

Ile Ala Leu Glu Gly Thr Glu Gly Asn Arg Lys Leu Met Ala Gly
    1415                1420                1425

Phe Glu Ser Ala Tyr Val Ala Leu Ser Arg Met Lys Gln His Val
    1430                1435                1440

Gln Val Tyr Thr Asp Asn Arg Gln Gly Trp Thr Asp Ala Ile Asn
    1445                1450                1455

Asn Ala Val Gln Lys Gly Thr Ala His Asp Val Leu Glu Pro Lys
    1460                1465                1470

Pro Asp Arg Glu Val Met Asn Ala Gln Arg Leu Phe Ser Thr Ala
    1475                1480                1485

Arg Glu Leu Arg Asp Val Ala Ala Gly Arg Ala Val Leu Arg Gln
    1490                1495                1500
```

```
Ala Gly Leu Ala Gly Gly Asp Ser Pro Ala Arg Phe Ile Ala Pro
    1505                1510                1515

Gly Arg Lys Tyr Pro Gln Pro Tyr Val Ala Leu Pro Ala Phe Asp
    1520                1525                1530

Arg Asn Gly Lys Ser Ala Gly Ile Trp Leu Asn Pro Leu Thr Thr
    1535                1540                1545

Asp Asp Gly Asn Gly Leu Arg Gly Phe Ser Gly Glu Gly Arg Val
    1550                1555                1560

Lys Gly Ser Gly Asp Ala Gln Phe Val Ala Leu Gln Gly Ser Arg
    1565                1570                1575

Asn Gly Glu Ser Leu Leu Ala Asp Asn Met Gln Asp Gly Val Arg
    1580                1585                1590

Ile Ala Arg Asp Asn Pro Asp Ser Gly Val Val Val Arg Ile Ala
    1595                1600                1605

Gly Glu Gly Arg Pro Trp Asn Pro Gly Ala Ile Thr Gly Gly Arg
    1610                1615                1620

Val Trp Gly Asp Ile Pro Asp Asn Ser Val Gln Pro Gly Ala Gly
    1625                1630                1635

Asn Gly Glu Pro Val Thr Ala Glu Val Leu Ala Gln Arg Gln Ala
    1640                1645                1650

Glu Glu Ala Ile Arg Arg Glu Thr Glu Arg Arg Ala Asp Glu Ile
    1655                1660                1665

Val Arg Lys Met Ala Glu Asn Lys Pro Asp Leu Pro Asp Gly Lys
    1670                1675                1680

Thr Glu Leu Ala Val Arg Asp Ile Ala Gly Gln Glu Arg Asp Arg
    1685                1690                1695

Ser Ala Ile Ser Glu Arg Glu Thr Ala Leu Pro Glu Ser Val Leu
    1700                1705                1710

Arg Glu Ser Gln Arg Glu Arg Glu Ala Val Arg Glu Val Ala Arg
    1715                1720                1725

Glu Asn Leu Leu Gln Glu Arg Leu Gln Gln Met Glu Arg Asp Met
    1730                1735                1740

Val Arg Asp Leu Gln Lys Glu Lys Thr Leu Gly Gly Asp
    1745                1750                1755

<210> SEQ ID NO 23
<211> LENGTH: 726
<212> TYPE: PRT
<213> ORGANISM: Methanococcoides burtonii

<400> SEQUENCE: 23

Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
                20                  25                  30

Gln Gln Gln Leu Val Leu Phe Glu Gly Ala Cys Gly Thr Gly Lys Thr
            35                  40                  45

Leu Ser Ala Leu Val Pro Ala Leu His Val Gly Lys Met Leu Gly Lys
        50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
            100                 105                 110
```

```
Cys Ser Val Lys Arg Glu Asn Thr Phe Glu Leu Met Glu Thr Glu Arg
        115                 120                 125

Glu Ile Tyr Leu Lys Arg Gln Glu Leu Asn Ser Ala Arg Asp Ser Tyr
        130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
                180                 185                 190

Arg Glu Trp Leu Tyr Lys Glu Val Arg Ser Pro Glu Gly Ile Asn Asp
        195                 200                 205

His Ala Ile Lys Asp Gly Met Cys Gly Tyr Glu Leu Val Lys Arg Glu
        210                 215                 220

Leu Lys His Ala Asp Leu Leu Ile Cys Asn Tyr His His Val Leu Asn
225                 230                 235                 240

Pro Asp Ile Phe Ser Thr Val Leu Gly Trp Ile Glu Lys Glu Pro Gln
                245                 250                 255

Glu Thr Ile Val Ile Phe Asp Glu Ala His Asn Leu Glu Ser Ala Ala
        260                 265                 270

Arg Ser His Ser Ser Leu Ser Leu Thr Glu His Ser Ile Glu Lys Ala
        275                 280                 285

Ile Thr Glu Leu Glu Ala Asn Leu Asp Leu Leu Ala Asp Asp Asn Ile
        290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Arg Val Arg Lys Asn Trp Tyr
                325                 330                 335

Asp Ile Arg Ile Ser Asp Pro Tyr Glu Arg Asn Asp Ile Val Arg Gly
        340                 345                 350

Lys Phe Leu Arg Gln Ala Lys Gly Asp Phe Gly Glu Lys Asp Asp Ile
        355                 360                 365

Gln Ile Leu Leu Ser Glu Ala Ser Glu Leu Gly Ala Lys Leu Asp Glu
        370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
                405                 410                 415

Ser His Asn Leu Asn Tyr Tyr Pro Ile Leu Asn Val Arg Arg Asp Met
                420                 425                 430

Asn Asp Glu Ile Tyr Gly Arg Val Glu Leu Phe Thr Cys Ile Pro Lys
        435                 440                 445

Asn Val Thr Glu Pro Leu Phe Asn Ser Leu Phe Ser Val Ile Leu Met
450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Pro Leu Phe Ala Lys Asn
                500                 505                 510

Arg Asp Asp Arg His Val Thr Glu Leu Leu Glu Gln Val Leu Leu Asp
        515                 520                 525
```

```
Ser Ile Glu Asn Ser Lys Gly Asn Val Ile Leu Phe Gln Ser Ala
        530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Asn Gly Lys Ala Val Leu Leu Ser
            580                 585                 590

Tyr Leu Trp Gly Thr Leu Ser Glu Gly Ile Asp Tyr Arg Asp Gly Arg
        595                 600                 605

Gly Arg Thr Val Ile Ile Gly Val Gly Tyr Pro Ala Leu Asn Asp
        610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655

Gln Ala Met Gly Arg Val Val Arg Ser Pro Thr Asp Tyr Gly Ala Arg
                660                 665                 670

Ile Leu Leu Asp Gly Arg Phe Leu Thr Asp Ser Lys Lys Arg Phe Gly
        675                 680                 685

Lys Phe Ser Val Phe Glu Val Phe Pro Pro Ala Glu Arg Ser Glu Phe
        690                 695                 700

Val Asp Val Asp Pro Glu Lys Val Lys Tyr Ser Leu Met Asn Phe Phe
705                 710                 715                 720

Met Asp Asn Asp Glu Gln
                725

<210> SEQ ID NO 24
<211> LENGTH: 439
<212> TYPE: PRT
<213> ORGANISM: unknown
<220> FEATURE:
<223> OTHER INFORMATION: Dda 1993

<400> SEQUENCE: 24

Met Thr Phe Asp Asp Leu Thr Glu Gly Gln Lys Asn Ala Phe Asn Ile
1               5                   10                  15

Val Met Lys Ala Ile Lys Glu Lys Lys His Val Thr Ile Asn Gly
            20                  25                  30

Pro Ala Gly Thr Gly Lys Thr Thr Leu Thr Lys Phe Ile Ile Glu Ala
            35                  40                  45

Leu Ile Ser Thr Gly Glu Thr Gly Ile Ile Leu Ala Ala Pro Thr His
        50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
        115                 120                 125

Leu Ser Thr Ile Pro Pro Trp Cys Thr Ile Ile Gly Ile Gly Asp Asn
    130                 135                 140

Lys Gln Ile Arg Pro Val Asp Pro Gly Glu Asn Thr Ala Tyr Ile Ser
145                 150                 155                 160
```

```
Pro Phe Phe Thr His Lys Asp Phe Tyr Gln Cys Glu Leu Thr Glu Val
            165                 170                 175

Lys Arg Ser Asn Ala Pro Ile Ile Asp Val Ala Thr Asp Val Arg Asn
        180                 185                 190

Gly Lys Trp Ile Tyr Asp Lys Val Asp Gly His Gly Val Arg Gly
    195                 200                 205

Phe Thr Gly Asp Thr Ala Leu Arg Asp Phe Met Val Asn Tyr Phe Ser
    210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Ile Val Met Gln
            260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Ile Glu Ala Glu Tyr
    290                 295                 300

Thr Ser Thr Phe Val Lys Ala Arg Gly Val Pro Gly Glu Tyr Leu Ile
305                 310                 315                 320

Arg His Trp Asp Leu Thr Val Glu Thr Tyr Gly Asp Asp Glu Tyr Tyr
                325                 330                 335

Arg Glu Lys Ile Lys Ile Ile Ser Asp Glu Glu Leu Tyr Lys Phe
            340                 345                 350

Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
    370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
            420                 425                 430

Arg Tyr Asp Val Phe Tyr Val
        435

<210> SEQ ID NO 25
<211> LENGTH: 970
<212> TYPE: PRT
<213> ORGANISM: Clostridium botulinum

<400> SEQUENCE: 25

Met Leu Ser Val Ala Asn Val Arg Ser Pro Ser Ala Ala Ala Ser Tyr
1               5                   10                  15

Phe Ala Ser Asp Asn Tyr Tyr Ser Ala Asp Ala Asp Arg Ser Gly
            20                  25                  30

Gln Trp Ile Gly Asp Gly Ala Lys Arg Leu Gly Leu Glu Gly Lys Val
        35                  40                  45

Glu Ala Arg Ala Phe Asp Ala Leu Leu Arg Gly Glu Leu Pro Asp Gly
    50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95
```

```
Asp Glu Arg Ile Ile Ala Ala Tyr Arg Glu Ala Val Val Glu Ala Leu
            100                 105                 110

His Trp Ala Glu Lys Asn Ala Glu Thr Arg Val Val Glu Lys Gly
            115                 120                 125

Met Val Val Thr Gln Ala Thr Gly Asn Leu Ala Ile Gly Leu Phe Gln
130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
            195                 200                 205

Val Leu Lys His Gly Asn Phe Glu Ala Arg Gly Ile Ser Arg Glu Gln
            210                 215                 220

Val Met Ala Phe Ser Thr Arg Arg Lys Glu Val Leu Glu Ala Arg Arg
225                 230                 235                 240

Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
            275                 280                 285

Ala Arg Thr Lys Ala Leu Gly Gln Gly Met Glu Ala Thr Arg Ile Gly
            290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Ser Val Leu Lys
                325                 330                 335

Gln Asp Arg Gln Thr Ile Ala Ala Ala Gln Ala Val Ala Ser Ala Val
            340                 345                 350

Arg His Leu Ser Gln Arg Glu Ala Ala Phe Glu Arg Thr Ala Leu Tyr
            355                 360                 365

Lys Ala Ala Leu Asp Phe Gly Leu Pro Thr Thr Ile Ala Asp Val Glu
            370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
                405                 410                 415

Gln Arg Ile Leu Ser Glu Val Ala Ala Gly Lys Gly Asp Ser Ser Pro
            420                 425                 430

Ala Ile Thr Pro Gln Lys Ala Ala Ala Ser Val Gln Ala Ala Ala Leu
            435                 440                 445

Thr Gly Gln Gly Phe Arg Leu Asn Glu Gly Gln Leu Ala Ala Ala Arg
            450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
            500                 505                 510
```

```
Gln Met Leu Glu Arg Asp Thr Gly Ile Gly Ser Gln Thr Leu Ala Arg
            515                 520                 525

Phe Leu Gly Gly Trp Asn Lys Leu Leu Asp Asp Pro Gly Asn Val Ala
        530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
        595                 600                 605

Arg Ala Gly Ile Ala Arg Ala Glu Met Ala Thr Asn Leu Arg Ala Arg
610                 615                 620

Asp Pro Val Val Arg Glu Ala Gln Ala Ala Gln Ala Gly Asp Val
625                 630                 635                 640

Arg Lys Ala Leu Arg His Leu Lys Ser His Thr Val Glu Ala Arg Gly
            645                 650                 655

Asp Gly Ala Gln Val Ala Ala Glu Thr Trp Leu Ala Leu Asp Lys Glu
        660                 665                 670

Thr Arg Ala Arg Thr Ser Ile Tyr Ala Ser Gly Arg Ala Ile Arg Ser
675                 680                 685

Ala Val Asn Ala Ala Val Gln Gln Gly Leu Leu Ala Ser Arg Glu Ile
            690                 695                 700

Gly Pro Ala Lys Met Lys Leu Glu Val Leu Asp Arg Val Asn Thr Thr
705                 710                 715                 720

Arg Glu Glu Leu Arg His Leu Pro Ala Tyr Arg Ala Gly Arg Val Leu
                725                 730                 735

Glu Val Ser Arg Lys Gln Gln Ala Leu Gly Leu Phe Ile Gly Glu Tyr
            740                 745                 750

Arg Val Ile Gly Gln Asp Arg Lys Gly Lys Leu Val Glu Val Glu Asp
        755                 760                 765

Lys Arg Gly Lys Arg Phe Arg Phe Asp Pro Ala Arg Ile Arg Ala Gly
770                 775                 780

Lys Gly Asp Asp Asn Leu Thr Leu Leu Glu Pro Arg Lys Leu Glu Ile
785                 790                 795                 800

His Glu Gly Asp Arg Ile Arg Trp Thr Arg Asn Asp His Arg Arg Gly
                805                 810                 815

Leu Phe Asn Ala Asp Gln Ala Arg Val Val Glu Ile Ala Asn Gly Lys
            820                 825                 830

Val Thr Phe Glu Thr Ser Lys Gly Asp Leu Val Glu Leu Lys Lys Asp
        835                 840                 845

Asp Pro Met Leu Lys Arg Ile Asp Leu Ala Tyr Ala Leu Asn Val His
850                 855                 860

Met Ala Gln Gly Leu Thr Ser Asp Arg Gly Ile Ala Val Met Asp Ser
865                 870                 875                 880

Arg Glu Arg Asn Leu Ser Asn Gln Lys Thr Phe Leu Val Thr Val Thr
                885                 890                 895

Arg Leu Arg Asp His Leu Thr Leu Val Val Asp Ser Ala Asp Lys Leu
            900                 905                 910

Gly Ala Ala Val Ala Arg Asn Lys Gly Glu Lys Ala Ser Ala Ile Glu
        915                 920                 925

Val Thr Gly Ser Val Lys Pro Thr Ala Thr Lys Gly Ser Gly Val Asp
```

```
                930               935                940
Gln Pro Lys Ser Val Glu Ala Asn Lys Ala Glu Lys Glu Leu Thr Arg
945                 950                 955                 960

Ser Lys Ser Lys Thr Leu Asp Phe Gly Ile
                965                 970

<210> SEQ ID NO 26
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 26
ggttaaacac ccaagcagac gccgcaatat cagcaccaac agaaacaacc tttgaggcga      60
gcggtcaa                                                              68

<210> SEQ ID NO 27
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 27
tttttttttt tt                                                         12

<210> SEQ ID NO 28
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 28
ggttgtttct gttggtgctg atattgcggc gtctgcttgg gtgtttaacc t              51

<210> SEQ ID NO 29
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 29
cgttctgttt atgtttcttg gacactgatt gacacggttt agtagaac                  48

<210> SEQ ID NO 30
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 30
tttttttttt tttttttttt tttttttca agaaacataa acagaacgt                  49

<210> SEQ ID NO 31
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 31
```

```
Thr Thr Gly Ala Cys Cys Gly Cys Thr Cys Gly Cys Cys Thr Cys
1               5                  10                  15
```

<210> SEQ ID NO 32
<211> LENGTH: 10
<212> TYPE: DNA
<213> ORGANISM: Artificial Sequence
<220> FEATURE:
<223> OTHER INFORMATION: Synthetic Polynucleotide

<400> SEQUENCE: 32
tttttttttt                                                          10

<210> SEQ ID NO 33
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 33
ggttgtttct gttggtgctg atattgcac                                     29

<210> SEQ ID NO 34
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 34
gcaatatcag caccaacaga aa                                            22

<210> SEQ ID NO 35
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 35
gaggcgagcg gtcaa                                                    15

<210> SEQ ID NO 36
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 36
tgagtgacca atcagctacg tttttttttt tt                                 32

<210> SEQ ID NO 37
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 37
ggttgtttct gttggtgctg atattgct                                      28

<210> SEQ ID NO 38
<211> LENGTH: 22

<212> TYPE: DNA
<213> ORGANISM: Artificial Sequence
<220> FEATURE:
<223> OTHER INFORMATION: Synthetic Polynucleotide

<400> SEQUENCE: 38
cgtagctgat tggtcactca gt                                             22

<210> SEQ ID NO 39
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 39
cgtcctgtcg ctgtgtctcg gacactgatt gacacggttt agtagagc                 48

<210> SEQ ID NO 40
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 40
tttttttttt tttttttttt ttttttttcg agacacagcg acaggacgtc ct            52

<210> SEQ ID NO 41
<211> LENGTH: 3568
<212> TYPE: DNA
<213> ORGANISM: Artificial Sequence
<220> FEATURE:
<223> OTHER INFORMATION: Synthetic Polynucleotide

<400> SEQUENCE: 41
gccatcagat tgtgtttgtt agtcgctttt ttttttttgga atttttttttt tggaatttttt    60 tttttgcgct aacaacctcc tgccgttttg cccgtgcata tcggtcacga acaaatctga     120
ttactaaaca cagtagcctg gatttgttct atcagtaatc gaccttattc ctaattaaat     180
agagcaaatc cccttattgg gggtaagaca tgaagatgcc agaaaaacat gacctgttgg     240
ccgccattct cgcggcaaag gaacaaggca tcggggcaat ccttgcgttt gcaatggcgt     300
accttcgcgg cagatataat ggcggtgcgt ttacaaaaac agtaatcgac gcaacgatgt     360
gcgccattat cgcctagttc attcgtgacc ttctcgactt cgccggacta agtagcaatc     420
tcgcttatat aacgagcgtg tttatcggct acatcggtac tgactcgatt ggttcgctta     480
tcaaacgctt cgctgctaaa aaagccggag tagaagatgg tagaaatcaa taatcaacgt     540
aaggcgttcc tcgatatgct ggcgtggtcg gagggaactg ataacggacg tcagaaaacc     600
agaaatcatg gttatgacgt cattgtaggc ggagagctat ttactgatta ctccgatcac     660
cctcgcaaac ttgtcacgct aaacccaaaa ctcaaatcaa caggcgccgg acgctaccag     720
cttctttccc gttggtggga tgcctaccgc aagcagcttg gcctgaaaga cttctctccg     780
aaaagtcagg acgctgtggc attgcagcag attaaggagc gtggcgcttt acctatgatt     840
gatcgtggtg atatccgtca ggcaatcgac cgttgcagca atatctgggc ttcactgccg     900
ggcgctggtt atggtcagtt cgagcataag gctgacagcc tgattgcaaa attcaaagaa     960
gcgggcggaa cggtcagaga gattgatgta tgagcagagt caccgcgatt atctccgctc    1020
tggttatctg catcatcgtc tgcctgtcat gggctgttaa tcattaccgt gataacgcca    1080

-continued

```
ttacctacaa agcccagcgc gacaaaaatg ccagagaact gaagctggcg aacgcggcaa    1140
ttactgacat gcagatgcgt cagcgtgatg ttgctgcgct cgatgcaaaa tacacgaagg    1200
agttagctga tgctaaagct gaaaatgatg ctctgcgtga tgatgttgcc gctggtcgtc    1260
gtcggttgca catcaaagca gtctgtcagt cagtgcgtga agccaccacc gcctccggcg    1320
tggataatgc agcctccccc cgactggcag acaccgctga acgggattat ttcaccctca    1380
gagagaggct gatcactatg caaaacaac tggaaggaac ccagaagtat attaatgagc     1440
agtgcagata gagttgccca tatcgatggg caactcatgc aattattgtg agcaatacac    1500
acgcgcttcc agcggagtat aaatgcctaa agtaataaaa ccgagcaatc catttacgaa    1560
tgtttgctgg gtttctgttt taacaacatt ttctgcgccg ccacaaattt tggctgcatc    1620
gacagttttc ttctgcccaa ttccagaaac gaagaaatga tgggtgatgg tttcctttgg    1680
tgctactgct gccggtttgt tttgaacagt aaacgtctgt tgagcacatc ctgtaataag    1740
cagggccagc gcagtagcga gtagcatttt tttcatggtg ttattcccga tgcttttga    1800 agttcgcaga atcgtatgtg tagaaaatta acaaaccct aaacaatgag ttgaaatttc     1860
atattgttaa tatttattaa tgtatgtcag gtgcgatgaa tcgtcattgt attcccggat    1920
taactatgtc cacagccctg acggggaact tctctgcggg agtgtccggg aataattaaa    1980
acgatgcaca cagggtttag cgcgtacacg tattgcatta tgccaacgcc ccggtgctga    2040
cacggaagaa accggacgtt atgatttagc gtggaaagat ttgtgtagtg ttctgaatgc    2100
tctcagtaaa tagtaatgaa ttatcaaagg tatagtaata tcttttatgt tcatggatat    2160
ttgtaaccca tcggaaaact cctgctttag caagattttc cctgtattgc tgaaatgtga    2220
tttctcttga tttcaaccta tcataggacg tttctataag atgcgtgttt cttgagaatt    2280
taacatttac aaccttttta agtccttta ttaacacggt gttatcgttt ctaacacga     2340 tgtgaatatt atctgtggct agatagtaaa tataatgtga gacgttgtga cgttttagtt    2400
cagaataaaa caattcacag tctaaatctt ttcgcacttg atcgaatatt tctttaaaaa    2460
tggcaacctg agccattggt aaaaccttcc atgtgatacg agggcgcgta gtttgcatta    2520
tcgtttttat cgtttcaatc tggtctgacc tccttgtgtt ttgttgatga tttatgtcaa    2580
atattaggaa tgttttcact taatagtatt ggttgcgtaa caaagtgcgg tcctgctggc    2640
attctggagg gaaatacaac cgacagatgt atgtaaggcc aacgtgctca atcttcata    2700 cagaaagatt tgaagtaata ttttaaccgc tagatgaaga gcaagcgcat ggagcgacaa    2760
aatgaataaa gaacaatctg ctgatgatcc ctccgtggat ctgattcgtg taaaaaatat    2820
gcttaatagc accatttcta tgagttaccc tgatgttgta attgcatgta tagaacataa    2880
ggtgtctctg gaagcattca gagcaattga ggcagcgttg gtgaagcacg ataataaat    2940 gaaggattat tccctggtgg ttgactgatc accataactg ctaatcattc aaactattta   3000
gtctgtgaca gagccaacac gcagtctgtc actgtcagga aagtggtaaa actgcaactc    3060
aattactgca atgccctcgt aattaagtga atttacaata tcgtcctgtt cggagggaag    3120
aacgcgggat gttcattctt catcactttt aattgatgta tatgctctct tttctgacgt    3180
tagtctccga cggcaggctt caatgaccca ggctgagaaa ttcccggacc cttttttgctc   3240 aagagcgatg ttaatttgtt caatcatttg gttaggaaag cggatgttgc gggttgttgt    3300
tctgcgggtt ctgttcttcg ttgacatgag gttgccccgt attcagtgtc gctgatttgt    3360
attgtctgaa gttgttttta cgttaagttg atgcagatca attaatacga tacctgcgtc    3420
ataattgatt atttgacgtg gtttgatggc ctccacgcac gttgtgatat gtagatgata    3480
```

-continued

| | |
|---|---|
| atcattatca ctttacgggt cctttccggt gaaaaaaaag gtaccaaaaa aaacatcgtc | 3540 |
| gtgagtagtg aaccgtaagc atgtagga | 3568 |

<210> SEQ ID NO 42
<211> LENGTH: 3565
<212> TYPE: DNA
<213> ORGANISM: Artificial Sequence
<220> FEATURE:
<223> OTHER INFORMATION: Synthetic Polynucleotide

<400> SEQUENCE: 42

| | |
|---|---|
| acatgcttac ggttcactac tcacgacgat gttttttttg gtacctttt tttcaccgga | 60 |
| aaggacccgt aaagtgataa tgattatcat ctacatatca caacgtgcgt ggaggccatc | 120 |
| aaaccacgtc aaataatcaa ttatgacgca ggtatcgtat taattgatct gcatcaactt | 180 |
| aacgtaaaaa caacttcaga caatacaaat cagcgacact gaatacgggg caacctcatg | 240 |
| tcaacgaaga acagaacccg cagaacaaca acccgcaaca tccgctttcc taaccaaatg | 300 |
| attgaacaaa ttaacatcgc tcttgagcaa aaagggtccg ggaatttctc agcctgggtc | 360 |
| attgaagcct gccgtcggag actaacgtca gaaaagagag catatacatc aattaaaagt | 420 |
| gatgaagaat gaacatcccg cgttcttccc tccgaacagg acgatattgt aaattcactt | 480 |
| aattacgagg gcattgcagt aattgagttg cagttttacc actttcctga cagtgacaga | 540 |
| ctgcgtgttg gctctgtcac agactaaata gtttgaatga ttagcagtta tggtgatcag | 600 |
| tcaaccacca gggaataatc cttcatatta ttatcgtgct tcaccaacgc tgcctcaatt | 660 |
| gctctgaatg cttccagaga caccttatgt tctatacatg caattacaac atcagggtaa | 720 |
| ctcatagaaa tggtgctatt aagcatattt tttacacgaa tcagatccac ggagggatca | 780 |
| tcagcagatt gttctttatt cattttgtcg ctccatgcgc ttgctcttca tctagcggtt | 840 |
| aaaatattac ttcaaatctt tctgtatgaa gatttgagca cgttggcctt acatacatct | 900 |
| gtcggttgta tttccctcca gaatgccagc aggaccgcac tttgttacgc aaccaatact | 960 |
| attaagtgaa acattccta atatttgaca taaatcatca acaaaacaca aggaggtcag | 1020 |
| accagattga acgataaaa acgataatgc aaactacgcg ccctcgtatc acatggaagg | 1080 |
| ttttaccaat ggctcaggtt gccattttta agaaatatt cgatcaagtg cgaaaagatt | 1140 |
| tagactgtga attgttttat tctgaactaa acgtcacaa cgtctcacat tatatttact | 1200 |
| atctagccac agataatatt cacatcgtgt tagaaaacga taacaccgtg ttaataaaag | 1260 |
| gacttaaaaa ggttgtaaat gttaaattct caagaaacac gcatcttata gaaacgtcct | 1320 |
| atgataggtt gaaatcaaga gaaatcacat ttcagcaata cagggaaaat cttgctaaag | 1380 |
| caggagtttt ccgatgggtt acaaatatcc atgaacataa aagatattac tatacctttg | 1440 |
| ataattcatt actatttact gagagcattc agaacactac acaaatcttt ccacgctaaa | 1500 |
| tcataacgtc cggtttcttc cgtgtcagca ccggggcgtt ggcataatgc aatacgtgta | 1560 |
| cgcgctaaac cctgtgtgca tcgttttaat tattcccgga cactcccgca gagaagttcc | 1620 |
| ccgtcagggc tgtggacata gttaatccgg gaatacaatg acgattcatc gcacctgaca | 1680 |
| tacattaata aatattaaca atatgaaatt tcaactcatt gtttagggtt tgtttaattt | 1740 |
| tctacacata cgattctgcg aacttcaaaa agcatcggga ataacaccat gaaaaaaatg | 1800 |
| ctactcgcta ctgcgctggc cctgcttatt acaggatgtg ctcaacagac gtttactgtt | 1860 |
| caaaacaaac cggcagcagt agcaccaaag gaaaccatca cccatcattt cttcgtttct | 1920 |

```
ggaattgggc agaagaaaac tgtcgatgca gccaaaattt gtggcggcgc agaaaatgtt     1980
gttaaaacag aaacccagca acattcgta aatggattgc tcggttttat tactttaggc     2040
atttatactc cgctggaagc gcgtgtgtat tgctcacaat aattgcatga gttgcccatc     2100
gatatgggca actctatctg cactgctcat taatatactt ctgggttcct tccagttgtt     2160
tttgcatagt gatcagcctc tctctgaggg tgaaataatc ccgttcagcg gtgtctgcca     2220
gtcgggggga ggctgcatta ccacgccgg aggcggtggt ggcttcacgc actgactgac      2280
agactgcttt gatgtgcaac cgacgacgac cagcggcaac atcatcacgc agagcatcat     2340
tttcagcttt agcatcagct aactccttcg tgtattttgc atcgagcgca gcaacatcac     2400
gctgacgcat ctgcatgtca gtaattgccg cgttcgccag cttcagttct ctggcattt      2460 tgtcgcgctg gctttgtag gtaatggcgt tatcacggta atgattaaca gcccatgaca      2520
ggcagacgat gatgcagata accagagcgg agataatcgc ggtgactctg ctcatacatc     2580
aatctctctg accgttccgc cgcttcttt gaattttgca atcaggctgt cagccttatg      2640
ctcgaactga ccataaccag cgcccggcag tgaagcccag atattgctgc aacggtcgat     2700
tgcctgacgg atatcaccac gatcaatcat aggtaaagcg ccacgctcct taatctgctg     2760
caatgccaca gcgtcctgac ttttcggaga gaagtctttc aggccaagct gcttgcggta     2820
ggcatcccac caacgggaaa gaagctggta gcgtccggcg cctgttgatt tgagttttgg     2880
gtttagcgtg acaagtttgc gagggtgatc ggagtaatca gtaaatagct ctccgcctac     2940
aatgacgtca taaccatgat ttctggtttt ctgacgtccg ttatcagttc cctccgacca     3000
cgccagcata tcgaggaacg ccttacgttg attattgatt tctaccatct tctactccgg     3060
cttttttagc agcgaagcgt ttgataagcg aaccaatcga gtcagtaccg atgtagccga     3120
taaacacgct cgttatataa gcgagattgc tacttagtcc ggcgaagtcg agaaggtcac     3180
gaatgaacta ggcgataatg gcgcacatcg ttgcgtcgat tactgttttt gtaaacgcac     3240
cgccattata tctgccgcga aggtacgcca ttgcaaacgc aaggattgcc ccgatgcctt     3300
gttcctttgc cgcgagaatg gcggccaaca ggtcatgttt ttctggcatc ttcatgtctt     3360
acccccaata aggggatttg ctctatttaa ttaggaataa ggtcgattac tgatagaaca     3420
aatccaggct actgtgttta gtaatcagat ttgttcgtga ccgatatgca cgggcaaaac     3480
ggcaggaggt tgttagcgca aaaaaaaaat tccaaaaaaa aaattccaaa aaaaaaagc      3540 gactaacaaa cacaatctga tggca                                          3565

<210> SEQ ID NO 43
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 43
gcaatatcag caccaacaga aacaaccttt gaggcgagcg gtcaa                    45

<210> SEQ ID NO 44
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 44
ggttaaacac ccaagcagac gcctttttttt tttcgtcctg tcgctgtgtc tcgg          54
```

<210> SEQ ID NO 45
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 45
cgagacacag cgacaggacg                                              20

<210> SEQ ID NO 46
<211> LENGTH: 3560
<212> TYPE: DNA
<213> ORGANISM: Artificial Sequence
<220> FEATURE:
<223> OTHER INFORMATION: Synthetic Polynucleotide

<400> SEQUENCE: 46
gccatcagat tgtgtttgtt agtcgctttt ttttttttgga atttttttt tggaattttt     60 tttttgcgct aacaacctcc tgccgttttg cccgtgcata tcggtcacga acaaatctga   120
ttactaaaca cagtagcctg gatttgttct atcagtaatc gaccttattc ctaattaaat   180
agagcaaatc cccttattgg gggtaagaca tgaagatgcc agaaaaacat gacctgttgg   240
ccgccattct cgcggcaaag gaacaaggca tcggggcaat ccttgcgttt gcaatggcgt   300
accttcgcgg cagatataat ggcggtgcgt ttacaaaaac agtaatcgac gcaacgatgt   360
gcgccattat cgcctagttc attcgtgacc ttctcgactt cgccggacta agtagcaatc   420
tcgcttatat aacgagcgtg tttatcggct acatcggtac tgactcgatt ggttcgctta   480
tcaaacgctt cgctgctaaa aaagccggag tagaagatgg tagaaatcaa taatcaacgt   540
aaggcgttcc tcgatatgct ggcgtggtcg gagggaactg ataacggacg tcagaaaacc   600
agaaatcatg gttatgacgt cattgtaggc ggagagctat ttactgatta ctccgatcac   660
cctcgcaaac ttgtcacgct aaacccaaaa ctcaaatcaa caggcgccgg acgctaccag   720 cttcttccc gttggtggga tgcctaccgc aagcagcttg gcctgaaaga cttctctccg   780
aaaagtcagg acgctgtggc attgcagcag attaaggagc gtggcgcttt acctatgatt   840
gatcgtggtg atatccgtca ggcaatcgac cgttgcagca atatctgggc ttcactgccg   900
ggcgctggtt atggtcagtt cgagcataag gctgacagcc tgattgcaaa attcaaagaa   960
gcgggcggaa cggtcagaga gattgatgta tgagcagagt caccgcgatt atctccgctc  1020
tggttatctg catcatcgtc tgcctgtcat gggctgttaa tcattaccgt gataacgcca  1080
ttacctacaa agcccagcgc gacaaaaatg ccagagaact gaagctggcg aacgcggcaa  1140
ttactgacat gcagatgcgt cagcgtgatg ttgctgcgct cgatgcaaaa tacacgaagg  1200
agttagctga tgctaaagct gaaaatgatg ctctgcgtga tgatgttgcc gctggtcgtc  1260
gtcggttgca catcaaagca gtctgtcagt cagtgcgtga agccaccacc gcctccggcg  1320
tggataatgc agcctccccc cgactggcag acaccgctga acgggattat tcaccctca  1380 gagagaggct gatcactatg caaaaacaac tggaaggaac ccagaagtat attaatgagc  1440
agtgcagata gagttgccca tatcgatggg caactcatgc aattattgtg agcaatacac  1500
acgcgcttcc agcggagtat aaatgcctaa agtaataaaa ccgagcaatc catttacgaa  1560
tgtttgctgg gttctgtttt taacaacatt ttctgcgccg ccacaaattt tggctgcatc  1620
gacagttttc ttctgcccaa ttccagaaac gaagaaatga tgggtgatgg tttcctttgg  1680

```
tgctactgct gccggtttgt tttgaacagt aaacgtctgt tgagcacatc ctgtaataag   1740
cagggccagc gcagtagcga gtagcatttt tttcatggtg ttattcccga tgcttttga    1800 agttcgcaga atcgtatgtg tagaaaatta acaaaccct aaacaatgag ttgaaatttc    1860
atattgttaa tatttattaa tgtatgtcag gtgcgatgaa tcgtcattgt attcccggat   1920
taactatgtc cacagccctg acggggaact tctctgcggg agtgtccggg aataattaaa   1980
acgatgcaca cagggtttag cgcgtacacg tattgcatta tgccaacgcc ccggtgctga   2040
cacggaagaa accggacgtt atgatttagc gtggaaagat ttgtgtagtg ttctgaatgc   2100
tctcagtaaa tagtaatgaa ttatcaaagg tatagtaata tcttttatgt tcatggatat   2160
ttgtaaccca tcggaaaact cctgctttag caagattttc cctgtattgc tgaaatgtga   2220
tttctcttga tttcaaccta tcataggacg tttctataag atgcgtgttt cttgagaatt   2280
taacatttac aaccttttta agtcctttta ttaacacggt gttatcgttt tctaacacga   2340
tgtgaatatt atctgtggct agatagtaaa tataatgtga acgttgtga cgttttagtt    2400 cagaataaaa caattcacag tctaaatctt ttcgcacttg atcgaatatt tctttaaaaa   2460
tggcaacctg agccattggt aaaaccttcc atgtgatacg agggcgcgta gtttgcatta   2520 tcgttttat cgtttcaatc tggtctgacc tccttgtgtt ttgttgatga tttatgtcaa    2580
atattaggaa tgttttcact taatagtatt ggttgcgtaa caaagtgcgg tcctgctggc   2640
attctggagg gaaatacaac cgacagatgt atgtaaggcc aacgtgctca atcttcata    2700 cagaaagatt tgaagtaata ttttaaccgc tagatgaaga gcaagcgcat ggagcgacaa   2760
aatgaataaa gaacaatctg ctgatgatcc ctccgtggat ctgattcgtg taaaaaatat   2820
gcttaatagc accatttcta tgagttaccc tgatgttgta attgcatgta tagaacataa   2880
ggtgtctctg gaagcattca gagcaattga ggcagcgttg gtgaagcacg ataataatat   2940
gaaggattat tccctggtgg ttgactgatc accataactg ctaatcattc aaactattta   3000
gtctgtgaca gagccaacac gcagtctgtc actgtcagga agtggtaaa actgcaactc    3060 aattactgca atgccctcgt aattaagtga atttacaata tcgtcctgtt cggagggaag   3120
aacgcgggat gttcattctt catcactttt aattgatgta tatgctctct tttctgacgt   3180
tagtctccga cggcaggctt caatgaccca ggctgagaaa ttcccggacc cttttgctc    3240 aagagcgatg ttaatttgtt caatcatttg gttaggaaag cggatgttgc gggttgttgt   3300
tctgcgggtt ctgttcttcg ttgacatgag gttgccccgt attcagtgtc gctgatttgt   3360
attgtctgaa gttgttttta cgttaagttg atgcagatca attaatacga tacctgcgtc   3420
ataattgatt attgacgtg gtttgatggc ctccacgcac gttgtgatat gtagatgata   3480
atcattatca ctttacgggt cctttccggt gaaaaaaag gtaccaaaaa aacatcgtc     3540 gtgagtagtg aaccgtaagc                                              3560

<210> SEQ ID NO 47
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 47
cgttctgttt atgtttcttg tttgttagcc ttttggctaa caaacaagaa acataaacag   60
aacg                                                               64
```

US 10,385,389 B2

METHOD FOR ATTACHING ONE OR MORE POLYNUCLEOTIDE BINDING PROTEINS TO A TARGET POLYNUCLEOTIDE

RELATED APPLICATIONS

This application is a national stage filing under U.S.C. § 371 of PCT International Application PCT/GB2015/050140, which has an international filing date of Jan. 22, 2015; is a continuation-in-part of PCT International Application PCT/GB2014/050175, which has an international filing date of Jan. 22, 2014; and claims foreign priority benefits under 35 U.S.C. § 119(a)-(d) or 35 U.S.C. § 365(b) of British application number 1406151.9, filed Apr. 4, 2014, British application number 1406155.0, filed Apr. 4, 2014, and British application number 1416197.0, filed Sep. 12, 2014, the contents of each of which are herein incorporated by reference in their entireties.

FIELD OF THE INVENTION

The invention relates to new methods of attaching one or more polynucleotide binding proteins to a target polynucleotide. The invention also relates to new methods of characterising target polynucleotides.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identities of the nucleotides are derived. Strand sequencing can involve the use of a polynucleotide binding protein to control the movement of the polynucleotide through the pore.

SUMMARY OF THE INVENTION

The inventors have surprisingly demonstrated that it is possible to pre-load one or more polynucleotide binding proteins onto one or more loading moieties and then attach the one or more loading moieties to the target polynucleotide. It is surprising that the one or more polynucleotide binding proteins do not sterically hinder the attachment of the one or more loading moieties to the polynucleotide. It is also surprising that the attachment process does not affect the one or more polynucleotide binding proteins and that they retain their function and ability to bind to the one or more loading moieties after they are attached to the target polynucleotide.

Accordingly, the invention provides a method for attaching one or more polynucleotide binding proteins to a target polynucleotide, comprising:

(a) providing the one or more polynucleotide binding proteins bound to one or more loading moieties; and (b) attaching the one or more loading moieties to the target polynucleotide.

The invention also provides method of characterising a target polynucleotide, comprising:

(a) carrying out a method of the invention;

(b) contacting the target polynucleotide having one or more polynucleotide binding proteins attached provided in step (a) with a transmembrane pore such that the one or more polynucleotide binding proteins control the movement of the polynucleotide with respect to the pore; and (c) taking one or more measurements as the polynucleotide moves with respect to the pore wherein the measurements are indicative of one or more characteristics of the polynucleotide and thereby characterising the target polynucleotide.

The invention also provides a method of preparing a target polynucleotide for characterisation, comprising:

(a) carrying out a method of the invention wherein the one or more polynucleotide binding proteins comprise one or more polymerases; and (b) allowing the one or more polymerases attached to the target polynucleotide provided in step (a) to form one or more polynucleotides using the target polynucleotide as a template and thereby preparing the target polynucleotide for characterisation.

The invention also provides a method of characterising a target polynucleotide, comprising:

(a) carrying out a polymerase-based method of the invention;

(b) contacting the target polynucleotide and the one or more polynucleotides produced in step (a) with a transmembrane pore such that the target polynucleotide and the one or more polynucleotides move with respect to the pore; and (c) taking one or more measurements as the target polynucleotide and the one or more polynucleotides move with respect to the pore wherein the measurements are indicative of one or more characteristics of the polynucleotides and thereby characterising the target polynucleotide.

The invention also provides:

a target polynucleotide modified using a method of the invention;

a loading moiety having one or more bound polynucleotide binding proteins; and a kit for attaching one or more polynucleotide binding proteins to a target polynucleotide, comprising (a) the one or more polynucleotide binding proteins bound to one or more loading moieties and (b) a ligase.

DESCRIPTION OF THE FIGURES

FIGS. 7A-7B show an Agilent Bioanalyser trace illustrating that the enzyme was pre-bound to the MuA Y-adapter.

FIGS. 8A-8B show an Agilent Bioanalyser trace illustrating that when the enzyme was pre-bound to the MuA adapter no adverse effect was seen on the tagmentation of the target DNA.

FIG. 14B shows a single DNA strand moving through the nanopore under the control of the helicase, the labelled regions 1 and 2 correspond to the translocation of region 1 and 2 of the original 3.6 kB DNA construct (SEQ ID NO: 46) and represented schematically in FIG. 14A. The labelled regions 4 and 5 correspond to the complementary strands to regions 1 and 2 which were produced by polymerisation using Phi29-A411C/Q560C. The trace shows the movement index observed when the construct was translocated through the pore under the control of T4 Dda-E94C/C109A/C136A/A360C. The arrow labelled 3 shows a spike in current as the spacers in the hairpin of the final construct (shown as x and labelled 3 in FIG. 14A) translocated through the nanopore. The hairpin adapter and Y adaptor spacers are shown as an x in the DNA construct of FIG. 14A.

DESCRIPTION OF THE SEQUENCE LISTING

Figure 1:
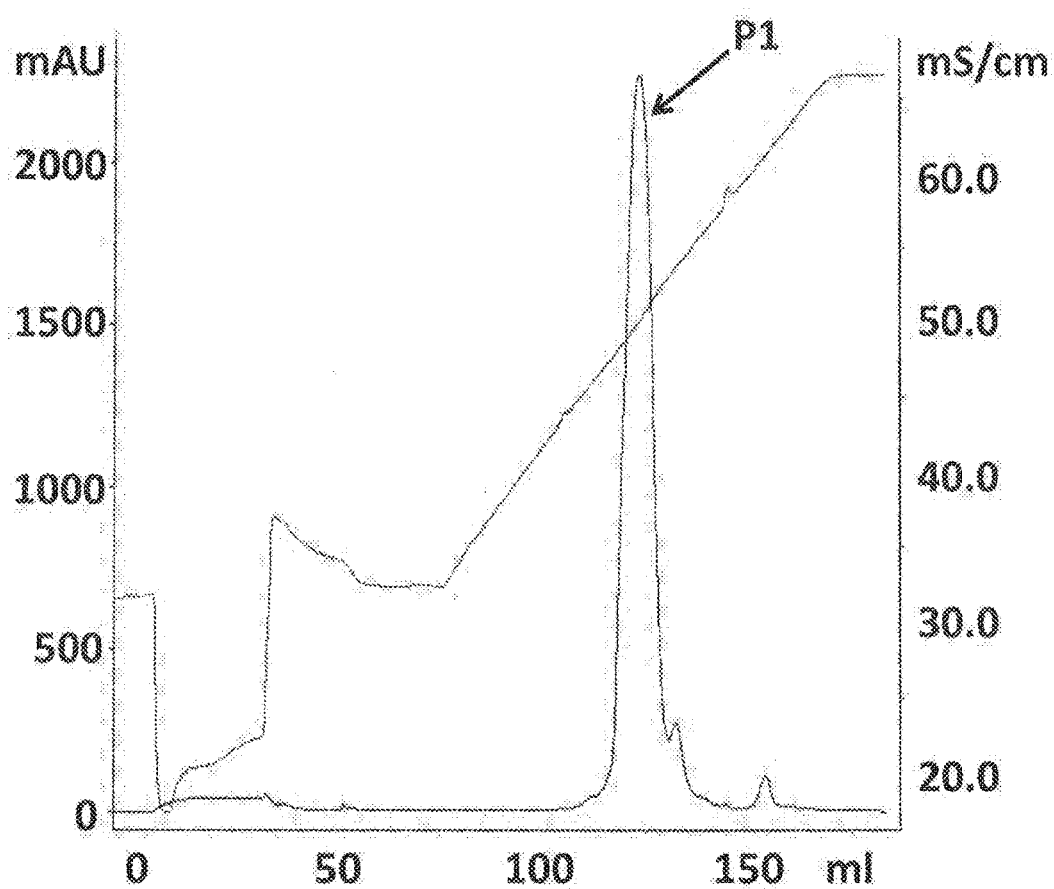
FIG. 1 shows an example FPLC trace after purification of the pre-bound TrwC Cba-L376C/Q594A/K762C to the DNA Hairpin-adapter using an 8 mL POROS HQ-10 column.

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from *E. coli*. It encodes the exonuclease I enzyme (EcoExo I) from *E. coli*.

SEQ ID NO: 11 shows the amino acid sequence of exonuclease I enzyme (EcoExo I) from *E. coli*.

SEQ ID NO: 12 shows the codon optimised polynucleotide sequence derived from the xthA gene from *E. coli*. It encodes the exonuclease III enzyme from *E. coli*.

SEQ ID NO: 13 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the recJ gene from *T. thermophilus*. It encodes the RecJ enzyme from *T. thermophiles* (TthRecJ-cd).

SEQ ID NO: 15 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3' direction (http://www.neb.com/nebecomm/products/productM0262.asp). Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the amino acid sequence of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of Tral Eco.

SEQ ID NO: 23 shows the amino acid sequence of XPD Mbu.

SEQ ID NO: 24 shows the amino acid sequence of Dda 1993.

SEQ ID NO: 25 shows the amino acid sequence of Trwc Cba.

SEQ ID NO: 26 shows a polynucleotide sequence used in Example 1. This sequence has a 5' phosphate.

SEQ ID NO: 27 shows a polynucleotide sequence used in Example 2 and 7.

SEQ ID NO: 28 shows a polynucleotide sequence used in Example 2 and 7.

SEQ ID NO: 29 shows a polynucleotide sequence used in Example 1. This sequence has a 5' phosphate.

SEQ ID NO: 30 shows a polynucleotide sequence used in Example 1.

SEQ ID NO: 31 shows a polynucleotide sequence used in Example 7. This sequence has a 5' cholesterol TEG.

SEQ ID NO: 32 shows a polynucleotide sequence used in Example 6. Attached to the 5' end of SEQ ID NO: 32 is 39 SpC3 spacers. Attached to the 3' end of SEQ ID NO: 32 is four iSP18 spacers which are attached at the opposite end to the 5' end of SEQ ID NO: 33.

SEQ ID NO: 33 shows a polynucleotide sequence used in Example 6. Attached to the 5' end of SEQ ID NO: 33 is four iSP18 spacers which are attached at the opposite end to the 3' end of SEQ ID NO: 32.

SEQ ID NO: 34 shows a polynucleotide sequence used in Example 6. Attached to the 3' end is one iBNA-meC, two iBNA-A and two iBNA-meC which are attached at the opposite end to three iSp18 spacers which are attached to 5' end of SEQ ID NO: 35.

SEQ ID NO: 35 shows a polynucleotide sequence used in Example 6. Attached to the 5' end is three iSp18 spacers which are attached at the opposite end to two iBNA-meC, two iBNA-A and one iBNA-meC which is attached at the opposite end to the 3' end of SEQ ID NO: 34.

SEQ ID NO: 36 shows a polynucleotide sequence used in Example 6. Attached to the 5' end of SEQ ID NO: 36 is a phosphate. Attached to the 3' end of SEQ ID NO: 36 is four iSp18 spacers which are attached to the opposite end to the 5' end of SEQ ID NO 37.

SEQ ID NO: 37 shows a polynucleotide sequence used in Example 6. Attached to the 5' end of SEQ ID NO: 37 is four iSp18 spacers which are attached to the opposite end to the 3' end of SEQ ID NO: 36.

SEQ ID NO: 38 shows a polynucleotide sequence used in Example 6.

SEQ ID NO: 39 shows a polynucleotide sequence used in Example 6. Attached to the 5' end of SEQ ID NO: 39 is a phosphate. Attached to the 3' end of SEQ ID NO: 39 is four iSpC3 spacers which are attached at the opposite end to the 5' end of SEQ ID NO: 40.

SEQ ID NO: 40 shows a polynucleotide sequence used in Example 6. Attached to the 5' end of SEQ ID NO: 40 is four iSpC3 which are attached at the opposite end to the 3' end of SEQ ID NO: 39.

SEQ ID NO: 41 shows a polynucleotide sequence used in Example 6. SEQ ID NO: 41 is complementary to SEQ ID NO: 42.

SEQ ID NO: 42 shows a polynucleotide sequence used in Example 6. SEQ ID NO: 42 is complementary to SEQ ID NO: 41.

SEQ ID NO: 43 shows a polynucleotide sequence used in Example 7.

SEQ ID NO: 44 shows a polynucleotide sequence used in Example 7. This sequence has a 5' phosphate. The 3' end of SEQ ID NO: 44 is attached to four iSpC3 spacers which are attached at the opposite end to the 5' end of SEQ ID NO: 45.

SEQ ID NO: 45 shows a polynucleotide sequence used in Example 7. This sequence is attached at its 5' end to four iSpC3 spacers which are attached at the opposite end to the 3' end of SEQ ID NO: 44.

SEQ ID NO: 46 shows a polynucleotide sequence used in Example 7.

SEQ ID NO: 47 shows a polynucleotide sequence used in Example 7. This sequence has a 5' phosphate and a thymine based phosphorothioate base at the 3' end of the sequence.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polynucleotide" includes two or more polynucleotides, reference to "an enzyme" includes two or more enzymes, reference to "a helicase" includes two or more helicases, reference to "a molecular brake" refers to two or more molecular brakes, reference to "a transmembrane pore" includes two or more pores and the like.

All publications, patents and patent applications cited herein, whether supra or infra, are hereby incorporated by reference in their entirety.

Method of the Invention

The invention provides a method of attaching one or more polynucleotide binding proteins to a target polynucleotide. The one or more polynucleotide binding proteins are provided bound to (or attached to) one or more loading moieties. The one or more loading moieties are attached to the target polynucleotide. This attaches the one or more polynucleotide binding proteins to the target polynucleotide. Once the one or more polynucleotide binding proteins have been attached in this way, they can be used to control the movement of the target polynucleotide through a transmembrane pore or form one or more polynucleotides using the target polynucleotide as a template (i.e. modify the target polynucleotide). This allows the target polynucleotide to be characterised as discussed in more detail below.

The invention has various advantages.

i. Pre-loading the polynucleotide binding proteins on the loading moieties speeds up the sample preparation process and means fewer tubes are used.
ii. As close to 100% as possible of the instances of the resulting target polynucleotide have polynucleotide binding proteins attached. This can improved yields of subsequent requisite processes.
iii. Customer error is reduced if they do not load the one or more polynucleotide binding proteins onto the one or more loading moieties.
iv. No excess polynucleotide binding protein (which could block the pore or have some other unwanted activity) remains after attachment.
v. Stability of the one or more polynucleotide binding proteins is improved. A protein bound to a polynucleotide is likely to be more stable.
vi. The excess loading moieties can act as a control for the system being set up correctly (i.e. is the ATP in the buffer etc).
vii. The user can control the order of the one or more polynucleotide binding proteins so that they are loaded in the correct sequence on one loading moiety.
viii. The user can control which polynucleotide binding proteins are attached to which loading moiety, e.g. Y adaptor versus bridging moiety.
ix. The one or more polynucleotide binding proteins can be used to purify the one or more loading moieties.
x. The user can make different modifications to the polynucleotide binding proteins attached to different loading moieties.
xi. Different polynucleotide binding proteins may prefer different binding conditions and so it may helpful to be able to pre-load them on different loading moieties (rather than together on the target polynucleotide).
xii If the one or more polynucleotide binding proteins are pre-loaded, there should not be any free polynucleotide binding proteins after attachment and so the proteins can be used to purify the construct.
xiii The invention minimises use of the one or more polynucleotide binding proteins and so there is less wastage.
xiv The user can control where the one or more polynucleotide binding proteins bind or do not bind with respect to the target polynucleotide. By pre-loading the one or more polynucleotide binding proteins on the one or more loading moieties, the one or more polynucleotide binding proteins do not bind directly to the target polynucleotide.
xv The invention also improves the yield of sequence information, eg. when a polymerase copys the target strand. Yields can be limited by inefficient protein binding, and also lack of processivity. Preloading overcomes loading inefficiencies, and creating a closed-complex overcomes processivity problems.

The invention also provides a method of characterising a target polynucleotide. Once the one or more polynucleotide binding proteins have been loaded onto the target polynucleotide, they can be contacted with a transmembrane pore such that the one or more polynucleotide binding proteins control the movement of the polynucleotide with respect to the pore, such as through the pore. The method also comprises taking one or more measurements as the polynucleotide moves with respect to the pore. The measurements are indicative of one or more characteristics of the polynucleotide, such as the sequence.

It has been shown that double stranded polynucleotides can be effectively characterised using a transmembrane pore if they are modified to include a Y adaptor (a double stranded stem and two non-complementary arms) containing a leader sequence and a bridging moiety adaptor, such as a hairpin loop adaptor (WO 2013/014451). It is preferred that that Y adaptor containing the leader sequence is attached to one end of the polynucleotide and the bridging moiety adaptor is attached to the other end. The leader sequence preferentially threads into the nanopore and the bridging moiety (such as a hairpin loop) connecting the two strands of the polynucleotide allows both strands to be investigated as the polynucleotide unzips and both strands (connected via the bridging moiety) move with respect to the pore, such as through the pore. This is advantageous because it doubles the amount of information obtained from a single double-stranded polynucleotide. Moreover, because the sequences in the two strands are complementary, the information from the two strands can be combined informatically. This mechanism provides an orthogonal proof-reading capability that provides higher confidence observations. The one or more loading moieties used in accordance with the invention may be the Y adaptor and/or the bridging moiety adaptor. This is discussed in more detail below.

The invention also provides method of preparing a target polynucleotide for characterisation. The method may be for improving the target polynucleotide for characterisation. The method may be for modifying or extending the target polynucleotide. Once one or more polymerases have been loaded onto the target polynucleotide, they can be allowed to form one or more polynucleotides using the target polynucleotide as a template. If the target polynucleotide is single stranded, another complementary polynucleotide is formed. If the target polynucleotide is double stranded, both strands are preferably used as templates by the one or more polymerases. Because the strand(s) from the target polynucleotide and the new polynucleotide(s) produced by the one or more polymerases are complementary, the information from them can be combined informatically as discussed above. This type of method is also disclosed in WO 2013/014451. The polynucleotide(s) formed by the polymerase may comprise the same type of polynucleotide as the target polynucleotide or a different type of polynucleotide as discussed in more detail below. The target polynucleotide may be modified as discussed in more detail below. The one or more polymerases may be loaded onto the target polynucleotide using a Y adaptor and/or a bridging moiety adaptor as discussed in more detail below.

Polynucleotide

The target polynucleotide may be any polynucleotide. A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidized or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below. The polynucleotide may comprise one or more spacers.

A nucleotide typically contains a nucleobase, a sugar and at least one phosphate group. The nucleobase and sugar form a nucleoside. The nucleotide may be a natural nucleotide or a non-natural nucleotide.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The nucleotide in the polynucleotide is typically a ribonucleotide or deoxyribonucleotide. The polynucleotide may comprise the following nucleosides: adenosine, uridine, guanosine and cytidine. The nucleotide is preferably a deoxyribonucleotide. The polynucleotide preferably comprises the following nucleosides: deoxyadenosine (dA), deoxyuridine (dU) and/or thymidine (dT), deoxyguanosine (dG) and deoxycytidine (dC).

The nucleotide typically contains a monophosphate, diphosphate or triphosphate. Phosphates may be attached on the 5' or 3' side of a nucleotide.

Suitable nucleotides include, but are not limited to, adenosine monophosphate (AMP), guanosine monophosphate (GMP), thymidine monophosphate (TMP), uridine monophosphate (UMP), cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP. The nucleotides are most preferably selected from dAMP, dTMP, dGMP, dCMP and dUMP. The polynucleotide preferably comprises the following nucleotides: dAMP, dUMP and/or dTMP, dGMP and dCMP.

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid. The polynucleotide may be any synthetic nucleic acid known in the art, such as peptide nucleic acid (PNA), glycerol nucleic acid (GNA), threose nucleic acid (TNA), locked nucleic acid (LNA), bridged nucleic acid (BNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety. Bridged nucleic acids (BNAs) are modified RNA nucleotides. They may also be called constrained or inaccessible RNA. BNA monomers can contain a five-membered, six-membered or even a seven-membered bridged structure with a "fixed" C3'-endo sugar puckering. The bridge is synthetically incorporated at the 2', 4'-position of the ribose to produce a 2', 4'-BNA monomer.

The polynucleotide is most preferably ribonucleic nucleic acid (RNA) or deoxyribonucleic acid (DNA).

The polynucleotide may be any length. For example, the polynucleotide can be at least 10, at least 50, at least 100, at least 150, at least 200, at least 250, at least 300, at least 400 or at least 500 nucleotides in length. The polynucleotide can be 1000 or more nucleotides, 5000 or more nucleotides in length or 100000 or more nucleotides in length.

The helicase may move along the whole or only part of the polynucleotide in the method of the invention. The whole or only part of the target polynucleotide may be characterised using the method of the invention.

The polynucleotide may be single stranded. At least a portion of the polynucleotide is preferably double stranded. Helicases typically bind to single stranded polynucleotides. If at least a portion of the polynucleotide is double stranded, the polynucleotide preferably comprises a single stranded region or a non-hybridised region. The one or more helicases are capable of binding to the single stranded region or one strand of the non-hybridised region. The polynucleotide preferably comprises one or more single stranded regions or one or more non-hybridised regions.

The one or more spacers are preferably included in the single stranded region or the non-hybridised region of the polynucleotide. The polynucleotide may comprise more than one single stranded region or more than one non-hybridised region. The polynucleotide may comprise a single stranded region or a non-hybridised region within its sequence and/or at one or both ends. The one or more spacers may be included in the double stranded region of the polynucleotide.

If the one or more helicases used in the method move in the 5' to 3' direction, the polynucleotide preferably comprises a single stranded region or a non-hybridised region at its 5' end. If the one or more helicases used in the method move in the 3' to 5' direction, the polynucleotide preferably comprises a single stranded region or a non-hybridised region at its 3' end. If the one or more helicases are used in the inactive mode (i.e. as a brake), it does not matter where the single stranded region or the non-hybridised region is located.

The single stranded region preferably comprises a leader sequence which preferentially threads into the pore. This is discussed in more detail below.

If at least a portion of the polynucleotide is double stranded, the two strands of the double stranded portion are preferably linked using a bridging moiety, such as a hairpin or a hairpin loop. This facilitates characterisation method of the invention and is discussed in more detail below.

The polynucleotide is present in any suitable sample. The invention is typically carried out on a sample that is known to contain or suspected to contain the polynucleotide. The invention may be carried out on a sample to confirm the identity of one or more polynucleotides whose presence in the sample is known or expected.

The sample may be a biological sample. The invention may be carried out in vitro on a sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep, fish, chickens or pigs or may alternatively be pets such as cats or dogs. Alternatively, the sample may be of plant origin, such as a sample obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being used in the invention, for example by centrifugation or by passage through a membrane that filters out unwanted molecules or cells, such as red blood cells. The sample may be measured immediately upon being taken. The sample may also be typically stored prior to assay, preferably below −70° C.

Polynucleotide Binding Proteins

A polynucleotide binding protein may be any protein that is capable of binding to the polynucleotide and controlling its movement with respect to the pore, such as through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

Any number of polynucleotide proteins may be attached to the target polynucleotide. For instance, 1, 2, 3, 4, 5, 6, 7, 8, 9, 10 or more proteins may be attached.

The one or more polynucleotide binding proteins may be one or more single stranded binding proteins (SSBs). The one or more single-stranded binding proteins (SSBs) may comprise a carboxy-terminal (C-terminal) region which does not have a net negative charge or (ii) a modified SSB comprising one or more modifications in its C-terminal region which decreases the net negative charge of the C-terminal region. The one or more polynucleotide binding proteins may be any of the SSBs disclosed in International Application No. PCT/GB2013/051924 (published as WO 2014/013259).

The one or more polynucleotide binding proteins are preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement with respect to the pore, such as through the pore. For instance, the enzyme may be modified to remove its enzymatic activity or may be used under conditions which prevent it from acting as an enzyme. Such conditions are discussed in more detail below.

The one or more polynucleotide binding proteins are preferably derived from a nucleolytic enzyme. The enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases, and reverse transcriptases. Suitable enzymes include, but are not limited to, exonuclease I from *E. coli* (SEQ ID NO: 11), exonuclease III enzyme from *E. coli* (SEQ ID NO: 13), RecJ from *T. thermophilus* (SEQ ID NO: 15) and bacteriophage lambda exonuclease (SEQ ID NO: 17), TatD exonuclease and variants thereof. Three subunits comprising the sequence shown in SEQ ID NO: 15 or a variant thereof interact to form a trimer exonuclease. The polymerase may be PyroPhage® 3173 DNA Polymerase (which is commercially available from Lucigen® Corporation), SD Polymerase (commercially available from Bioron®), Klenow from NEB or variants thereof. The enzyme is preferably Phi29 DNA polymerase (SEQ ID NO: 9) or a variant thereof. Preferred versions of Phi29 are discussed in more detail below. Modified versions of Phi29 polymerase that may be used in the invention are discussed below and disclosed in U.S. Pat. No. 5,576,204. The topoisomerase is preferably a member of any of the Moiety Classification (EC) groups 5.99.1.2 and 5.99.1.3. Reverse transcriptases are enzymes which are capable of catalysing the formation of cDNA from a RNA template. They are commercially available from, for instance, New England Biolabs® and Invitrogen®.

The one or more polynucleotide binding proteins are preferably derived from a helicase. Helicases can control the movement of polynucleotides in at least two active modes of operation (when the helicase is provided with all the necessary components to facilitate movement, e.g. ATP and $Mg^{2+}$) and one inactive mode of operation (when the helicase is not provided with the necessary components to facilitate movement or is modified to prevent or hinder movement). When provided with all the necessary components to facilitate movement, the helicase moves along the polynucleotide in a 5' to 3' or a 3' to 5' direction (depending on the helicase), but the orientation of the polynucleotide in the pore (which is dependent on which end of the polynucleotide is captured by the pore) means that the helicase can be used to either move the polynucleotide out of the pore against the applied field or move the polynucleotide into the pore with the applied field. When the end of the polynucleotide towards which the helicase moves is captured by the pore, the helicase works against the direction of the field resulting from the applied potential and pulls the threaded polynucleotide out of the pore and into the cis chamber. However, when the end away from which the helicase moves is captured in the pore, the helicase works with the direction of the field resulting from the applied potential and pushes the threaded polynucleotide into the pore and into the trans chamber.

When the helicase is not provided with the necessary components to facilitate movement it can bind to the polynucleotide and act as a brake slowing the movement of the polynucleotide when it is pulled into the pore by the field resulting from the applied potential. In the inactive mode, it does not matter which end of the polynucleotide is captured, it is the applied field which pulls the polynucleotide into the pore towards the trans side with the helicase acting as a brake. When in the inactive mode, the movement control of the polynucleotide by the helicase can be described in a number of ways including ratcheting, sliding and braking.

In the characterization method of the invention, the one or more helicases preferably control the movement of the target polynucleotide with respect to the pore, such as through the pore, with the field resulting from the applied potential. In one preferred embodiment, the one or more helicases are used in the active mode and the end away from which the one or more helicases move is captured by the pore such that the one or more helicases work with the field resulting from the applied potential and push the polynucleotide with respect to the pore, such as through the pore. If the one or more helicases move in the 5' to 3' direction, the 5' end of the polynucleotide is preferably captured by the pore. In such embodiments, the one or more helicases move along the polynucleotide in the 5' to 3' direction. If the one or more helicases move in the 3' to 5' direction, the 3' end of the polynucleotide is preferably captured by the pore. In such embodiments, the one or more helicases move along the polynucleotide in the 3' to 5' direction.

In another preferred embodiment of the characterization method, the one or more helicases are used in the inactive mode such that the applied field pulls the polynucleotide with respect to the pore, such as through the pore, and the one or more helicases act as a brake. In another preferred embodiment, the one or more helicases are modified such that they retain their polynucleotide binding ability but lack helicase activity (i.e. the ability to actively move along the polynucleotide) such that the applied field pulls the polynucleotide with respect to the pore, such as through the pore, and the one or more helicases act as a brake. In the method of the invention, the one or more helicases preferably slow or brake the movement of the polynucleotide with respect to the pore, such as through the pore, with the field resulting from the applied potential. In either case, the one or more helicases are typically too large to move with respect to the pore, such as through the pore, and the pore pushes the one or more helicases along the polynucleotide as the polynucleotide moves with respect to the pore, such as through the pore, with the field resulting from the applied potential.

Any steps in the characterization method using one or more helicases are typically carried out in the presence of free nucleotides or free nucleotide analogues and an enzyme cofactor that facilitates the action of the one or more helicases. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferablygm $Mg^{2+}$, $Mn^{2+}$, $Ca^{2+}$ or $Co^{2+}$. The enzyme cofactor is most preferably $Mg^{2+}$.

Any helicase may be used in the invention. The helicase may be or be derived from a Hel308 helicase, a RecD helicase, such as TraI helicase or a TrwC helicase, a XPD helicase or a Dda helicase. The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925 (published as WO 2014/013260); PCT/GB2013/051924 (published as WO 2014/013259) and PCT/GB2013/051928 (published as WO 2014/013262); and in International Application No. PCT/GB2014/052736.

The one or more polynucleotide binding proteins may be derived from a helicase, such as Hel308 Mbu (SEQ ID NO: 18), Hel308 Csy (SEQ ID NO: 19), Hel308 Tga (SEQ ID NO: 20), Hel308 Mhu (SEQ ID NO: 21), TraI Eco (SEQ ID NO: 22), XPD Mbu (SEQ ID NO: 23) or a variant thereof. The one or more polynucleotide binding proteins preferably comprise the sequence shown in SEQ ID NO: 25 (Trwc Cba) or a variant thereof, the sequence shown in SEQ ID NO: 18 (Hel308 Mbu) or a variant thereof or the sequence shown in SEQ ID NO: 24 (Dda) or a variant thereof. Variants may differ from the native sequences in any of the ways discussed below for helicases or transmembrane pores.

A preferred variant of SEQ ID NO: 24 comprises (or only comprises) (a) E94C/A360C, (b) E94C/A360C and then (ΔM1)G1G2 (i.e. deletion of M1 and then addition G1 and G2), (c) E94C/A360C/C109A/C136A or (d) E94C/A360C/C109A/C136A and then (ΔM1)G1G2 (i.e. deletion of M1 and then addition G1 and G2).

Other preferred variants of SEQ ID NO: 24 comprise W378A. Preferred variants of SEQ ID NO: 24 comprise (or comprise only) (a) E94C/A360C/W378A, (b) E94C/A360C/W378A and then (ΔM1)G1G2 (i.e. deletion of M1 and then addition G1 and G2), (c) E94C/A360C/C109A/C136A/W378A or (d) E94C/A360C/C109A/C136A/W378A and then (ΔM1)G1G2 (i.e. deletion of M1 and then addition G1 and G2).

Preferred variants of SEQ ID NO: 25 comprises (or only comprises) (a) Q594A, (b) L376C/Q594A/K762C, (c) L376C/Q594A/A779C, (d) Q346C/Q594A/A779C, (e) Q346C/Q594A/A783C, D411/Q594A/A783C, (g) Q594A/R353C/E722C, (h) Q594A/Q357C/T720C, (i) Q594A/R358C/T720C, (j) Q594A/H354C/T720C, (k) Q594A/F374C/E722C or (l) Q594A/S350C/E722C. Any of (a) to (l) may further comprise and then (ΔM1)G1G2 (i.e. deletion of M1 and then addition G1 and G2). Other Preferred variants are discussed above.

The one or more helicases are preferably modified to reduce the size of an opening in the polynucleotide binding domain through which in at least one conformational state the polynucleotide can unbind from the helicase. The one or more helicases are preferably modified to close an opening in the polynucleotide binding domain through which in at least one conformational state the polynucleotide can unbind from the helicase. This is disclosed in WO 2014/013260 and PCT/GB2014/052736. Any of the modifications disclosed in WO 2014/013260 and PCT/GB2014/052736 may be used in the invention.

The ability of a helicase to bind to and unbind from a polynucleotide can be determined using any method known in the art. Suitable binding/unbinding assays include, but are not limited to, native polyacrylamide gel electrophoresis (PAGE), fluorescence anisotropy, calorimetry and Surface plasmon resonance (SPR, such as Biacore™). The ability of a helicase to unbind from a polynucleotide can of course be determined by measuring the time for which the helicase can control the movement of a polynucleotide. This may also be determined using any method known in the art. The ability of a helicase to control the movement of a polynucleotide is typically assayed in a nanopore system, such as the ones described below. The ability of a helicase to control the movement of a polynucleotide can be determined as described in the Examples.

As disclosed in PCT/GB2014/052736, a helicase used in the invention may be a Dda helicase in which at least one cysteine residue and/or at least one non-natural amino acid have been introduced into the hook domain and/or the 2A (RecA-like motor) domain, wherein the helicase retains its ability to control the movement of a polynucleotide. Any number of cysteine residues and/or non-natural amino acids may be introduced into each domain. For instance, 1, 2, 3, 4, 5, 6, 7, 8, 9, 10 or more cysteine residues may be introduced and/or 1, 2, 3, 4, 5, 6, 7, 8, 9, 10 or more non-natural amino acids may be introduced. Only one or more cysteine residues may be introduced. Only one or more non-natural amino acids may be introduced. A combination of one or more cysteine residues and one or more non-natural amino acids may be introduced. The at least one cysteine residue and/or at least one non-natural amino acid are/is preferably introduced by substitution. Methods for doing this are known in the art. These Dda modifications do not prevent the helicase from binding to a polynucleotide. These modifications decrease the ability of the polynucleotide to unbind or disengage from the helicase. In other words, the one or more modifications increase the processivity of the Dda helicase by preventing dissociation from the polynucleotide strand. The thermal stability of the enzyme is typically also increased by the one or more modifications giving it an improved structural stability that is beneficial in Strand Sequencing. A non-natural amino acid is an amino that is not naturally found in a Dda helicase. The non-natural amino acid is preferably not histidine, alanine, isoleucine, arginine, leucine, asparagine, lysine, aspartic acid, methionine, cysteine, phenylalanine, glutamic acid, threonine, glutamine, tryptophan, glycine, valine, proline, serine or tyrosine. The non-natural amino acid is more preferably not any of the twenty amino acids in the previous sentence or selenocysteine Preferred non-natural amino acids for use in the invention include, but are not limited, to 4-Azido-L-phenylalanine (Faz), 4-Acetyl-L-phenylalanine, 3-Acetyl-L-phenylalanine, 4-Acetoacetyl-L-phenylalanine, O-Allyl-L-tyrosine, 3-(Phenylselanyl)-L-alanine, O-2-Propyn-1-yl-L-tyrosine, 4-(Dihydroxyboryl)-L-phenylalanine, 4-[(Ethylsulfanyl)carbonyl]-L-phenylalanine, (2S)-2-amino-3-{4-[(propan-2-ylsulfanyl)carbonyl]phenyl}propanoic acid, (2S)-2-amino-3-{4-[(2-amino-3-sulfanylpropanoyl)amino]phenyl}propanoic acid, O-Methyl-L-tyrosine, 4-Amino-L-phenylalanine, 4-Cyano-L-phenylalanine, 3-Cyano-L-phenylalanine, 4-Fluoro-L-phenylalanine, 4-Iodo-L-phenylalanine, 4-Bromo-L-phenylalanine, O-(Trifluoromethyl)tyrosine, 4-Nitro-L-phenylalanine, 3-Hydroxy-L-tyrosine, 3-Amino-L-tyrosine, 3-Iodo-L-tyrosine, 4-Isopropyl-L-phenylalanine, 3-(2-Naphthyl)-L-alanine, 4-Phenyl-L-phenylalanine, (2S)-2-amino-3-(naphthalen-2-ylamino)propanoic acid, 6-(Methylsulfanyl)norleucine, 6-Oxo-L-lysine, D-tyrosine, (2R)-2-Hydroxy-3-(4-hydroxyphenyl)propanoic acid, (2R)-2-Ammoniooctanoate3-(2,2'-Bipyridin-5-yl)-D-alanine, 2-amino-3-(8-hydroxy-3-quinolyl)propanoic acid, 4-Benzoyl-L-phenylalanine, S-(2-Nitrobenzyl)cysteine, (2R)-2-amino-3-[(2-nitrobenzyl)sulfanyl]propanoic acid, (2S)-2-amino-3-[(2-nitrobenzyl)oxy]propanoic acid, O-(4,5-Dimethoxy-2-nitrobenzyl)-L-serine, (2S)-2-amino-6-({[(2-nitrobenzyl)oxy]carbonyl}amino)hexanoic acid, O-(2-Nitrobenzyl)-L-tyrosine, 2-Nitrophenylalanine, 4-[(E)-Phenyldiazenyl]-L-phenylalanine, 4-[3-(Trifluoromethyl)-3H-diaziren-3-yl]-D-phenylalanine, 2-amino-3-[[5-(dimethylamino)-1-naphthyl]sulfonylamino]propanoic acid, (2S)-2-amino-4-(7-hydroxy-2-oxo-2H-chromen-4-yl)butanoic acid, (2S)-3-[(6-acetylnaphthalen-2-yl)amino]-2-aminopropanoic acid, 4-(Carboxymethyl)phenylalanine, 3-Nitro-L-tyrosine, O-Sulfo-L-tyrosine, (2R)-6-Acetamido-2-ammoniohexanoate, 1-Methylhistidine, 2-Aminononanoic acid, 2-Aminodecanoic acid, L-Homocysteine, 5-Sulfanylnorvaline, 6-Sulfanyl-L-norleucine, 5-(Methylsulfanyl)-L-norvaline, $N^6$-{[(2R,3R)-3-Methyl-3,4-dihydro-2H-pyrrol-2-yl]carbonyl}-L-lysine, $N^6$-[(Benzyloxy)carbonyl]lysine, (2S)-2-amino-6-[(cyclopentylcarbonyl)amino]hexanoic acid, $N^6$-[(Cyclopentyloxy)carbonyl]-L-lysine, (2S)-2-amino-6-{[(2R)-tetrahydrofuran-2-ylcarbonyl]amino}hexanoic acid, (2S)-2-amino-8-[(2R,3S)-3-ethynyltetrahydrofuran-2-yl]-8-oxooctanoic acid, $N^6$-(tert-Butoxycarbonyl)-L-lysine, (2S)-2-Hydroxy-6-({[(2-methyl-2-propanyl)oxy]carbonyl}amino)hexanoic acid, $N^6$-[(Allyloxy)carbonyl]lysine, (2S)-2-amino-6-({[(2-azidobenzyl)oxy]carbonyl}amino)hexanoic acid, $N^6$-L-Prolyl-L-lysine, (2S)-2-amino-6-{[(prop-2-yn-1-yloxy)carbonyl]amino}hexanoic acid and $N^6$-[(2-Azidoethoxy)carbonyl]-L-lysine. The most preferred non-natural amino acid is 4-azido-L-phenylalanine (Faz).

The helicase used in the invention preferably comprises a variant of SEQ ID NO: 24 in which at least one cysteine residue and/or at least one non-natural amino acid have been introduced into (i) the tower domain (residues D260-P274 and N292-A389) and/or (ii) the pin domain (residues K86-E102) and/or the (iii) 1A domain (residues M1-L85 and V103-K177). The at least one cysteine residue and/or at least one non-natural amino acid are preferably introduced into residues N292-A389 of the tower domain.

The introductions of at least two cysteines into SEQ ID NOs: 24 and 25 as discussed above reduces the size of or closes an opening in the polynucleotide binding domain of the helicases.

Preferred helicase constructs for use in the invention are described in International Application Nos. PCT/GB2013/051925 (published as WO 2014/013260); PCT/GB2013/051924 (published as WO 2014/013259) and PCT/GB2013/051928 (published as WO 2014/013262); and in UK Application No. 1318464.3 filed on 18 Oct. 2013.

A variant of SEQ ID NOs: 9, 11, 13, 15, 17, 18, 19, 20, 21, 22, 23, 24 or 25 is an enzyme that has an amino acid sequence which varies from that of SEQ ID NO: 9, 11, 13, 15, 17, 18, 19, 20, 21, 22, 23, 24 or 25 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature. Variants may be modified such that they bind polynucleotides (i.e. retain polynucleotide binding ability) but do not function as an enzyme. For instance, variants of helicases may be modified such that they bind polynucleotides (i.e. retain polynucleotide binding ability) but do not function as a helicase (i.e. do not move along polynucleotides when provided with all the necessary components to facilitate movement, e.g. ATP and $Mg^{2-}$). Such modifications are known in the art. For instance, modification of the $Mg^{2+}$ binding domain in helicases typically results in variants which do not function as helicases. These types of variants may act as molecular brakes. A preferred molecular brake is TrwC Cba-Q594A (SEQ ID NO: 25 with the mutation Q594A). Others are discussed above with reference to SEQ ID NO: 25. This variant does not function as a helicase (i.e. binds to polynucleotides but does not move along them when provided with all the necessary components to facilitate movement, e.g. ATP and $Mg^{2+}$). The one or more molecular brake helicases can be used in any direction and/or mode discussed above.

Over the entire length of the amino acid sequence of SEQ ID NO: 9, 11, 13, 15, 17, 18, 19, 20, 21, 22, 23, 24 or 25, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 9, 11, 13, 15, 17, 18, 19, 20, 21, 22, 23, 24 or 25 over the entire sequence. There may be at least 80%, for example at least 85%, 90% or 95%, amino acid identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and 4 below.

If two or more polynucleotide binding proteins are used, they may be the same or different. Any combination of the proteins discussed above may be used. For instance, the two or more proteins may be different variants of the same protein, such as helicase. The two or more polynucleotide binding proteins preferably comprise one or more helicases and one or more polymerases.

If two or more polynucleotide binding proteins are used, they may be attached to one another. The two or more polynucleotide binding proteins may be covalently attached to one another. The polynucleotide binding proteins may be attached in any order and using any method. Preferred helicase constructs for use in the invention are described in International Application Nos. PCT/GB2013/051925 (published as WO 2014/013260); PCT/GB2013/051924 (published as WO 2014/013259) and PCT/GB2013/051928 (published as WO 2014/013262); and in UK Application No. 1318464.3 filed on 18 Oct. 2013.

If two or more polynucleotide binding proteins are used, they are preferably not attached to one another except via the polynucleotide. The two or more polynucleotide binding proteins are more preferably not covalently attached to one another.

One or More Helicases and One or More Molecular Brakes

In some instances the characterisation method of the invention may concern using one or more helicases and one or more molecular brakes. When the target polynucleotide is contacted with the pore, the one or more helicases and the one or more molecular brakes are brought together and both control the movement of the polynucleotide with respect to the pore, such as through the pore.

The one or more helicases may be any of those discussed above. The one or more molecular brakes may be any compound or molecule which binds to the polynucleotide and slows the movement of the polynucleotide with respect to the pore, such as through the pore. The one or more molecular brakes preferably comprise one or more compounds which bind to the polynucleotide. The one or more compounds are preferably one or more macrocycles. Suitable macrocycles include, but are not limited to, cyclodextrins, calixarenes, cyclic peptides, crown ethers, cucurbiturils, pillararenes, derivatives thereof or a combination thereof. The cyclodextrin or derivative thereof may be any of those disclosed in Eliseev, A. V., and Schneider, H-J. (1994) *J. Am. Chem. Soc.* 116, 6081-6088. The agent is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD).

The one or more molecular brakes are preferably one or more single stranded binding proteins (SSB). The one or more molecular brakes are more preferably a single-stranded binding protein (SSB) comprising a carboxy-terminal (C-terminal) region which does not have a net negative charge or (ii) a modified SSB comprising one or more modifications in its C-terminal region which decreases the net negative charge of the C-terminal region. The one or more molecular brakes are most preferably any of the SSBs disclosed in International Application No. PCT/GB2013/051924 (published as WO 2014/013259).

The one or more molecular brakes are preferably one or more polynucleotide binding proteins. The polynucleotide binding protein may be any protein that is capable of binding to the polynucleotide and controlling its movement with respect to the pore, such as through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. The one or more molecular brakes may be derived from any of the polynucleotide handling enzymes discussed above. Modified versions of Phi29 polymerase (SEQ ID NO: 9) which act as molecular brakes are disclosed in U.S. Pat. No. 5,576,204. Modified versions of Phi29 polymerase (SEQ ID NO: 9) which act as molecular brakes are disclosed below. The one or more molecular brakes are preferably derived from a helicase.

Any number of molecular brakes derived from a helicase may be used. For instance, 1, 2, 3, 4, 5, 6, 7, 8, 9, 10 or more helicases may be used as molecular brakes. If two or more helicases are be used as molecular brakes, the two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. The one or more molecular brakes derived from helicases are preferably modified to reduce the size of an opening in the polynucleotide binding domain through which in at least one conformational state the polynucleotide can unbind from the helicase. This is disclosed in WO 2014/013260.

Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736.

If the one or more helicases are used in the active mode (i.e. when the one or more helicases are provided with all the necessary components to facilitate movement, e.g. ATP and $Mg^{2+}$), the one or more molecular brakes are preferably (a) used in an inactive mode (i.e. are used in the absence of the necessary components to facilitate movement or are incapable of active movement), (b) used in an active mode where the one or more molecular brakes move in the opposite direction to the one or more helicases or (c) used in an active mode where the one or more molecular brakes move in the same direction as the one or more helicases and more slowly than the one or more helicases.

If the one or more helicases are used in the inactive mode (i.e. when the one or more helicases are not provided with all the necessary components to facilitate movement, e.g. ATP and $Mg^{2+}$ or are incapable of active movement), the one or more molecular brakes are preferably (a) used in an inactive mode (i.e. are used in the absence of the necessary components to facilitate movement or are incapable of active movement) or (b) used in an active mode where the one or more molecular brakes move along the polynucleotide in the same direction as the polynucleotide with respect to the pore, such as through the pore.

The one or more helicases and one or more molecular brakes may be attached to the polynucleotide at any positions so that they are brought together and both control the movement of the polynucleotide with respect to the pore, such as through the pore. The one or more helicases and one or more molecular brakes are at least one nucleotide apart, such as at least 5, at least 10, at least 50, at least 100, at least 500, at least 1000, at least 5000, at least 10,000, at least 50,000 nucleotides or more apart. If the method concerns characterising a double stranded polynucleotide provided with a Y adaptor at one end and a bridging moiety adaptor, such as a hairpin loop adaptor, at the other end, the one or more helicases are preferably attached to the Y adaptor and the one or more molecular brakes are preferably attached to the bridging moiety adaptor. In this embodiment, the one or more molecular brakes are preferably one or more helicases that are modified such that they bind the polynucleotide but do not function as a helicase. The one or more helicases attached to the Y adaptor are preferably stalled at a spacer as discussed in more detail below. The one or more molecular brakes attached to the bridging moiety adaptor are preferably not stalled at a spacer. The one or more helicases and the one or more molecular brakes are preferably brought together when the one or more helicases reach the bridging moiety. The one or more helicases may be attached to the Y adaptor before the Y adaptor is attached to the polynucleotide or after the Y adaptor is attached to the polynucleotide. The one or more molecular brakes may be attached to the bridging moiety adaptor before the bridging moiety adaptor is attached to the polynucleotide or after the bridging moiety adaptor is attached to the polynucleotide.

The one or more helicases and the one or more molecular brakes are preferably not attached to one another. The one or more helicases and the one or more molecular brakes are more preferably not covalently attached to one another. The one or more helicases and the one or more molecular brakes are preferably not attached as described in International Application Nos. PCT/GB2013/051925 (published as WO 2014/013260); PCT/GB2013/051924 (published as WO 2014/013259) and PCT/GB2013/051928 (published as WO 2014/013262); and in UK Application No. 1318464.3 filed on 18 Oct. 2013.

One or More Polymerases

The method of the invention preferably concerns attaching one or more polymerases to the target polynucleotide. Any of the polymerases discussed above or below may be used. For instance, the polymerase may comprise the sequence shown in SEQ ID NO: 9 or 31 or a variant thereof as defined above.

Preferred variants of SEQ ID NO: 9 include, but are not limited to, variants which comprise the following substitutions (a) G410C and P562C, (b) A411C and Q560C, (c) K402C and I94C, (d) A406C and E75C and (e) L412C and Q560C. The introduction of these cysteines into SEQ ID NO: 9 reduces the size of or closes an opening in the polynucleotide binding domain of the polymerase as discussed above for helicases. The variants in (a) to (e) may be used as molecular brakes as discussed above.

Once the one or more polymerases are loaded on the target polynucleotide, it/they may be allowed to form one or more polynucleotides using the target polynucleotide as a template. This typically involves contacting the target polynucleotide and the one or more polymerases with a population of free nucleotides under conditions in which the polymerase forms one or more polynucleotides using the target polynucleotide as a template. Suitable conditions are discussed below. Any number of polynucleotides may be formed by the one or more polymerases. One or two polynucleotides are preferably formed.

The population of free nucleotides may comprise any of the nucleotides discussed above and below. The nature of the one or more polynucleotides formed by the one or more polymerase will depend on the free nucleotides in the population. The one or more polymerases may form one or more polynucleotides of the same type as the target polynucleotide. For instance, if the target polynucleotide is DNA, the invention may use a population of free DNA nucleotides (i.e. nucleotides comprising deoxyadenosine, deoxyguanosine, thymidine, deoxycytidine and deoxymethylcytidine) such that the one or more polymerases form one or more DNA polynucleotides using the target polynucleotide as a template. The one or more polymerases may form one or more polynucleotides of a different type from the target polynucleotide. For instance, if the target polynucleotide is RNA, the invention may use a population of free DNA nucleotides such that the one or more polymerases form one or more DNA polynucleotides using the target polynucleotide as a template. The one or more polymerases may modify the target polynucleotide as discussed in more detail below.

A primer or a 3' hairpin is typically used as the nucleation point for polymerase extension. The one or more polymerases may be attached to the target polynucleotide in any of the ways discussed herein. The one or more polymerases are typically provided bound to one or more loading moieties, such as one or more Y adaptors and/or one or more bridging moiety adaptors (such as one or more hairpin loop adaptors).

The method of the invention preferably comprises attaching one or more polymerases to a single stranded target polynucleotide in accordance with the invention and allowing the one or more polymerases to form a polynucleotide using the target polynucleotide as a template and thereby producing a double stranded polynucleotide. The double stranded polynucleotide comprises the target polynucleotide (template) and complementary polynucleotide formed by the one or more polymerases. The two strands of the double stranded polynucleotide formed in this way may be linked with a bridging moiety adaptor, such as a hairpin loop adaptor, and both strands of the double stranded polynucleotide may be characterised as discussed below.

The invention provides a method of preparing the target polynucleotide for characterisation. The method comprises attaching one or more polymerases to the target polynucleotide using the invention and then using the one or more polymerases to produce one or more additional polynucleotides using the target polynucleotide as a template. The production of polynucleotides which complement the target polynucleotide facilitates its characterisation as discussed above.

The method preferably comprises attaching one or more polymerases to a double stranded target polynucleotide in accordance with the invention and allowing the one or more polymerases to form one or more polynucleotides using each strand of the target polynucleotide as a template.

Figure 17:
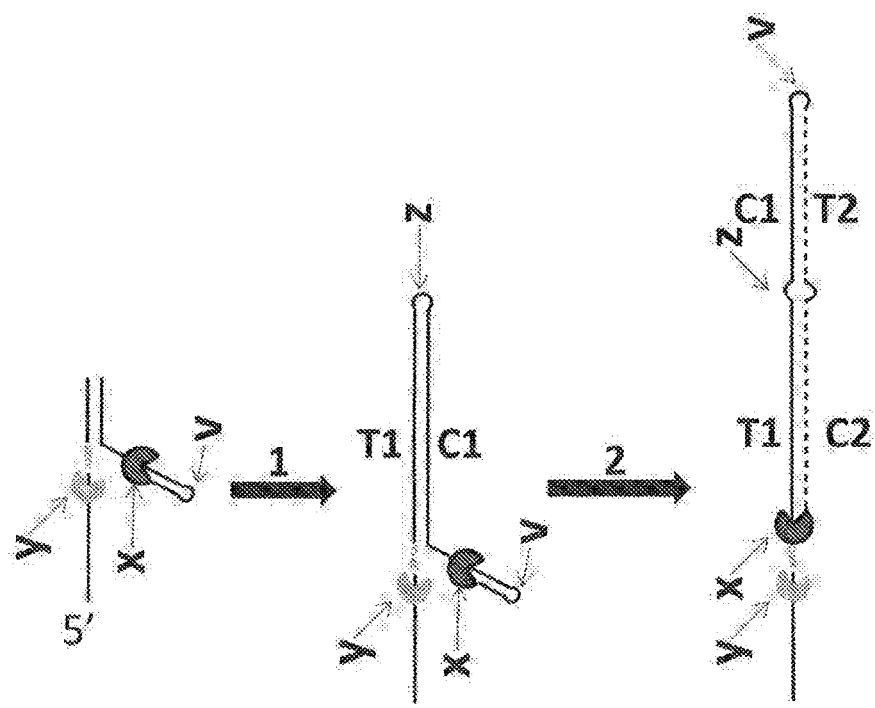
FIG. 17 shows a loading moiety, comprising a pre-bound polymerase (labelled x) and a pre-bound helicase (labelled y), which is then ligated (step 1) to the two strands of the double stranded target polynucleotide (one labelled T1 for template and the other labelled C1 for complement) which is linked at one end by a bridging moiety adaptor (labelled z). In the loading moiety the helicase is bound to the opposite strand from the strand to which the polymerase is bound. The strand to which the polymerase is bound contains a 3' hairpin loop (labelled v). In this embodiment, the polymerase will produce a double-stranded construct (step 2) in which the two strands of the construct are linked at one end by a bridging moiety (labelled v) and each strand of the construct comprises one strand of the target polynucleotide (shown as a solid line and labelled T1 and C1) and a complementary polynucleotide formed by the polymerases (shown as a dotted line and labelled T2 and C2).

In a preferred embodiment, the two strands of the double stranded target polynucleotide are linked at one end by a bridging moiety adaptor (such as a hairpin loop adaptor) and the one or more polymerases are attached to the double stranded target polynucleotide at the other end using a loading moiety comprising another bridging moiety. The loading moiety may be a Y adaptor. The other bridging moiety is typically formed by a hairpin loop at the end of the strand of the Y adaptor to which the one or more polymerases are bound. The loading moiety may comprise one or more helicases, preferably bound to the opposite strand from the strand to which the one or more polymerases are bound. In this embodiment, the one or more polymerases will produce a double stranded construct in which the two strands of the construct are linked at one end by a bridging moiety and each strand of the construct comprises one strand of the target polynucleotide and a complementary polynucleotide formed by the one or more polymerases. This is shown in FIG. 17. The two strands of the double stranded construct may be characterised as discussed below. In this embodiment, each strand of the original target polynucleotide is characterised twice. The one or polymerases may be used to control the movement of the double stranded construct with respect to the pore, such as through the pore. The one or more polymerases may be molecular brakes. If the loading moiety also comprises one or more helicases, the one or more helicases may be used to control the movement of the double stranded construct with respect to the pore, such as through the pore. In some embodiments, the one or more polymerases and the one or more helicases may both be used to control the movement of the double stranded construct with respect to the pore, such as through the pore.

Figure 18:
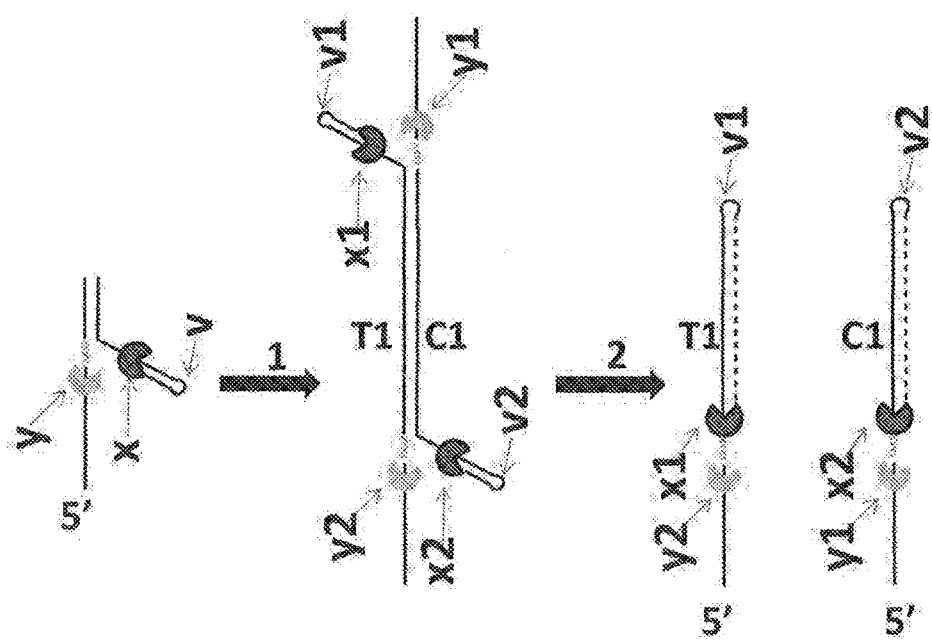
FIG. 18 shows a loading moiety comprising a pre-bound polymerase (labelled x) and a pre-bound helicase (labelled y) which is then ligated (in step 1) to each end of the two strands of the double stranded target polynucleotide, which are not linked at either end by a bridging moiety. After step 1, one end of the double stranded target polynucleotide comprises a pre-bound polymerase (labelled x1) and a pre-bound helicase (labelled y1) and the other end of the double stranded target polynucleotide comprises a pre-bound polymerase (labelled x2) and a pre-bound helicase (labelled y2). In the loading moiety the helicase is bound to the opposite strand from the strand to which the polymerase is bound. The strand to which the polymerase is bound contains a 3' hairpin loop (labelled v). In this embodiment, the polymerases will produce two double-stranded constructs (step 2) in which the two strands of each construct are linked at one end by a bridging moiety (labelled v1 or v2) and each construct comprises one strand of the target polynucleotide (shown as a solid line T1 and C1) and a complementary polynucleotide formed by the polymerases (shown as a dotted line).

In another embodiment, the two strands of the double stranded target polynucleotide are not linked at either end by a bridging moiety adaptor (such as a hairpin loop adaptor). One or more polymerases are attached to the double stranded target polynucleotide at each end using a loading moiety comprising a bridging moiety. The loading moiety at each end may be the same or different. Each loading moiety may be a Y adaptor. The bridging moiety is typically formed by a hairpin loop at the end of the strand of the Y adaptor to which the one or more polymerases are bound. The loading moieties may comprise one or more helicases, preferably bound to the opposite strand from the strand to which the one or polymerases are bound. In this embodiment, the one or more polymerases will produce two double stranded constructs in which the two strands of each construct are linked at one end by a bridging moiety and each construct comprises one strand of the target polynucleotide and a complementary polynucleotide formed by the one or more polymerases. This is shown in FIG. 18. The two constructs may be characterised as discussed below. In this embodiment, each strand of the original target polynucleotide is characterised twice, once in each construct. The one or polymerases may control the movement of each double stranded construct with respect to the pore, such as through the pore. The one or more polymerases may be molecular brakes. If each loading moiety also comprises one or more helicases, the one or more helicases may be used to control the movement of each double stranded construct with respect to the pore, such as through the pore. In some embodiments, the one or more polymerases and the one or more helicases may both be used to control the movement of each double stranded construct with respect to the pore, such as through the pore.

Figure 19:
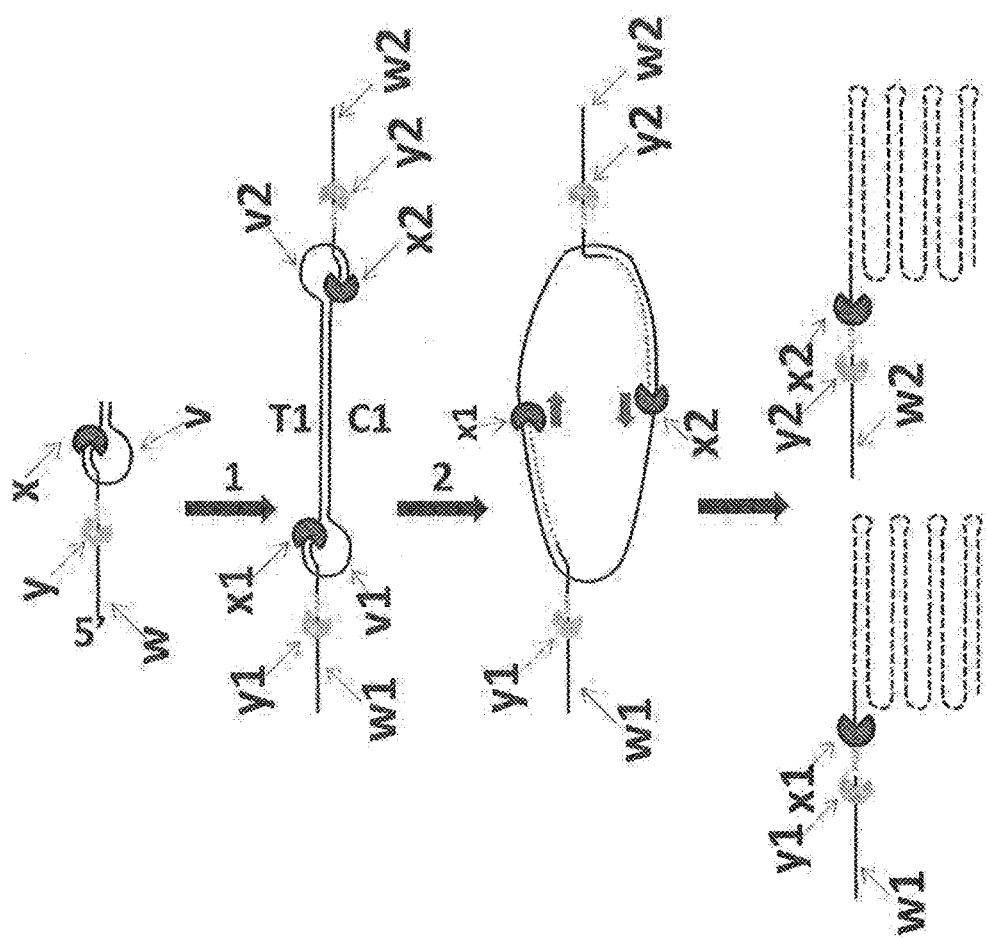
FIG. 19 shows a loading moiety (bridging moiety adaptor labelled v and hydridized leader labelled w) comprising a pre-bound polymerase (labelled x) and a pre-bound helicase (labelled y), which is then ligated (in step 1) to each end of the double stranded target polynucleotide so that they are linked at both ends by a loading moiety (labelled w1, and v1 at one end and w2, v2 at the other end, as described previously) to form a circular construct. In this example the bridging moiety adaptor comprises a polynucleotide leader (labelled w, w1 and w2) which has a helicase (labelled y, y1 and y2) pre-bound to it, which is hybridised to the bridging moiety adaptor (labelled v, v1 and v2). The double stranded section formed by the hybridisation of this polynucleotide (labelled w, w1 and w2) to the bridging adaptor moiety forms a primer site for binding the polymerase (x, x1 and x2). When polymerase extension is initiated (step 2) (e.g., by the addition of nucleotides and cofactors) two constructs will be created with DNA that is a complementary copy of the original target DNA, and will contain multiple copied sections of T1 and C1 dependent on how far the polymerase proceeds around the circular construct.

In another embodiment, the two strands of the double stranded target polynucleotide are linked at both ends by a bridiging moiety adaptor (such as a hairpin loop adaptor) to form a circular construct and one or more polymerases are attached to each bridging moiety adaptor. One or both of the bridging moiety adaptors may comprise one or more helicases, preferably bound to a polynucleotide which is hybridised to the bridging moiety adaptor. The double stranded polynucleotide formed by the hybridisation of this polynucleotide to the bridging adaptor moiety may form a nucleation for polymerase extension by the one or more polymerases. In this embodiment, the one or more polymerases at each end of the circular construct will use the circular construct as a template and produce a construct comprising multiple copies of each strand of the target polynucleotide. Two constructs will be produced from each target polynucleotide because there are two groups of one or more polymerases. This is shown in FIG. 19. Each construct may be characterised as discussed below. Each construct will typically comprise multiple copies of each strand of the target polynucleotide. The copies in the construct may hybridise together to form double stranded regions. In this embodiment, each strand of the original target polynucleotide will be characterised as many times as the one or more polymerases copy them. The one or polymerases may control the movement of the construct with respect to the pore, such as through the pore. The one or more polymerases may be molecular brakes. If the bridging moiety adaptor also comprises one or more helicases, the one or more helicases may be used to control the movement of the construct with respect to the pore, such as through the pore. In some embodiments, the one or more polymerases and the one or helicases may both be used to control the movement of the construct with respect to the pore, such as through the pore.

After using the one or more polymerases to produce the one or more polylnucleotides, the method preferably comprises contacting the target polynucleotide and the one or more polynucleotides with a transmembrane pore such that the target polynucleotide and the one or more polynucleotides move with respect to the pore, such as through the pore. The method preferably comprises contacting the target polynucleotide and the one or more polynucleotides with a transmembrane pore such that the one or more polymerases control the movement of the target polynucleotide and the one or more polynucleotides with respect to the pore, such as through the pore. One or more helicases may also be used to control the movment of the target polynucleotide and the one or more polynucleotides with respect to the pore, such as through the pore. The one or more helicases may be attached to the target polynucleotide and the one or more polynucleotides as discussed above.

The method also comprises taking one or more measurements as the target polynucleotide and one or more polynucleotides move with respect to the pore wherein the measurements are indicative of one or more characteristics of the polynucleotides and thereby characterising the target polynucleotide. Any of the embodiments discussed below are applicable to this method.

Loading Moiety

The one or more polynucleotide binding proteins are provided bound to (or attached to) one or more loading moieties. In a preferred embodiment, the method further comprises binding (or attaching) the one or more polynucleotide binding proteins to the one or more loading moieties.

Each loading moiety may be any moiety that is capable of being attached to the target polynucleotide. Each loading moiety may be any length as long as the polynucleotide binding proteins may bind and it can be attached to the target polynucleotide.

The one or more loading moieties are preferably synthetic or artificial. The one or more loading moieties are preferably non-natural.

Suitable loading moieties include, but are not limited to a polymeric linker, a chemical linker, a polynucleotide or a polypeptide. The one or more loading moieties preferably comprise a polynucleotide or a loading polynucleotide. In such embodiments, the one or more polynucleotide binding proteins are preferably bound to (or attached to) the polynucleotide. Any of the polynucleotides discussed above may be used. Preferably, the one or more loading moieties comprise DNA, RNA, modified DNA (such as abasic DNA), RNA, PNA, LNA, BNA or PEG. The one or more loading moieties more preferably comprise single stranded or double stranded DNA or RNA.

The one or more loading moieties preferably comprise a single stranded polynucleotide to which the one or more polynucleotide binding proteins are bound (or attached).

At least one of the one or more loading moieties is preferably a Y adaptor. Y adaptors are defined in the section concerning double coupling and may comprise a leader sequence.

At least one of the one or more loading moieties is preferably a bridging moiety. The bridging moiety is most preferably a hairpin loop or a hairpin loop adaptor. Suitable hairpin loop adaptors can be designed using methods known in the art. The hairpin loop may be any length. If used as a loading moiety, the hairpin loop is typically 400 or fewer nucleotides, such as 350 or fewer nucleotides, 300 or fewer nucleotides, 250 or fewer nucleotides, 200 or fewer nucleotides, 150 or fewer nucleotides, 100 or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 400, from 2 to 300, from 5 to 200, from 6 to 100 nucleotides in length. Hairpin loops are formed when two complementary parts of a polynucleotide hybridise to form a double stranded sequence (called a stem). If used as a loading moiety, the stem of the hairpin loop is preferably 200 or fewer nucleotide pairs, such as 150 or fewer nucleotide pairs, 100 or fewer nucleotide pairs, 90 or fewer nucleotide pairs, 80 or fewer nucleotide pairs, 70 or fewer nucleotide pairs, 60 or fewer nucleotide pairs, 50 or fewer nucleotide pairs, 40 or fewer nucleotide pairs, 30 or fewer nucleotide pairs, 20 or fewer nucleotide pairs or 10 or fewer nucleotide pairs, in length. The one or more polynucleotide binding proteins typically bind to the loop of the hairpin, i.e. not the stem.

If the target polynucleotide is double stranded, the one or more loading moieties preferably comprise a Y adaptor and optionally a bridging moiety, such as a hairpin loop adaptor. If at least one or more of the loading moieties is Y adaptor, it may be used in combination with a bridging adaptor that does not have any polynucleotide binding proteins bound or attached.

If the one or more polynucleotide binding proteins are derived from helicases, they may be stalled at one or more spacers on the one or more loading moieties. These are discussed in more detail below.

Any number of one or more loading moieties may be used. The method may comprise attaching two or more loading moieties each having one or more polynucleotide binding proteins bound (attached) thereto. For instance, a loading moiety may be attached to each end of the target polynucleotide. In such embodiments, one loading moiety is preferably a Y adaptor and the other loading moiety may be a bridging moiety, such as a hairpin loop adaptor. These are discussed in more detail below.

The one or more loading moieties may be attached to the target polynucleotide in any manner. The one or more loading moieties are preferably covalently attached to the target polynucleotide.

The one or more loading moieties are most preferably ligated to the target polynucleotide. The one or more loading moieties may be ligated to either end of the polynucleotide, i.e. the 5' or the 3' end. Loading moieties may be ligated to both ends of the target polynucleotide. The one or more loading moieties may be ligated to the polynucleotide using any method known in the art. The one or more loading moieties may be ligated to the polynucleotide in the absence of ATP or using gamma-S-ATP (ATPγS) instead of ATP.

The one or more loading moieties may be ligated using a ligase, such as T4 DNA ligase, E. coli DNA ligase, Taq DNA ligase, Tma DNA ligase and 9° N DNA ligase. The ligase is preferably used under the conditions set out in Example 3.

The method preferably further comprises removing the ligase from the method conditions.

The one or more polynucleotide binding proteins preferably remain bound (attached) to the loading moiety once the loading moiety has been attached to the target polynucleotide. After they have been attached in accordance with the invention, the one or more polynucleotide binding proteins may unbind from the one or more loading moieties.

Membrane

Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphipiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer.

It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesized, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customize polymer based membranes for a wide range of applications.

The membrane is most preferably one of the membranes disclosed in International Application No. PCT/GB2013/052766 or PCT/GB2013/052767.

The amphiphilic molecules may be chemically-modified or functionalised to facilitate coupling of the polynucleotide.

The amphiphilic layer may be a monolayer or a bilayer. The amphiphilic layer is typically planar. The amphiphilic layer may be curved. The amphiphilic layer may be supported.

Amphiphilic membranes are typically naturally mobile, essentially acting as two dimensional fluids with lipid diffusion rates of approximately $10^{-8}$ cm s-1. This means that the detector and coupled polynucleotide can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Planar lipid bilayers may be formed across an aperture in a membrane or across an opening into a recess.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

Tip-dipping bilayer formation entails touching the aperture surface (for example, a pipette tip) onto the surface of a test solution that is carrying a monolayer of lipid. Again, the lipid monolayer is first generated at the solution/air interface by allowing a drop of lipid dissolved in organic solvent to evaporate at the solution surface. The bilayer is then formed by the Langmuir-Schaefer process and requires mechanical automation to move the aperture relative to the solution surface.

For painted bilayers, a drop of lipid dissolved in organic solvent is applied directly to the aperture, which is submerged in an aqueous test solution. The lipid solution is spread thinly over the aperture using a paintbrush or an equivalent. Thinning of the solvent results in formation of a lipid bilayer. However, complete removal of the solvent from the bilayer is difficult and consequently the bilayer formed by this method is less stable and more prone to noise during electrochemical measurement.

Patch-clamping is commonly used in the study of biological cell membranes. The cell membrane is clamped to the end of a pipette by suction and a patch of the membrane becomes attached over the aperture. The method has been adapted for producing lipid bilayers by clamping liposomes which then burst to leave a lipid bilayer sealing over the aperture of the pipette. The method requires stable, giant and unilamellar liposomes and the fabrication of small apertures in materials having a glass surface.

Liposomes can be formed by sonication, extrusion or the Mozafari method (Colas et al. (2007) Micron 38:841-847).

In a preferred embodiment, the lipid bilayer is formed as described in International Application No. PCT/GB08/004127 (published as WO 2009/077734). Advantageously in this method, the lipid bilayer is formed from dried lipids. In a most preferred embodiment, the lipid bilayer is formed across an opening as described in WO2009/077734 (PCT/GB08/004127).

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradecononic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol) 2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the polynucleotide.

The amphiphilic layer, for example the lipid composition, typically comprises one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides.

In another preferred embodiment, the membrane is a solid state layer. Solid state layers can be formed from both organic and inorganic materials including, but not limited to, microelectronic materials, insulating materials such as $Si_3N_4$, $Al_2O_3$, and $SiO$, organic and inorganic polymers such as polyamide, plastics such as Teflon® or elastomers such as two-component addition-cure silicone rubber, and glasses.

The solid state layer may be formed from graphene. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial triblock copolymer layer. The layer may comprise other transmembrane and/or intramembrane proteins as well as other molecules in addition to the pore. Suitable apparatus and conditions are discussed below. The method of the invention is typically carried out in vitro.

Coupling

The one or more loading moieties preferably comprise one or more anchors that are capable of coupling to a membrane. Once attached in accordance with the invention, the one or more anchors are capable of coupling the target polynucleotide to a membrane.

In the characterisation method of the invention, the target polynucleotide is preferably coupled to the membrane using one or more anchors. The target polynucleotide may be coupled to the membrane using any known method.

Each anchor comprises a group which couples (or binds) to the one or more loading moieties and a group which couples (or binds) to the membrane. Each anchor may covalently couple (or bind) to the moiety and/or the membrane.

Each moiety may comprise any number of anchors, such as 2, 3, 4 or more anchors. For instance, one target polynucleotide may be coupled to the membrane using two anchors each of which separately couples (or binds) to both the polynucleotide via a moiety and membrane.

If the membrane is an amphiphilic layer, such as a copolymer membrane or a lipid bilayer, the one or more anchors preferably comprise a polypeptide anchor present in the membrane and/or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the detector.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed in more detail below. Any proportion of the membrane components may be functionalized, for example at least 0.01%, at least 0.1%, at least 1%, at least 10%, at least 25%, at least 50% or 100%.

The one or more anchors used to couple the polynucleotide to the membrane preferably comprise a linker. The one or more anchors may comprise one or more, such as 2, 3, 4 or more, linkers. One linker may be used couple more than one, such as 2, 3, 4 or more, polynucleotides to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The polynucleotide may hybridise to a complementary sequence on the circular polynucleotide linker.

The one or more anchors or one or more linkers may comprise a component that can be cut or broken down, such as a restriction site or a photolabile group.

Functionalised linkers and the ways in which they can couple molecules are known in the art. For instance, linkers functionalised with maleimide groups will react with and attach to cysteine residues in proteins. In the context of this invention, the protein may be present in the membrane or may be used to couple (or bind) to the one or more loading moieties. This is discussed in more detail below.

Crosslinkage of polynucleotides can be avoided using a "lock and key" arrangement. Only one end of each linker may react together to form a longer linker and the other ends of the linker each react with the loading moiety or membrane respectively. Such linkers are described in International Application No. PCT/GB10/000132 (published as WO 2010/086602).

The use of a linker is preferred in the sequencing embodiments discussed below. If a polynucleotide is permanently coupled directly to the membrane in the sense that it does not uncouple when interacting with the detector (i.e. does not uncouple in step (b) or (e)), then some sequence data will be lost as the sequencing run cannot continue to the end of the polynucleotide due to the distance between the membrane and the detector. If a linker is used, then the polynucleotide can be processed to completion.

The coupling may be permanent or stable. In other words, the coupling may be such that the polynucleotide remains coupled to the membrane when interacting with the pore.

The coupling may be transient. In other words, the coupling may be such that the polynucleotide may decouple from the membrane when interacting with the pore.

For certain applications, such as aptamer detection, the transient nature of the coupling is preferred. If a permanent or stable linker is attached directly to either the 5' or 3' end of a polynucleotide and the linker is shorter than the distance between the membrane and the transmembrane pore's channel, then some sequence data will be lost as the sequencing run cannot continue to the end of the polynucleotide. If the coupling is transient, then when the coupled end randomly becomes free of the membrane, then the polynucleotide can be processed to completion. Chemical groups that form permanent/stable or transient links are discussed in more detail below. The polynucleotide may be transiently coupled to an amphiphilic layer or triblock copolymer membrane using cholesterol or a fatty acyl chain. Any fatty acyl chain having a length of from 6 to 30 carbon atom, such as hexadecanoic acid, may be used.

In preferred embodiments, one or more anchors are capable of being coupled to an amphiphilic layer such as a triblock copolymer membrane or lipid bilayer. Coupling of nucleic acids to synthetic lipid bilayers has been carried out previously with various different tethering strategies. These are summarised in Table 1 below.

TABLE 1

| Anchor comprising | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucleotides to lipid membrane assemblies." *J Am Chem Soc* 126(33): 10224-5 |

TABLE 1-continued

| Anchor comprising | Type of coupling | Reference |
|---|---|---|
| Surfactant (e.g. Lipid, Palmitate, etc) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotides and/or linkers may be functionalised using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to loading moieties. Each different modification group couples the loading moiety in a slightly different way and coupling is not always permanent so giving different dwell times for the polynucleotide to the membrane. The advantages of transient coupling are discussed above.

Coupling of polynucleotides to a linker or to a functionalised membrane can also be achieved by a number of other means provided that a complementary reactive group or an anchoring group can be added to the polynucleotide loading moiety. The addition of reactive groups to either end of a polynucleotide has been reported previously. A thiol group can be added to the 5' of ssDNA or dsDNA using T4 polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). An azide group can be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the polynucleotide loading moiety. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82). Streptavidin/biotin and/or streptavidin/desthiobiotin coupling may be used for any other polynucleotide loading moiety. It may also be possible that anchors may be directly added to polynucleotide loading moieties using terminal transferase with suitably modified nucleotides (e.g. cholesterol or palmitate).

The one or more anchors are preferably capable of coupling the loading moiety/polynucleotide to the membrane via hybridisation. Hybridisation in the one or more anchors allows coupling in a transient manner as discussed above. The hybridisation may be present in any part of the one or more anchors, such as between the one or more anchors and the loading moiety, within the one or more anchors or between the one or more anchors and the membrane. For instance, a linker may comprise two or more polynucleotides, such as 3, 4 or 5 polynucleotides, hybridised together. The one or more anchors may hybridise to the polynucleotide loading moiety. The one or more anchors may hybridise directly to the polynucleotide loading moiety such as directly to a Y adaptor and/or leader sequence or directly to a bridging moiety adaptor, such as a hairpin loop adaptor (as discussed below). Alternatively, the one or more anchors may be hybridised to one or more, such as 2 or 3, intermediate polynucleotides (or "splints") which are hybridised to the polynucleotide loading moiety, to a Y adaptor and/or leader sequence or to a bridging moiety adaptor attached to the polynucleotide (as discussed below).

The one or more anchors may comprise a single stranded or double stranded polynucleotide. One part of the anchor may be ligated to a single stranded or double stranded polynucleotide loading moiety. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively, either a single stranded or double stranded polynucleotide can be ligated to a double stranded polynucleotide and then the two strands separated by thermal or chemical denaturation. To a double stranded polynucleotide, it is possible to add either a piece of single stranded polynucleotide to one or both of the ends of the duplex, or a double stranded polynucleotide to one or both ends. For addition of single stranded polynucleotides to the a double stranded polynucleotide, this can be achieved using T4 RNA ligase I as for ligation to other regions of single stranded polynucleotides. For addition of double stranded polynucleotides to a double stranded polynucleotide then ligation can be "blunt-ended", with complementary 3' dA/dT tails on the polynucleotide and added polynucleotide respectively (as is routinely done for many sample prep applications to prevent concatemer or dimer formation) or using "sticky-ends" generated by restriction digestion of the polynucleotide and ligation of compatible adapters. Then, when the duplex is melted, each single strand will have either a 5' or 3' modification if a single stranded polynucleotide was used for ligation or a modification at the 5' end, the 3' end or both if a double stranded polynucleotide was used for ligation.

If the loading moiety is synthetic, the one or more anchors can be incorporated during its chemical synthesis. For instance, a polynucleotide loading moiety can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of a polynucleotide can be possible. It may also be possible that anchors could be directly added to polynucleotide loading moieties using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. Single or multiple nucleotides can be added to 3' end of single or double stranded DNA by employing a polymerase. Examples of polymerases which could be used include, but are not limited to, Terminal Transferase, Klenow and *E. coli* Poly(A) polymerase. By substituting ATP in the reaction for a modified nucleotide triphosphate then anchors, such as a cholesterol, thiol, amine, azide, biotin or lipid, can be incorporated into double stranded polynucleotide loading moieties. Therefore, each copy of the amplified polynucleotide loading moiety will contain an anchor.

Ideally, the loading moiety/polynucleotide is coupled to the membrane without having to functionalise the loading moiety/polynucleotide. This can be achieved by coupling the one or more anchors, such as a polynucleotide binding protein or a chemical group, to the membrane and allowing the one or more anchors to interact with the loading moiety/polynucleotide or by functionalizing the membrane. The one or more anchors may be coupled to the membrane by any of the methods described herein. In particular, the one or more anchors may comprise one or more linkers, such as maleimide functionalised linkers.

The one or more anchors can comprise any group that couples to, binds to or interacts with single or double stranded polynucleotides, specific nucleotide sequences within the loading moiety or patterns of modified nucleotides within the loading moiety, or any other ligand that is present on the loading moiety.

Suitable binding proteins for use in anchors include, but are not limited to, *E. coli* single stranded binding protein, P5 single stranded binding protein, T4 gp32 single stranded binding protein, the TOPO V dsDNA binding region, human histone proteins, *E. coli* HU DNA binding protein and other archaeal, prokaryotic or eukaryotic single stranded or double stranded polynucleotide (or nucleic acid) binding proteins, including those listed below.

The specific nucleotide sequences in the loading moiety could be sequences recognised by transcription factors, ribosomes, endonucleases, topoisomerases or replication initiation factors. The patterns of modified nucleotides could be patterns of methylation or damage.

The one or more anchors can comprise any group which couples to, binds to, intercalates with or interacts with a polynucleotide loading moiety. The group may intercalate or interact with the polynucleotide via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridise with any polynucleotide) and osmium complexes (which can react to methylated bases). A polynucleotide loading moiety may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-O'-methylinosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The one or more anchors may couple to (or bind to) the polynucleotide loading moiety via Hoogsteen hydrogen bonds (where two nucleobases are held together by hydrogen bonds) or reversed Hoogsteen hydrogen bonds (where one nucleobase is rotated through 180° with respect to the other nucleobase). For instance, the one or more anchors may comprise one or more nucleotides, one or more oligonucleotides or one or more polynucleotides which form Hoogsteen hydrogen bonds or reversed Hoogsteen hydrogen bonds with the polynucleotide loading moiety. These types of hydrogen bonds allow a third polynucleotide strand to wind around a double stranded helix and form a triplex. The one or more anchors may couple to (or bind to) a double stranded polynucleotide loading moiety by forming a triplex with the double stranded duplex.

In this embodiment at least 1%, at least 10%, at least 25%, at least 50% or 100% of the membrane components may be functionalized.

Where the one or more anchors comprise a protein, they may be able to anchor directly into the membrane without further functonalisation, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane. Such hydrophobic protein regions are known in the art.

The one or more anchors are preferably mixed with the one or more loading moieties before contacting with the membrane, but the one or more anchors may be contacted with the membrane and subsequently contacted with the one or more loading moieties.

In another aspect a loading moiety may be functionalised, using methods described above, so that it can be recognised by a specific binding group. Specifically the loading moiety may be functionalised with a ligand such as biotin (for binding to streptavidin), amylose (for binding to maltose binding protein or a fusion protein), Ni-NTA (for binding to poly-histidine or poly-histidine tagged proteins) or a peptides (such as an antigen).

According to a preferred embodiment, the one or more anchors may be used to couple a polynucleotide to the membrane when the polynucleotide is attached to a loading moiety comprising a leader sequence which preferentially threads into the pore. Leader sequences are discussed in more detail below. Preferably, the polynucleotide is attached (such as ligated) to a leader sequence which preferentially threads into the pore. Such a leader sequence may comprise a homopolymeric polynucleotide or an abasic region. The leader sequence is typically designed to hybridise to the one or more anchors either directly or via one or more intermediate polynucleotides (or splints). In such instances, the one or more anchors typically comprise a polynucleotide sequence which is complementary to a sequence in the leader sequence or a sequence in the one or more intermediate polynucleotides (or splints). In such instances, the one or more splints typically comprise a polynucleotide sequence which is complementary to a sequence in the leader sequence.

An example of a molecule used in chemical attachment is EDC (1-ethyl-3-[3-dimethylaminopropyl]carbodiimide hydrochloride). Reactive groups can also be added to the 5' of polynucleotides using commercially available kits (Thermo Pierce, Part No. 22980). Suitable methods include, but are not limited to, transient affinity attachment using histidine residues and Ni-NTA, as well as more robust covalent attachment by reactive cysteines, lysines or non natural amino acids.

Transmembrane Pore

The characterisation method of the invention comprises taking one or more measurements as the target polynucleotide moves with respect to the transmembrane pore. A variety of different types of measurements may be made using the pore. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the detector (or pore) as a polynucleotide moves with respect to the pore is used to estimate or determine the sequence of the polynucleotide. This is strand sequencing.

The method comprises contacting the target polynucleotide with a transmembrane pore. A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338: 932-936).

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a triblock copolymer membrane, to the other. The transmembrane protein pore allows a polynucleotide, such as DNA or RNA, to be moved with respect to the pore, such as through the pore.

The transmembrane protein pore may be a monomer or an oligomer. The pore is preferably made up of several repeating subunits, such as at least 6, at least 7, at least 8 or at least 9 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, outer membrane porin F (OmpF), outer membrane porin G (OmpG), outer membrane phospholipase A and *Neisseria* autotransporter lipoprotein (NalP) and other pores such as lysenin. α-helix bundle pores comprise a barrel or channel that is formed from α-helices. Suitable α-helix bundle pores include, but are not limited to, inner membrane proteins and α outer membrane proteins, such as WZA and ClyA toxin. The transmembrane pore may be derived from lysenin. Suitable pores derived from lysenin are disclosed in International Application No. PCT/GB2013/050667 (published as WO 2013/153359). The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et at (1984) Nucleic Acids Research 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et at (1990) J Mol Biol 215:403-10. Software for performing BLAST analyses is publicly available through the National Center for Biotechnology Information (http://www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-B1 and is called MS-(B2)8. The pore used in the invention is preferably MS-(B2)8. A variant of SEQ ID NO: 2 has the mutations G75S/G77S/L88N/Q126R in addition to all the mutations of MS-B1 and is called MS-B2C. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

Chemical properties of amino acids

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 3

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described below.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive $S^-$ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

Any of the proteins described herein, such as the transmembrane protein pores, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or construct. An example of this would be to react a gel-shift reagent to a cysteine engineered on the outside of the pore. This has been demonstrated as a method for separating hemolysin hetero-oligomers (Chem Biol. 1997 July; 4(7):497-505).

The pore may be labelled with a revealing label. The revealing label may be any suitable label which allows the pore to be detected. Suitable labels include, but are not limited to, fluorescent molecules, radioisotopes $^{125}I$, $^{35}S$, enzymes, antibodies, antigens, polynucleotides and ligands such as biotin.

Any of the proteins described herein, such as the transmembrane protein pores, may be made synthetically or by recombinant means. For example, the pore may be synthesized by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

The pore may also be produced using D-amino acids. For instance, the pore or construct may comprise a mixture of L-amino acids and D-amino acids. This is conventional in the art for producing such proteins or peptides.

The pore may also contain other non-specific modifications as long as they do not interfere with pore formation or construct function. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Spacers

If the one or more polynucleotide binding proteins are helicases and the one or more loading moieties comprise a polynucleotide, the one or more helicases may be stalled at one or more spacers as discussed in International Application No. PCT/GB2014/050175 (published as WO 2014/135838). Any configuration of one or more helicases and one or more spacers disclosed in the International Application may be used in this invention.

When a part of the target polynucleotide enters the pore and moves with respect to the pore, such as through the pore, along the field resulting from the applied potential, the one or more helicases are moved past the spacer by the pore as the polynucleotide moves with respect to the pore, such as through the pore. This is because the polynucleotide (including the one or more spacers) moves with respect to the pore, such as through the pore, and the one or more helicases remain on top of the pore.

The one or more spacers are preferably part of the loading moiety polynucleotide, for instance it/they interrupt(s) the polynucleotide sequence. The one or more spacers are preferably not part of one or more blocking molecules, such as speed bumps, hybridised to the polynucleotide.

There may be any number of spacers in the loading moiety polynucleotide, such as 1, 2, 3, 4, 5, 6, 7, 8, 9, 10 or more spacers. There are preferably two, four or six spacers in the polynucleotide. There may be spacer in different loading moiety polynucleotides, such as a spacer in the leader sequence and a spacer in the bridging moiety or the hairpin loop.

The one or more spacers each provides an energy barrier which the one or more helicases cannot overcome even in the active mode. The one or more spacers may stall the one or more helicases by reducing the traction of the helicase (for instance by removing the bases from the nucleotides in the polynucleotide) or physically blocking movement of the one or more helicases (for instance using a bulky chemical group).

The one or more spacers may comprise any molecule or combination of molecules that stalls the one or more helicases. The one or more spacers may comprise any molecule or combination of molecules that prevents the one or more helicases from moving along the polynucleotide. It is straightforward to determine whether or not the one or more helicases are stalled at one or more spacers in the absence of a transmembrane pore and an applied potential. For instance, this can be assayed as shown in the Examples, for instance the ability of a helicase to move past a spacer and displace a complementary strand of DNA can be measured by PAGE.

The one or more spacers typically comprise a linear molecule, such as a polymer. The one or more spacers typically have a different structure from the polynucleotide. For instance, if the polynucleotide is DNA, the one or more spacers are typically not DNA. In particular, if the polynucleotide is deoxyribonucleic acid (DNA) or ribonucleic acid (RNA), the one or more spacers preferably comprise peptide nucleic acid (PNA), glycerol nucleic acid (GNA), threose nucleic acid (TNA), locked nucleic acid (LNA), bridged nucleic acid (BNA) or a synthetic polymer with nucleotide side chains. The one or more spacers may comprise one or more nucleotides in the opposite direction from the polynucleotide. For instance, the one or more spacers may comprise one or more nucleotides in the 3' to 5' direction when the polynucleotide is in the 5' to 3' direction. The nucleotides may be any of those discussed above.

The one or more spacers preferably comprises one or more nitroindoles, such as one or more 5-nitroindoles, one or more inosines, one or more acridines, one or more 2-aminopurines, one or more 2-6-diaminopurines, one or more 5-bromo-deoxyuridines, one or more inverted thymidines (inverted dTs), one or more inverted dideoxy-thymidines (ddTs), one or more dideoxy-cytidines (ddCs), one or more 5-methylcytidines, one or more 5-hydroxymethylcytidines, one or more 2'-O-Methyl RNA bases, one or more Iso-deoxycytidines (Iso-dCs), one or more Iso-deoxyguanosines (Iso-dGs), one or more iSpC3 groups (i.e. nucleotides which lack sugar and a base), one or more photo-cleavable (PC) groups, one or more hexandiol groups, one or more spacer 9 (iSp9) groups, one or more spacer 18 (iSp18) groups, a polymer or one or more thiol connections. The one or more spacers may comprise any combination of these groups. Many of these groups are commercially available from IDT® (Integrated DNA Technologies®).

The one or more spacers may contain any number of these groups. For instance, for 2-aminopurines, 2-6-diaminopurines, 5-bromo-deoxyuridines, inverted dTs, ddTs, ddCs, 5-methylcytidines, 5-hydroxymethylcytidines, 2'-O-Methyl RNA bases, Iso-dCs, Iso-dGs, iSpC3 groups, PC groups, hexandiol groups and thiol connections, the one or more spacers preferably comprise 2, 3, 4, 5, 6, 7, 8, 9, 10, 11, 12 or more. The one or more spacers preferably comprise 2, 3, 4, 5, 6, 7, 8 or more iSp9 groups. The one or more spacers preferably comprise 2, 3, 4, 5 or 6 or more iSp18 groups. The most preferred spacer is four iSp18 groups.

The polymer is preferably a polypeptide or a polyethylene glycol (PEG). The polypeptide preferably comprises 2, 3, 4, 5, 6, 7, 8, 9, 10, 11, 12 or more amino acids. The PEG preferably comprises 2, 3, 4, 5, 6, 7, 8, 9, 10, 11, 12 or more monomer units.

The one or more spacers preferably comprise one or more abasic nucleotides (i.e. nucleotides lacking a nucleobase), such as 2, 3, 4, 5, 6, 7, 8, 9, 10, 11, 12 or more abasic nucleotides. The nucleobase can be replaced by —H (idSp) or —OH in the abasic nucleotide. Abasic spacers can be inserted into polynucleotides by removing the nucleobases from one or more adjacent nucleotides. For instance, polynucleotides may be modified to include 3-methyladenine, 7-methylguanine, 1,N6-ethenoadenine inosine or hypoxanthine and the nucleobases may be removed from these nucleotides using Human Alkyladenine DNA Glycosylase (hAAG). Alternatively, polynucleotides may be modified to include uracil and the nucleobases removed with Uracil-DNA Glycosylase (UDG). In one embodiment, the one or more spacers do not comprise any abasic nucleotides.

The one or more helicases may be stalled by (i.e. before) or on each linear molecule spacer. If linear molecule spacers are used, the loading moiety polynucleotide is preferably provided with a double stranded region of polynucleotide adjacent to the end of each spacer past which the one or more helicases are to be moved. The double stranded region typically helps to stall the one or more helicases on the adjacent spacer. The presence of the double stranded region (s) is particularly preferred if the method is carried out at a salt concentration of about 100 mM or lower. Each double stranded region is typically at least 10, such as at least 12, nucleotides in length. If the loading moiety polynucleotide used in the invention is single stranded, a double stranded region may formed by hybridising a shorter polynucleotide to a region adjacent to a spacer. The shorter polynucleotide is typically formed from the same nucleotides as the loading moiety polynucleotide, but may be formed from different nucleotides. For instance, the shorter polynucleotide may be formed from LNA or BNA.

If linear molecule spacers are used, the loading moiety polynucleotide is preferably provided with a blocking molecule at the end of each spacer opposite to the end past which the one or more helicases are to be moved. This can help to ensure that the one or more helicases remain stalled on each spacer. It may also help retain the one or more helicases on the polynucleotide in the case that it/they diffuse(s) off in solution. The blocking molecule may be any of the chemical groups discussed below which physically cause the one or more helicases to stall. The blocking molecule may be a double stranded region of polynucleotide.

The one or more spacers preferably comprise one or more chemical groups which physically cause the one or more helicases to stall. The one or more chemical groups are preferably one or more pendant chemical groups. The one or more chemical groups may be attached to one or more nucleobases in the polynucleotide. The one or more chemical groups may be attached to the polynucleotide backbone. Any number of these chemical groups may be present, such as 2, 3, 4, 5, 6, 7, 8, 9, 10, 11, 12 or more. Suitable groups include, but are not limited to, fluorophores, streptavidin and/or biotin, cholesterol, methylene blue, dinitrophenols (DNPs), digoxigenin and/or anti-digoxigenin and dibenzylcyclooctyne groups.

Different spacers in the loading moiety polynucleotide may comprise different stalling molecules. For instance, one spacer may comprise one of the linear molecules discussed above and another spacer may comprise one or more chemical groups which physically cause the one or more helicases to stall. A spacer may comprise any of the linear molecules discussed above and one or more chemical groups which physically cause the one or more helicases to stall, such as one or more abasics and a fluorophore.

Suitable spacers can be designed depending on the type of loading moiety polynucleotide and the conditions under which the method of the invention is carried out. Most helicases bind and move along DNA and so may be stalled using anything that is not DNA. Suitable molecules are discussed above.

The characterisation method of the invention is preferably carried out in the presence of free nucleotides and/or the presence of a helicase cofactor. This is discussed in more detail below. In the absence of the transmembrane pore and an applied potential, the one or more spacers are preferably capable of stalling the one or more helicases in the presence of free nucleotides and/or the presence of a helicase cofactor.

If the characterization method of the invention is carried out in the presence of free nucleotides and a helicase cofactor as discussed below (such that the one of more helicases are in the active mode), one or more longer spacers are typically used to ensure that the one or more helicases are stalled on the polynucleotide before they are contacted with the transmembrane pore and a potential is applied. One or more shorter spacers may be used in the absence of free nucleotides and a helicase cofactor (such that the one or more helicases are in the inactive mode).

The salt concentration also affects the ability of the one or more spacers to stall the one or more helicases. In the absence of the transmembrane pore and an applied potential, the one or more spacers are preferably capable of stalling the one or more helicases at a salt concentration of about 100 mM or lower. The higher the salt concentration used in the method of the invention, the shorter the one or more spacers that are typically used and vice versa.

Preferred combinations of features are shown in Table 4 below.

| Polynu-cleotide | Spacer compo-sition* | Spacer length (i.e. number of *) | Salt [ ] | Free nucleotides? | Helicase cofactor? |
|---|---|---|---|---|---|
| DNA | iSpC3 | 4 | 1M | Yes | Yes |
| DNA | iSp18 | 4 | 100-1000 mM | Yes | Yes |
| DNA | iSp18 | 6 | <100-1000 mM | Yes | Yes |
| DNA | iSp18 | 2 | 1M | Yes | Yes |
| DNA | iSpC3 | 12 | <100-1000 mM | Yes | Yes |
| DNA | iSpC3 | 20 | <100-1000 mM | Yes | Yes |
| DNA | iSp9 | 6 | 100-1000 mM | Yes | Yes |
| DNA | idSp | 4 | 1M | Yes | Yes |

The method may concern moving two or more helicases past a spacer. In such instances, the length of the spacer is typically increased to prevent the trailing helicase from pushing the leading helicase past the spacer in the absence of the pore and applied potential. If the method concerns moving two or more helicases past one or more spacers, the spacer lengths discussed above may be increased at least 1.5 fold, such 2 fold, 2.5 fold or 3 fold. For instance, if the method concerns moving two or more helicases past one or more spacers, the spacer lengths in the third column of Table 4 above may be increased 1.5 fold, 2 fold, 2.5 fold or 3 fold.

The two or more helicases may also be separated such that each has its own one or more spacers. This is discussed in more detail below.

Double Stranded Polynucleotide

The target polynucleotide may be double stranded. If the polynucleotide is double stranded, the invention preferably comprises attaching a bridging moiety adaptor, such as a hairpin loop adaptor, at one end of the polynucleotide and separating the two strands of the polynucleotide to form a single stranded polynucleotide construct. The single stranded polynucleotide construct may then be moved with respect to the pore, such as through the pore, in accordance with the invention. Linking and interrogating both strands on a double stranded construct in this way increases the efficiency and accuracy of characterisation.

The bridging moiety is capable of linking the two strands of the polynucleotide. The bridging moiety typically covalently links the two strands of the polynucleotide. The bridging moiety can be anything that is capable of linking the two strands of the polynucleotide, provided that the bridging moiety does not interfere with movement of the polynucleotide through the transmembrane pore.

The bridging moiety may be linked to the polynucleotide by any suitable means known in the art. The bridging moiety may be synthesized separately and chemically attached or enzymatically ligated to the polynucleotide. Alternatively, the bridging moiety may be generated in the processing of the polynucleotide.

The bridging moiety is linked to the polynucleotide at or near one end of the polynucleotide. The bridging moiety is preferably linked to the polynucleotide within 10 nucleotides of the end of the polynucleotide.

Although bridging moieties are preferred loading moieties, the bridging moiety does not have to have one or more bound (or attached) polynucleotide binding proteins bound as long as a loading moiety, such as a Y adaptor, has one or more bound (or attached) polynucleotide binding proteins attached to the other end of the target polynucleotide. In some embodiments, loading moieties may be attached at both ends of the polynucleotide of the invention, preferably where one is a Y adaptor and the other is a bridging moiety, such as a hairpin loop adaptor. Suitable bridging moieties are discussed above with reference to the loading moieties. If the hairpin loop is not being used as a loading moiety, the hairpin loop is typically 110 or fewer nucleotides, such as 100 or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 110, from 2 to 100, from 5 to 80 or from 6 to 50 nucleotides in length. Longer lengths of the hairpin loop, such as from 50 to 110 nucleotides, are preferred if the loop is involved in the differential selectable binding of the adaptor. Similarly, shorter lengths of the hairpin loop, such as from 1 to 5 nucleotides, are preferred if the loop is not involved in the selectable binding as discussed below.

The bridging moiety adaptor or hairpin loop adaptor may be attached or ligated to the target polynucleotide as discussed above.

The two strands of the polynucleotide may be separated using any method known in the art. For instance, they may be separated by one or more polynucleotide binding proteins or using conditions which favour dehybridsation (examples of conditions which favour dehybridisation include, but are not limited to, high temperature, high pH and the addition of agents that can disrupt hydrogen bonding or base pairing, such as formamide and urea). If one or more polynucleotide binding proteins are used to separate the strands, the one or more polynucleotide binding proteins are typically attached to the target polynucleotide at the other end from the bridging moiety, for instance using a Y adaptor.

The one or more loading moieties, preferably the Y adaptor and/or the bridging moiety adaptor (such as the hairpin loop adaptor), preferably comprises a selectable binding moiety. This allows the polynucleotide to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a polynucleotide sequence, antibodies, antibody fragments, such as Fab and ScSv, antigens, polynucleotide binding proteins, poly histidine tails and GST tags. The most preferred selective binding moieties are biotin and a selectable polynucleotide sequence. Biotin specifically binds to a surface coated with avidins. Selectable polynucleotide sequences specifically bind (i.e. hybridise) to a surface coated with homologus sequences. Alternatively, selectable polynucleotide sequences specifically bind to a surface coated with polynucleotide binding proteins.

The one or more loading moieties, preferably the Y adaptor and/or the bridging moiety adaptor (such as the hairpin loop adaptor) and/or the selectable binding moiety may comprise a region that can be cut, nicked, cleaved or hydrolysed. Such a region can be designed to allow the first and/or second polynucleotide to be removed from the surface to which it is bound following purification or isolation. Suitable regions are known in the art. Suitable regions include, but are not limited to, an RNA region, a region comprising desthiobiotin and streptavidin, a disulphide bond and a photocleavable region.

Leader Sequence

The one or more loading moieties may be provided with a leader sequence which preferentially threads into the pore. The leader sequence facilitates the method of the invention. The leader sequence is designed to preferentially thread into the transmembrane pore and thereby facilitate the movement of target polynucleotide with respect to the pore, such as through the pore. The leader sequence can also be used to link the polynucleotide to the one or more anchors as discussed above.

The leader sequence typically comprises a polymer. The polymer is preferably negatively charged. The polymer is preferably a polynucleotide, such as DNA or RNA, a modified polynucleotide (such as abasic DNA), PNA, LNA, BNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

Double Coupling

In a preferred embodiment, the invention comprises a method for attaching one or more polynucleotide binding proteins to a target double stranded polynucleotide, comprising:

(a) providing a Y adaptor with one or more polynucleotide binding proteins bound (or attached) to it and one or more first anchors for coupling the polynucleotide to a membrane and providing a bridging moiety adaptor, such as a hairpin loop adaptor, with one or more second anchors wherein the strength of coupling of the bridging moiety adaptor to the membrane is greater than the strength of coupling of the Y adaptor to the membrane; and (b) attaching the Y adaptor to one end of the target polynucleotide and attaching the bridging moiety to the other end of the target polynucleotide. The bridging moiety preferably has one or more polynucleotide binding proteins, preferably one or more molecular brakes, attached to it.

The invention also provides a method of characterising a target double stranded polynucleotide comprising (c) contacting the polynucleotide provided in step (b) above with a transmembrane pore such that the one or more polynucleotide binding proteins control the movement of the target polynucleotide with respect to the pore, such as through the pore; and (d) taking one or more measurements as the polynucleotide moves with respect to the pore wherein the measurements are indicative of one or more characteristics of the polynucleotide and thereby characterising the target polynucleotide.

This type of method is discussed in detail in UK Application No. 1406147.7.

The Y adaptor and/or the bridging moiety adaptor are typically polynucleotide adaptors. They may be formed from any of the polynucleotides discussed above.

The Y adaptor typically comprises (a) a double stranded region and (b) a single stranded region or a region that is not complementary at the other end. The Y adaptor may be described as having an overhang if it comprises a single stranded region. The presence of a non-complementary region in the Y adaptor gives the adaptor its Y shape since the two strands typically do not hybridise to each other unlike the double stranded portion. The Y adaptor comprises the one or more first anchors. Anchors are discussed in more detail above.

The Y adaptor preferably comprises a leader sequence which preferentially threads into the pore. This is discussed above.

The bridging moiety adaptor preferably comprises a selectable binding moiety as discussed above. The bridging moiety adaptor and/or the selectable binding moiety may comprise a region that can be cut, nicked, cleaved or hydrolysed as discussed above.

The Y adaptor and/or the bridging moiety adaptor may be ligated to the polynucleotide using any method known in the art. One or both of the adaptors may be ligated using a ligase, such as T4 DNA ligase, *E. coli* DNA ligase, Taq DNA ligase, Tma DNA ligase and 9° N DNA ligase.

The strength of coupling (or binding) of the bridging moiety adaptor to the membrane is greater than the strength of coupling (or binding) of the Y adaptor to the membrane. This can be measured in any way. A suitable method for measuring the strength of coupling (or binding) is disclosed in the Examples of UK Application No. 1406147.7.

The strength of coupling (or binding) of the bridging moiety adaptor is preferably at least 1.5 times the strength of coupling (or binding) of the Y adaptor, such as at least twice, at least three times, at least four times, at least five or at least ten times the strength of coupling (or binding) of the Y adaptor. The affinity constant (Kd) of the bridging moiety adaptor for the membrane is preferably at least 1.5 times the affinity constant of the Y adaptor, such as at least twice, at least three times, at least four times, at least five or at least ten times the strength of coupling of the Y adaptor.

There are several ways in which the bridging moiety adaptor couples (or binds) more strongly to the membrane than the Y adaptor. For instance, the bridging moiety adaptor may comprise more anchors that than the Y adaptor. For instance, the bridging moiety adaptor may comprise 2, 3 or more second anchors whereas the Y adaptor may comprise one first anchor.

The strength of coupling (or binding) of the one or more second anchors to the membrane may be greater than the strength of coupling (or binding) of the one or more first anchors to the membrane. The strength of coupling (or binding) of the one or more second anchors to the bridging moiety adaptor may be greater than the strength of coupling (or binding) of the one or more first anchors to the Y adaptor. The one or more first anchors and the one or more second anchors may be attached to their respective adaptors via hybridisation and the strength of hybridisation is greater in the one or more second anchors than in the one or more first anchors. Any combination of these embodiments may also be used in the invention. Strength of coupling (or binding) may be measured using known techniques in the art.

The one or more second anchors preferably comprise one or more groups which couples(s) (or bind(s)) to the membrane with a greater strength than the one or more groups in the one or more first anchors which couple(s) (or bind(s)) to the membrane. In preferred embodiments, the bridging moiety adaptor/one or more second anchors couple (or bind) to the membrane using cholesterol and the Y adaptor/one or more first anchors couple (or bind) to the membrane using palmitate. Cholesterol binds to triblock copolymer membranes and lipid membranes more strongly than palmitate. In an alternative embodiment, the bridging moiety adaptor/one or more second anchors couple (or bind) to the membrane using a mono-acyl species, such as palmitate, and the Y adaptor/one or more first anchors couple (or bind) to the membrane using a diacyl species, such as dipalmitoylphosphatidylcholine.

Adding Hairpin Loops and Leader Sequences

In accordance with the invention, a double stranded polynucleotide may be contacted with a MuA transposase and a population of double stranded MuA substrates, wherein a proportion of the substrates in the population are Y adaptors bound to one or more polynucleotide binding proteins and comprising the leader sequence and wherein a proportion of the substrates in the population are bridging moiety adaptors, such as hairpin loop adaptors bound to one or more polynucleotide binding proteins. The Y adaptors and/or the bridging moiety adaptors function as the loading moieties. The transposase fragments the double stranded polynucleotide and ligates MuA substrates to one or both ends of the fragments. This produces a plurality of modified double stranded polynucleotides comprising the Y adaptor with the one or more polynucleotide binding proteins and leader sequence at one end and the bridging moiety (or hairpin loop) with the one or more polynucleotide binding proteins at the other. The modified double stranded polynucleotides may then be characterised using the method of the invention.

Each substrate in the population preferably comprises at least one overhang of universal nucleotides such that the transposase fragments the template polynucleotide and ligates a substrate to one or both ends of the double stranded fragments and thereby produces a plurality of fragment/substrate constructs and wherein the method further comprises ligating the overhangs to the fragments in the constructs and thereby producing a plurality of modified double stranded polynucleotides. Suitable universal nucleotides are discussed above. The overhang is preferably five nucleotides in length.

Alternatively, each substrate in the population preferably comprises (i) at least one overhang and (ii) at least one nucleotide in the same strand as the at least one overhang which comprises a nucleoside that is not present in the template polynucleotide such that the transposase fragments the template polynucleotide and ligates a substrate to one or both ends of the double stranded fragments and thereby produces a plurality of fragment/substrate constructs, and wherein the method further comprises (a) removing the overhangs from the constructs by selectively removing the at least one nucleotide and thereby producing a plurality of double stranded constructs comprising single stranded gaps and (b) repairing the single stranded gaps in the constructs and thereby producing a plurality of modified double stranded polynucleotides. The polynucleotide analyte typically comprises the nucleosides deoxyadenosine (dA), deoxyuridine (dU) and/or thymidine (dT), deoxyguanosine (dG) and deoxycytidine (dC). The nucleoside that is not present in the polynucleotide is preferably abasic, adenosine (A), uridine (U), 5-methyluridine ($m^5U$), cytidine (C) or guanosine (G) or comprises urea, 5, 6 dihydroxythymine, thymine glycol, 5-hydroxy-5 methylhydanton, uracil glycol, 6-hydroxy-5, 6-dihdrothimine, methyltartronylurea, 7, 8-dihydro-8-oxoguanine (8-oxoguanine), 8-oxoadenine, fapyguanine, methy-fapy-guanine, fapy-adenine, aflatoxin B1-fapy-guanine, 5-hydroxy-cytosine, 5-hydroxy-uracil, 3-methyladenine, 7-methylguanine, 1,N6-ethenoadenine, hypoxanthine, 5-hydroxyuracil, 5-hydroxymethyluracil, 5-formyluracil or a cis-syn-cyclobutane pyrimidine dimer. The at least one nucleotide preferably is 10 nucleotides or fewer from the overhang. The at least one nucleotide preferably is the first nucleotide in the overhang. All of the nucleotides in the overhang preferably comprise a nucleoside that is not present in the template polynucleotide.

These MuA based methods are disclosed in UK Application No. 1314695.6. They are also discussed in detail in UK Application No. 1406147.7.

One or more helicases may be attached to the MuA substrate Y adaptors (i.e. loading moieties) before they are contacted with the double stranded polynucleotide and MuA transposase. Alternatively, one or more helicases may be attached to the MuA substrate Y adaptors (i.e. loading moieties) after they are contacted with the double stranded polynucleotide and MuA transposase.

One or more molecular brakes may be attached to the MuA substrate bridging moiety (or hairpin loop) adaptors before they are contacted with the double stranded polynucleotide and MuA transposase. Alternatively, one or more molecular brakes may be attached to the MuA substrate bridging moiety (or hairpin loop) adaptors after they are contacted with the double stranded polynucleotide and MuA transposase.

Polynucleotide Characterisation

The invention provides a method of characterising a target polynucleotide. The target polynucleotide may also be called the template polynucleotide or the polynucleotide of interest.

The method of the invention involves measuring one or more characteristics of the polynucleotide. In particular, one of the methods above for controlling the movement of a polynucleotide through a transmembrane pore is carried out as step (a) and then in step (b) one or more measurements are taken as the polynucleotide moves with respect to the pore wherein the measurements are indicative of one or more characteristics of the polynucleotide. Suitable measurements are discussed above.

Any number of target polynucleotides can be investigated. For instance, the method of the invention may concern characterising 2, 3, 4, 5, 6, 7, 8, 9, 10, 20, 30, 50, 100 or more target polynucleotides. The target polynucleotide can be naturally occurring or artificial. For instance, the method may be used to verify the sequence of manufactured oligonucleotides. The methods are typically carried out in vitro.

The method may involve measuring one, two, three, four or five or more characteristics of the target polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention, such as {i}, {ii}, {iii}, {iv}, {v}, {i,ii}, {i,iii}, {i,iv}, {i,v}, {ii,iii}, {ii,iv}, {ii,v}, {iii,iv}, {iii,v}, {iv,v}, {i,ii,iii}, {i,ii,iv}, {i,ii,v}, {i,iii,iv}, {i,iii,v}, {i,iv,v}, {ii,iii,iv}, {ii,iii,v}, {ii,iv,v}, {iii,iv,v}, {i,ii,iii,iv}, {i,ii,iii,v}, {i,ii,iv,v}, {i,iii,iv,v}, {ii,iii,iv,v} or {i,ii,iii,iv,v}.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing with respect to the pore, such as through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing with respect to the pore, such as through the pore, during its interaction with each nucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Bridging Moiety Sequencing

In a preferred embodiment, a target double stranded polynucleotide is provided with a bridging moiety (or hairpin loop) adaptor at one end and the method comprises contacting the polynucleotide with a transmembrane pore such that both strands of the polynucleotide move with respect to the pore, such as through the pore, and taking one or more measurements as the both strands of the polynucleotide move with respect to the pore wherein the measurements are indicative of one or more characteristics of the strands of the polynucleotide and thereby characterising the target double stranded polynucleotide. Any of the embodiments discussed above equally apply to this embodiment.

Modified Polynucleotides

Before use in the method of the invention, a polynucleotide may be modified by contacting the polynucleotide with a polymerase and a population of free nucleotides under conditions in which the polymerase forms a modified polynucleotide using the polynucleotide as a template, wherein the polymerase replaces one or more of the nucleotide species in the polynucleotide with a different nucleotide species when forming the modified polynucleotide. The modified polynucleotide may then be used in the methods of the invention. This type of modification is described in UK Application No. 1403096.9. Any of the polymerases discussed above may be used. The polymerase is preferably Klenow or 9° North.

The polynucleotide is contacted with the polymerase under conditions in which the polymerase forms a modified polynucleotide using the polynucleotide as a template. Such conditions are known in the art. For instance, the polynucleotide is typically contacted with the polymerase in commercially available polymerase buffer, such as buffer from New England Biolabs®. The temperature is preferably from 20 to 37° C. for Klenow or from 60 to 75° C. for 9° North. A primer or a 3' hairpin is typically used as the nucleation point for polymerase extension. The polymerase may be contacted with the target polynucleotide in accordance with the invention, i.e. by (a) providing the one or more polymerases bound to one or more loading moieties and (b) attaching the one or more loading moieties to the target polynucleotide.

Characterisation, such as sequencing, of a polynucleotide using a transmembrane pore typically involves analyzing polymer units made up of k nucleotides where k is a positive integer (i.e. 'k-mers'). This is discussed in International Application No. PCT/GB2012/052343 (published as WO 2013/041878). While it is desirable to have clear separation between current measurements for different k-mers, it is common for some of these measurements to overlap. Especially with high numbers of polymer units in the k-mer, i.e. high values of k, it can become difficult to resolve the measurements produced by different k-mers, to the detriment of deriving information about the polynucleotide, for example an estimate of the underlying sequence of the polynucleotide.

By replacing one or more nucleotide species in the polynucleotide with different nucleotide species in the modified polynucleotide, the modified polynucleotide contains k-mers which differ from those in the polynucleotide. The different k-mers in the modified polynucleotide are capable of producing different current measurements from the k-mers in the polynucleotide and so the modified polynucleotide provides different information from the polynucleotide. The additional information from the modified polynucleotide can make it easier to characterise the polynucleotide. In some instances, the modified polynucleotide itself may be easier to characterise. For instance, the modified polynucleotide may be designed to include k-mers with an increased separation or a clear separation between their current measurements or k-mers which have a decreased noise.

The polymerase preferably replaces two or more of the nucleotide species in the polynucleotide with different nucleotide species when forming the modified polynucleotide. The polymerase may replace each of the two or more nucleotide species in the polynucleotide with a distinct nucleotide species. The polymerase may replace each of the two or more nucleotide species in the polynucleotide with the same nucleotide species.

If the polynucleotide is DNA, the different nucleotide species in the modified polynucleotide typically comprises a nucleobase which differs from adenine, guanine, thymine, cytosine or methylcytosine and/or comprises a nucleoside which differs from deoxyadenosine, deoxyguanosine, thymidine, deoxycytidine or deoxymethylcytidine. If the polynucleotide is RNA, the different nucleotide species in the modified polynucleotide typically comprises a nucleobase which differs from adenine, guanine, uracil, cytosine or methylcytosine and/or comprises a nucleoside which differs from adenosine, guanosine, uridine, cytidine or methylcytidine. The different nucleotide species may be any of the universal nucleotides discussed above.

The polymerase may replace the one or more nucleotide species with a different nucleotide species which comprises a chemical group or atom absent from the one or more nucleotide species. The chemical group may be a propynyl group, a thio group, an oxo group, a methyl group, a hydroxymethyl group, a formyl group, a carboxy group, a carbonyl group, a benzyl group, a propargyl group or a propargylamine group.

The polymerase may replace the one or more nucleotide species with a different nucleotide species which lacks a chemical group or atom present in the one or more nucleotide species. The polymerase may replace the one or more of the nucleotide species with a different nucleotide species having an altered electronegativity. The different nucleotide species having an altered electronegativity preferably comprises a halogen atom.

The method preferably further comprises selectively removing the nucleobases from the one or more different nucleotides species in the modified polynucleotide.

Products The invention also provides a target polynucleotide modified using the invention. The invention also provides a loading moiety having one or more polynucleotide binding proteins bound to it. Any of the embodiments discussed above with reference to the method of the invention apply to the polynucleotide and moiety of the invention.

Kits

The present invention also provides a kit for attaching one or more polynucleotide binding proteins to a target polynucleotide, comprising (a) the one or more polynucleotide binding proteins bound to one or more loading moieties and (b) a ligase. Any of the embodiments discussed above apply to the kits.

The kit is preferably for a double stranded polynucleotide through a transmembrane pore and the kit preferably comprises a Y adaptor having one or more helicases attached and a bridging moiety (or hairpin loop) adaptor having one or more molecular brakes attached. The Y adaptor preferably comprises one or more first anchors for coupling the polynucleotide to the membrane, the bridging moiety (or hairpin loop) adaptor preferably comprises one or more second anchors for coupling the polynucleotide to the membrane and the strength of coupling of the bridging moiety (or hairpin loop) adaptor to the membrane is preferably greater than the strength of coupling of the Y adaptor to the membrane.

The kit preferably further comprises a transmembrane pore. Any of the membrane and pores discussed above may be in the kit.

Any of the embodiments discussed above with reference to the method of the invention equally apply to the kits. The kit may further comprise the components of a membrane, such as the components of an amphiphilic layer or a triblock copolymer membrane.

The kit of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding for which organism the method may be used.

The following Examples illustrate the invention.

Example 1

This example describes the sample preparation procedure for binding a polynucleotide binding protein to a loading moiety.

Materials and Methods

TrwC Cba-L376C/Q594A/K762C (6.5 µM, SEQ ID NO: 25 with mutations L376C/Q594A/K762C) and DNA hairpin-adapter (4 SEQ ID NO: 29 was attached at the 3' end to four iSpC3 spacers which are attached at the opposite end to the 5' end of SEQ ID NO: 30) were mixed in buffer (100 mM KCl, 100 mM CAPS (pH 10) and 1 mM EDTA) and incubated for 30 minutes. TRIS (0.1 volumes of 1 M TRIS pH 7.0) was added to the DNA/enzyme mixture and the mixture thoroughly mixed. Finally, 0.025 volumes of 1.29 mM Bismaleimideoethane in DMF was added and the mixture incubated for a further 15 minutes. The final concentrations of each component were as follows TrwC Cba-L376C/Q594A/K762C (5.8 DNA Hairpin-adapter (3.56 Buffer (89 mM KCl, 89 mM CAPS, pH 10, 0.89 mM EDTA, 89 mM Tris (pH 7)) and Bismaleimideoethane (28.7 this mixture was known as sample 1.

The pre-bound TrwC Cba-L376C/Q594A/K762C to the DNA Hairpin-adapter was then purified using the procedure described using an 8 mL POROS HQ-10 column (FPLC) and the following elution buffers (Buffer A—50 mM Ethanolamine, 300 mM NaCl, 0.1% β-OTG, 1 mM TCEP, pH 10.0, Buffer B—50 mM Ethanolamine, 700 mM NaCl, 0.1% β-OTG, 1 mM TCEP, pH 10.0). Sample 1 was loaded onto the column and any DNA which did not have TrwC Cba-L376C/Q594A/K762C bound or enzyme which was not bound to DNA was washed off the column using 5 column volumes of buffer A. The pre-bound TrwC Cba-L376C/Q594A/K762C to the DNA Hairpin-adapter was then eluted with 0-100% buffer B in 11.8 column volumes, this sample was known as Sample 2. An example FPLC trace is shown in FIG. 1 the peak labelled P1 corresponded to pre-bound TrwC Cba-L376C/Q594A/K762C to the DNA Hairpin-adapter.

Figure 2:
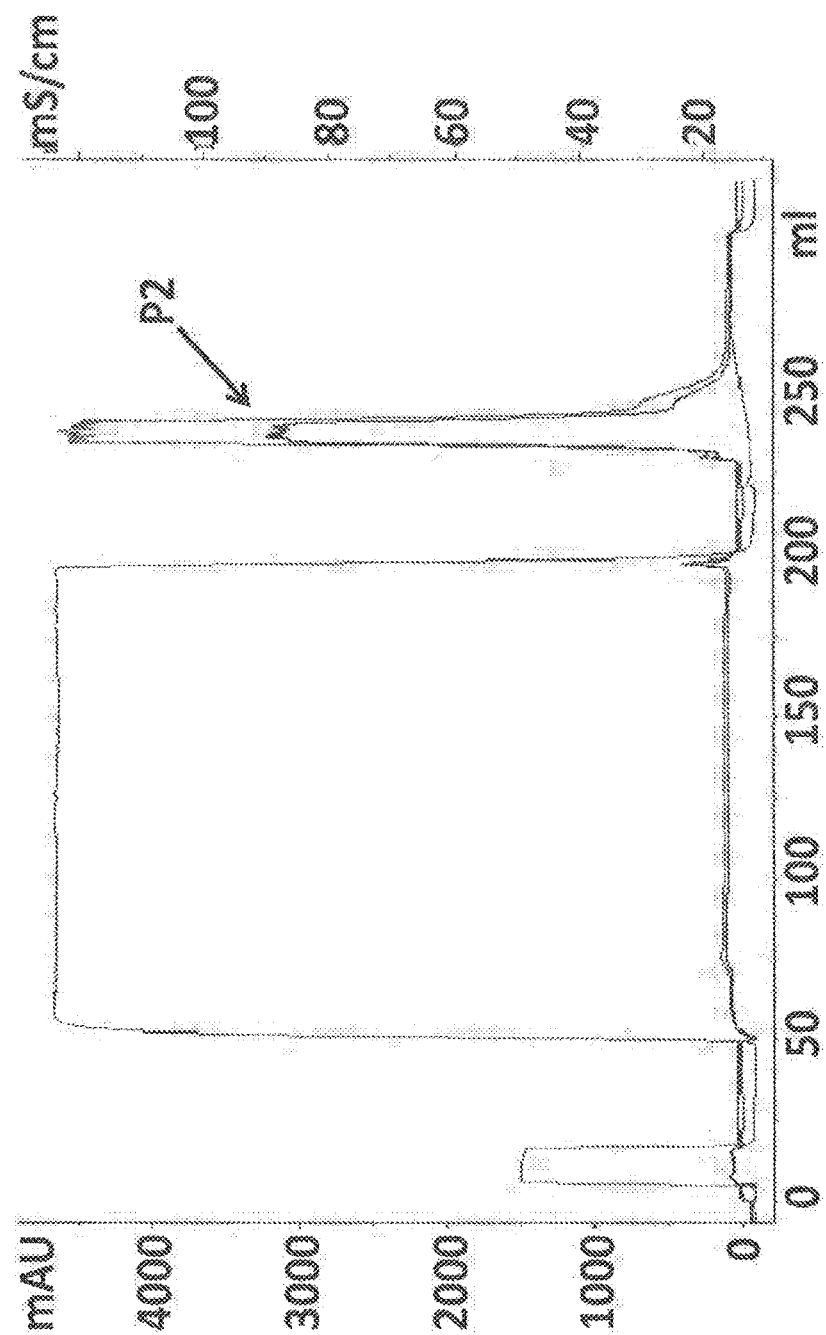
FIG. 2 shows an example FPLC trace after purification of the pre-bound TrwC Cba-L376C/Q594A/K762C to the DNA Hairpin-adapter using a 5 mL Histrap HP column.
Figure 3:
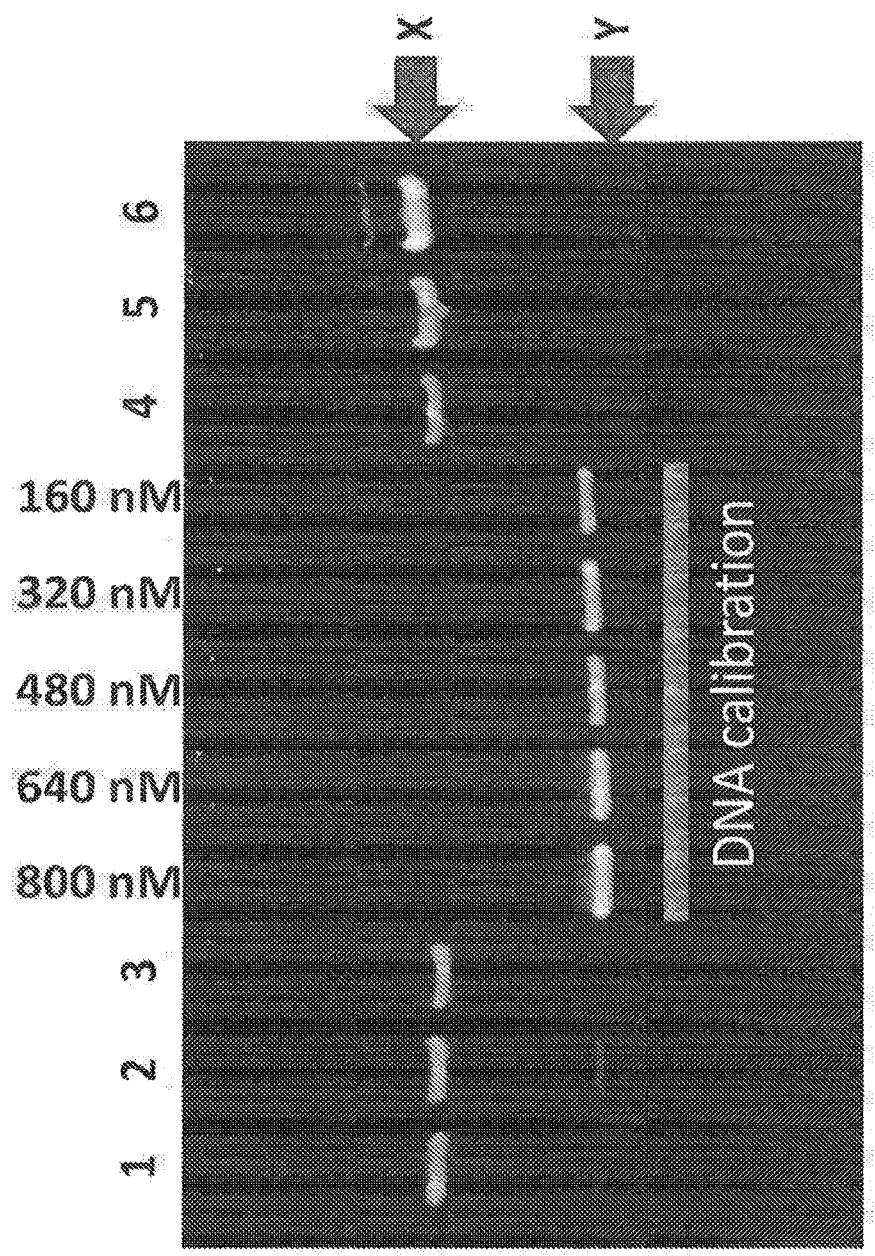
FIG. 3 shows the TBE (native) PAGE gel analysis (the DNA calibration band corresponds to the DNA concentration shown at the top of the gel) column 1 shows the TrwC Cba-L376C/Q594A/K762C bound to the DNA Hairpin-adapter in buffer only (shown as band X), column 2 shows the TrwC Cba-L376C/Q594A/K762C bound to the DNA Hairpin-adapter after the TRIS buffer was added, column 3 shows the TrwC Cba-L376C/Q594A/K762C bound to the DNA Hairpin-adapter after the addition of Bismaleimideoethane, columns 4-6 show varying dilutions of TrwC Cba-L376C/Q594A/K762C bound to the DNA Hairpin-adapter after both FPLC purifications. Band X corresponded to enzyme bound to DNA. Band Y corresponded to DNA with no enzyme bound.
Figure 4:
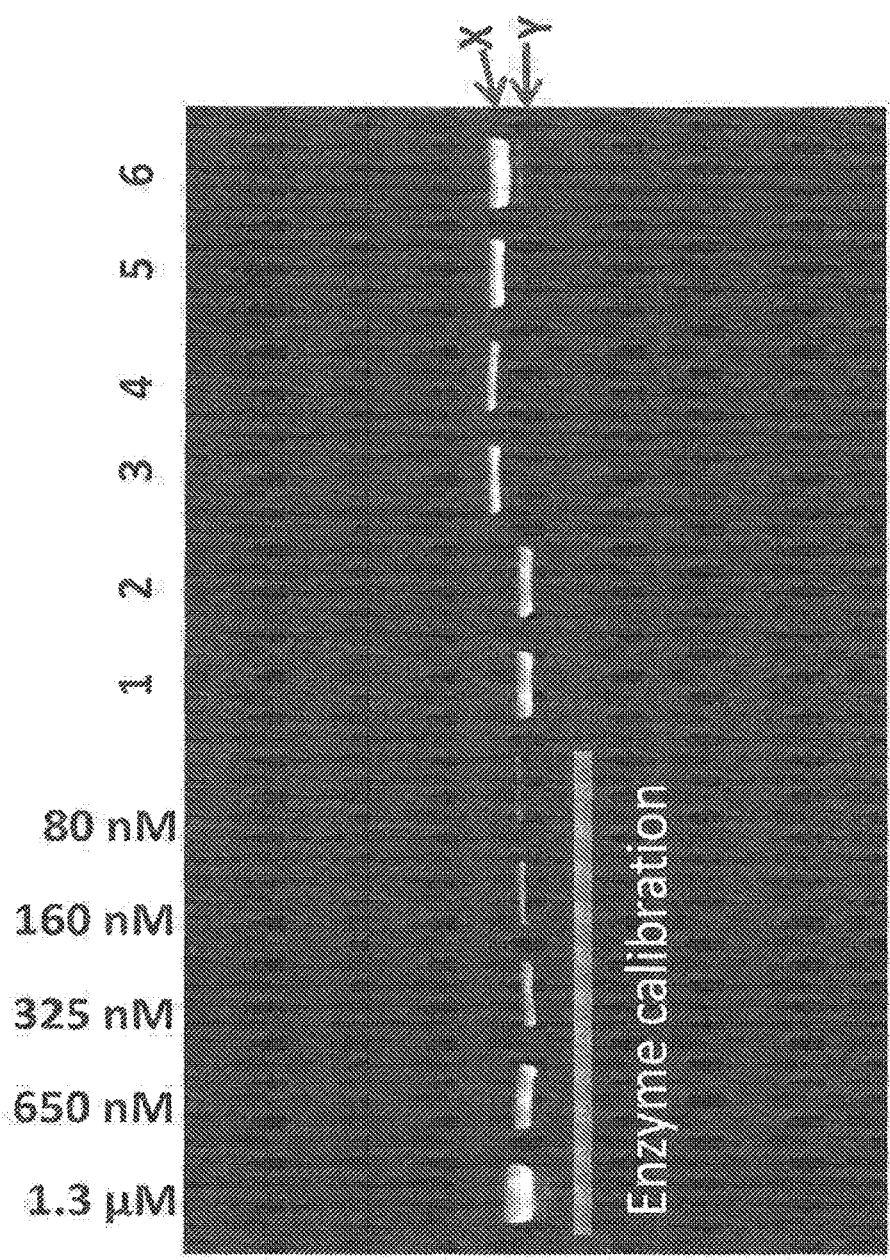
FIG. 4 shows the SDS PAGE gel analysis (the DNA calibration band corresponds to the DNA concentration shown at the top of the gel) column 1 shows the TrwC Cba-L376C/Q594A/K762C bound to the DNA Hairpin-adapter in buffer only (shown as band X), column 2 shows the TrwC Cba-L376C/Q594A/K762C bound to the DNA Hairpin-adapter after the TRIS buffer was added, column 3 shows the TrwC Cba-L376C/Q594A/K762C bound to the DNA Hairpin-adapter after the addition of Bismaleimideoethane, columns 4-6 show varying dilutions of TrwC Cba-L376C/Q594A/K762C bound to the DNA Hairpin-adapter after both FPLC purifications. Band Y corresponded to enzyme not closed on DNA. Band X corresponded to enzyme bound onto DNA by the Bismaleimideoethane linker.

Sample 2 was then further purified using a 5 mL Histrap HP column (FPLC) using the following elution buffers (Buffer C—20 mM Na-CAPS, 100 mM NaCl, 0.1% β-OTG, 1 mM TCEP, pH 10.0, Buffer D—20 mM Na-CAPS, 2M NaCl, 10% (w/v) glycerol, 0.1% β-OTG, 1 mM TCEP, pH 10.0 and Buffer E—20 mM Na-CAPS, 100 mM NaCl, 300 mM imidazole, 0.1% β-OTG, 1 mM TCEP, pH 10.0). Sample 2 was loaded onto the column and any DNA which did not have TrwC Cba-L376C/Q594A/K762C bound or enzyme which was not bound to DNA was washed off the column with buffer C. The column was then washed with Buffer D and then washed again with Buffer C. Finally the pre-bound TrwC Cba-L376C/Q594A/K762C to the DNA Hairpin-adapter was then eluted with 0-100% buffer E in ten column volumes. The main elution peak (an example is shown in FIG. 2 with the main peak labelled P2) was then pooled, the concentration measured and the DNA sample analysed using a TBE (Native) PAGE and an SDS PAGE gel. The TBE (native) PAGE was 4-20% TBE gel, run at 150 V for 25 minutes and then stained using SYBR gold stain. This stain allowed the visibility of any DNA in the sample (with or without enzyme bound). FIG. 3 shows this gel. Columns 4-6 show that after purification the DNA was still bound to the enzyme. The SDS PAGE was 10% Bis-Tris gel, XT MOPS, run at 200 V run for 60 min and then stained using SYPRO ruby stain. This stain allowed the visibility of any enzyme in the sample (bound or not bound to DNA). FIG. 4 shows in columns 4-6 that after purification the enzyme was closed onto the DNA using the Bismaleimideoethane linker.

Example 2

This example describes the sample preparation procedure for binding a polynucleotide binding protein to a loading moiety.
Materials and Methods
T4 Dda—E94C/C109A/C136A/A360C (3 µM, SEQ ID NO: 24 with mutations E94C/C109A/C136A/A360C) and DNA Y-adapter (500 nM, SEQ ID NO: 26 was hybridised to DNA strand X=30 iSpC3 spacers attached at the 3' end to the 5' end SEQ ID NO: 27 which is attached at the 3' end to 4 iSp18 spacers which are attached at the opposite end to the 5' end of SEQ ID NO: 28) were mixed in buffer (50 mM HEPES, 100 mM KOAc (pH 8) and EDTA (1 mM) and TMAD (100 µM) were added and incubated for 60 minutes at room temperature. The mixture was then diluted 1:1 in KCl/ATP solution (500 mM KCl, 1 mM ATP final) and incubated at ambient temperature for 25 mins, this mixture was known as sample 3.

This sample was then purified using SPRI beads. The SPRI beads were prepared using the procedure below
1. A serological pipette was used to transfer Wash Buffer (30 mL, 50 mM Tris pH7.5, 2.5 M NaCl) into a 50 mL Falcon tube.
2. The stock pot of Sera-Mag Speed Bead Carboxylate-Modified Magnetic Particles (Thermo) was vortexed to resuspend the beads.
3. The bead suspension (600 µL) was transferred into the 30 mL of Wash Buffer (Step 1) and vortexed to resuspend the beads.
4. The Falcon tube was then placed into DynaMag-50 magnetic rack, the beads were allowed to accumulate at the side of the tube adjacent to the magnet, and the supernatant was removed using a serological pipette.
5. A further 30 mL of Wash Buffer was added to the tube and the tube was vortexed thoroughly to resuspend the beads.
6. The Falcon tube was then placed back into the DynaMag-50 magnetic rack and the beads were allowed to accumulate at the side of the tube, adjacent to the magnet.
7. The supernatant was removed from the tube once the solution had cleared.
8. Steps 5, 6 and 7 were repeated in sequence three more times.
9. The Binding Buffer (30 mL, 50 mM Tris pH7.5, 2.5 M NaCl, 20% PEG8000) was added to the Falcon tube from Step 8 and the tube was then vortexed to resuspend the beads.

The beads were then stored at 4° C. prior to use, although they were used under ambient conditions during purification.
Sample 3 was Purified Using the Procedure Outlined Below
1. The tube from Step 9 above was then vortexed in order to resuspend beads, and 18.5 mL (of sample 3) was transferred into a clean 50 mL Falcon tube.
2. The tube was placed in DynaMag-50 magnetic rack and the beads were allowed to accumulate on the side of the tube, adjacent to the magnet. Note that since the beads were suspended in Binding Buffer (50 mM Tris pH7.5, 2.5 M NaCl, 20% PEG8000) the accumulation could have taken in excess of 10 minutes.
3. The supernatant was removed once the solution had cleared, 18.5 mL of Binding Buffer was added and the sample was vortexed thoroughly to resuspend the beads.
4. The tube was placed in a DynaMag-50 magnetic rack and the beads were allowed to accumulate on the side of the tube, adjacent to the magnet. Note that since the beads were suspended in Binding Buffer (50 mM Tris pH7.5, 2.5 M NaCl, 20% PEG8000) the accumulation of beads could have taken in excess of 10 minutes.
5. Step 3 was then repeated.
The sample was not pipette-mixed or vortexed from this point onwards.
6. The Falcon tube was placed back into a DynaMag-50 magnetic rack and the beads were allowed to accumulate on the side of the tube adjacent to the magnet. Note that since the buffer contained PEG8000, the accumulation of beads could have taken in excess of 10 minutes.
7. The supernatant was removed using a serological pipette and replaced with enough Binding Buffer to cover the beads (~25 mL).
8. The Falcon tube was left in the DynaMag-50 magnetic rack and the tube was rotated clockwise on its axis through 90°, allowing the accumulated beads to move around the sides of the tube until they settled at a new location adjacent to the magnets.
9. Step 8 was repeated three more times until the Falcon tube had returned to its original position.
10. The supernatant was removed using serological pipette, and then as much residual supernatant as possible was removed.
11. The Falcon tube was removed from the DynaMag-50 magnetic rack and Elution Buffer (2.5 mL, 20 mM NaCl, 50 mM Tris, pH7.5) was added.
12. The tube was gently agitated by flicking to resuspend the beads and then the sample was incubated under ambient conditions for 5 min.
13. The Falcon tube was returned to the DynaMag-50 magnetic rack, the beads were allowed to accumulate on the side of the tube adjacent to the magnets and supernatant was transferred to a 5 mL Protein LoBind microcentrifuge tube.
14. The eluted material from Step 13 was diluted two-fold through the addition of Elution Buffer.
15. The material was stored at 4° C. before it was aliquoted into tubes.

Figure 5:
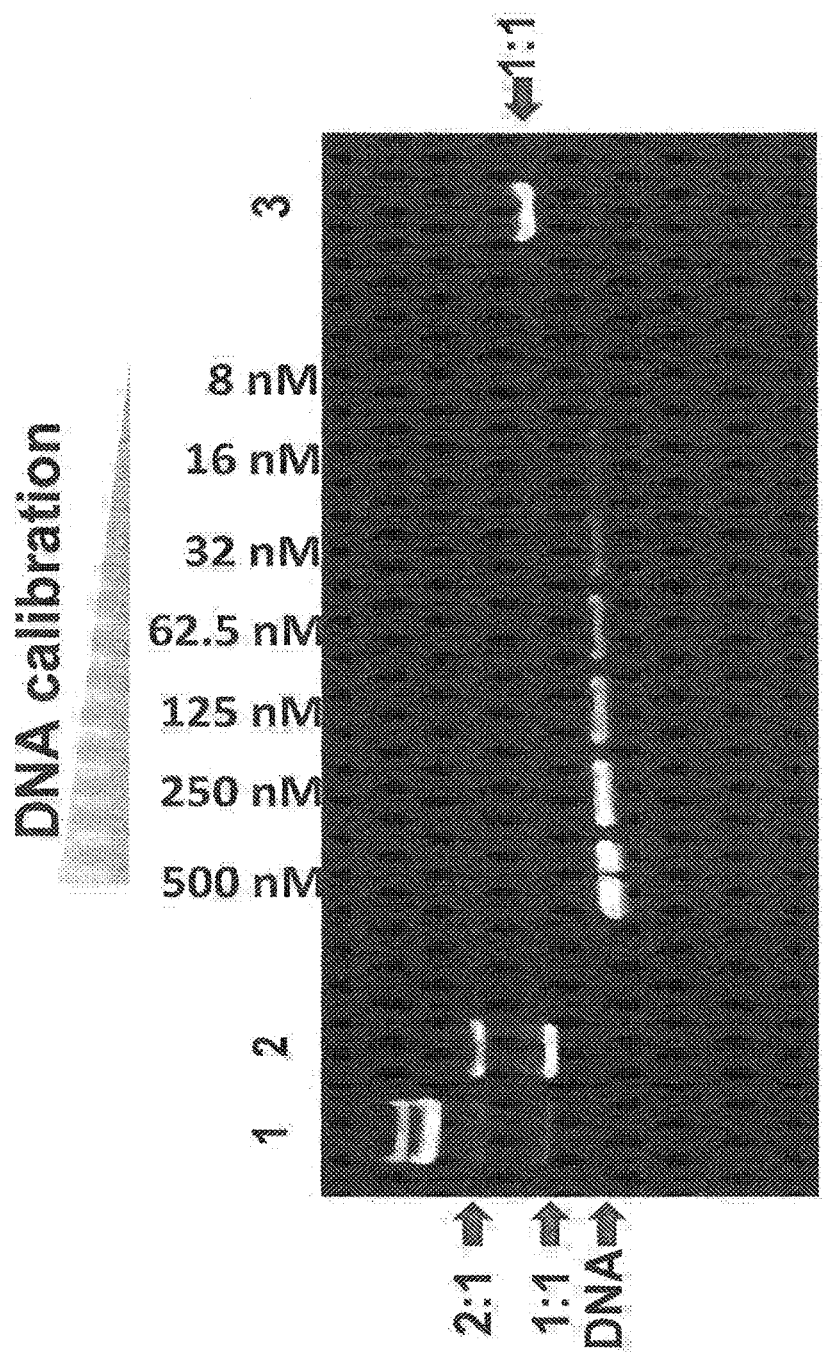
FIG. 5 shows the TBE (native) PAGE gel analysis (the DNA calibration band corresponds to the DNA concentration shown at the top of the gel) column 1 shows the T4 Dda—E94C/C109A/C136A/A360C bound to the DNA hairpin-adapter before TMAD was added. Column 2 shows the T4 Dda—E94C/C109A/C136A/A360C bound to the DNA hairpin-adapter after the KC1 and ATP were added, column 3 shows the T4 Dda—E94C/C109A/C136A/A360C bound to the DNA hairpin-adapter after the SPRI purification. Band 2:1 shows two enzymes bound, 1:1 shows one enzyme bound. The DNA band corresponded to DNA alone.

The resultant enzyme bound to DNA was then analysed using a TBE PAGE gel as described previously in Example 1 except the gel was run for 45 mins. The gel is shown in FIG. 5 and column 3 shows the SPRI purification purified a single enzyme bound to the DNA Y-adapter.

Example 3

This example describes the sample preparation procedure for ligation of the enzyme pre-bound to the Y-adapter and the enzyme bound to the hairpin adapter to a random strand of genomic double-stranded DNA.
Materials and Methods The random genomic double-stranded DNA sequence was dA tailed using a NEBNext dA-tailing module (NEB). No further purification was necessary. The dA-tailed genomic DNA (30 µL) was mixed with Y-adapter DNA with T4 Dda—E94C/C109A/C136A/A360C pre-bound (10 µL 200 nM) and hairpin-adapter with TrwC Cba-L376C/Q594A/K762C pre-bound (10 µL, 1 µM) and Blunt/TA ligase master mix (50 µL) and the sample was inverted 10 times to mix. The sample was then briefly spun down in a microfuge. The sample was then incubated for 10 mins at room temperature. The adapted DNA was purified using 0.4× Agencourt AMPure XP beads by volume, following the manufacturer's protocol, but using the following Wash Buffer (750 mM NaCl, 10% PEG 8000, 50 mM Tris.HCl pH 8) and Elution Buffer (40 mM CAPS pH 10, 40 mM KCl along with appropriate DNA tethers) as detailed below.

After following the manufactures protocol the pelleted beads were bathed in 150 µl Wash Buffer for 30 sec. The Wash Buffer was then carefully aspirated taking care not to disturb the pellet. The sample was then briefly spun in a microfuge, in order to sufficiently drain excess Wash Buffer from the beads. The tube was then replaced on the magnet to pellet the beads and then left for approximately 1-2 min. Finally the remaining Wash Buffer was then aspirated and the pelleted beads resuspended in 25 µl of Elution Buffer and mixed thoroughly. The sample was then left for 10 min before pelleting and removing the eluate. Finally, a DNA strand with a cholesterol attached at one end was hybridised to the sample. This was the sample DNA which was then tested in Example 4.

Example 4

Figure 6:
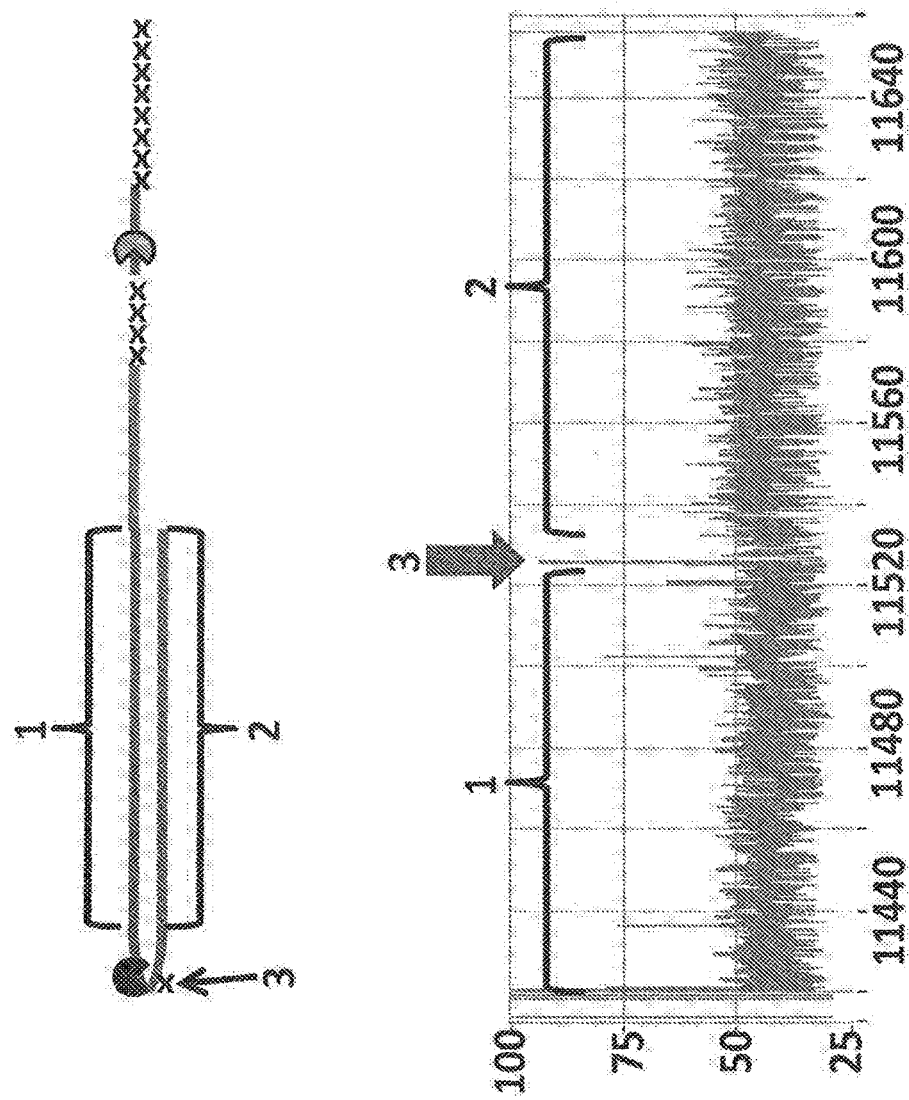
FIG. 6 shows an example current trace of when helicases T4 Dda—E94C/C109A/C136A/A360C and TrwC Cba-L376C/Q594A/K762C controlled the translocation of the DNA construct (see above current trace) through an MspA nanopore. The x-axis corresponds to the time (s) and the y-axis corresponds to the current (pA). The trace showed a single DNA strand moving through the nanopore under the control of the two helicases, the labelled regions 1 and 2 corresponded to the translocation of region 1 and 2 of the DNA construct. The trace shows a current trace observed when construct Y was translocated through the pore under the control of both T4 Dda—E94C/C109A/C136A/A360C and TrwC Cba-L376C/Q594A/K762C helicases. The arrow labelled 3 shows a spike in current as the spacers in the hairpin adapter translocated through the nanopore. The hairpin adapter and Y adaptor spacers are shown as an x in the DNA construct picture above the current trace.

This example illustrated that after the above sample preparation procedure the DNA construct which was produced had functioning pre-bound enzymes (T4 Dda—E94C/C109A/C136A/A360C and TrwC Cba-L376C/Q594A/K762C) which were capable of controlling the movement of the DNA through an MspA nanopore.
Materials and Methods The DNA construct produced in Example 3 (final concentration added to the nanopore system 0.1 nM) which had both enzymes pre-bound (see FIG. 6 data) was added to buffer (final concentrations added to the nanopore system were 500 mM KCl, 25 mM potassium phosphate pH 8.0), ATP (final concentration added to the nanopore system 2 mM) and MgCl2 (final concentration added to the nanopore system 2 mM). This was the pre-mix which was then added to the nanopore system (total volume 150 µL).

Electrical measurements were acquired from single MspA nanopores inserted in block co-polymer in buffer (25 mM potassium phosphate, 150 mM potassium ferrocyanide (II), 150 mM potassium ferricyanide (III), pH 8.0). After achieving a single pore inserted in the block co-polymer, then buffer (2 mL, 25 mM potassium phosphate, 150 mM potassium ferrocyanide (II), 150 mM potassium ferricyanide (III), pH 8.0) was flowed through the system to remove any excess MspA nanopores. The enzyme pre-bound to construct Y (with both enzymes T4 Dda—E94C/C109A/C136A/A360C and TrwC Cba-L376C/Q594A/K762C prebound), fuel (MgCl2 and ATP) pre-mix (150 µL total) was then flowed into the single nanopore experimental system and the experiment run at a holding potential of −120 mV for 6 hours (with potential flips to +60 mV for 2 seconds) and helicase-controlled DNA movement monitored.
Results Helicase controlled DNA movement was observed for the DNA construct Y using both T4 Dda—E94C/C109A/C136A/A360C and TrwC Cba-L376C/Q594A/K762C in tandem (see FIG. 6). The Figure shows the controlled translocation of regions 1 and 2 labelled in the figure, which corresponded to the random genomic double stranded DNA. When the spacers which were present in the hairpin adapter translocated through the nanopore increased current flow was observed see label 3. Therefore this sample helicase controlled DNA movement showed that the sample preparation procedure was successful as regions 1 and 2 translocated through the nanopore under the control of the enzymes and the increased current flow spike was used to clearly identify the transition between the regions.

Example 5: MuA Pre-Loaded Enzyme Adapter

In this example we showed that Enzyme can be pre-bound to the MuA Adaptor and this does not affect the function of MuA i.e., MuA can still attach the adaptor to the DNA.

T4 Dda—E94C/C109A/C136A/A360C (SEQ ID NO: 24 with mutations 4C/C109A/C136A/A360C) was pre-bound to the MuA Y-adapter: As illustrated in FIG. 7, the adapter peak shifts (left is non-prebound and right is prebound).

Tagmentation uses a transposase to fragment and attach adapters to genomic DNA. The conditions for tagmentation were as follows: The adapter was pre-loaded with Enzyme. Tagmentation was carried out using: 100 nM MuA Tetramer with 400 nM T4 Dda—E94C/C109A/C136A/A360C (SEQ ID NO: 24 with mutations 4C/C109A/C136A/A360C) pre-bound adapter. 25 ng ul-1 Target lambda DNA. 25 mM Tris-HCl pH 8.0 at 20° C., 10 mM MgCl2, 110 mM NaCl, 0.05% Triton X-100, 10% glycerol 30° C. for 1 hour.

To visualise on Agilent Bioanalyser, T4 Dda—E94C/C109A/C136A/A360C (SEQ ID NO: 24 with mutations 4C/C109A/C136A/A360C) and MuA were heat inactivated at 75° C. for 10 mins. As illustrated in FIG. 8, no adverse effect was seen on the Tagmentation of the target DNA. This can be seen by the fact the target DNA smears (left is non-prebound and right is prebound). The results show that it does not matter if Enzyme was attached, the fragmented genomic DNA has the same distribution of fragment sizes.

Figure 9:
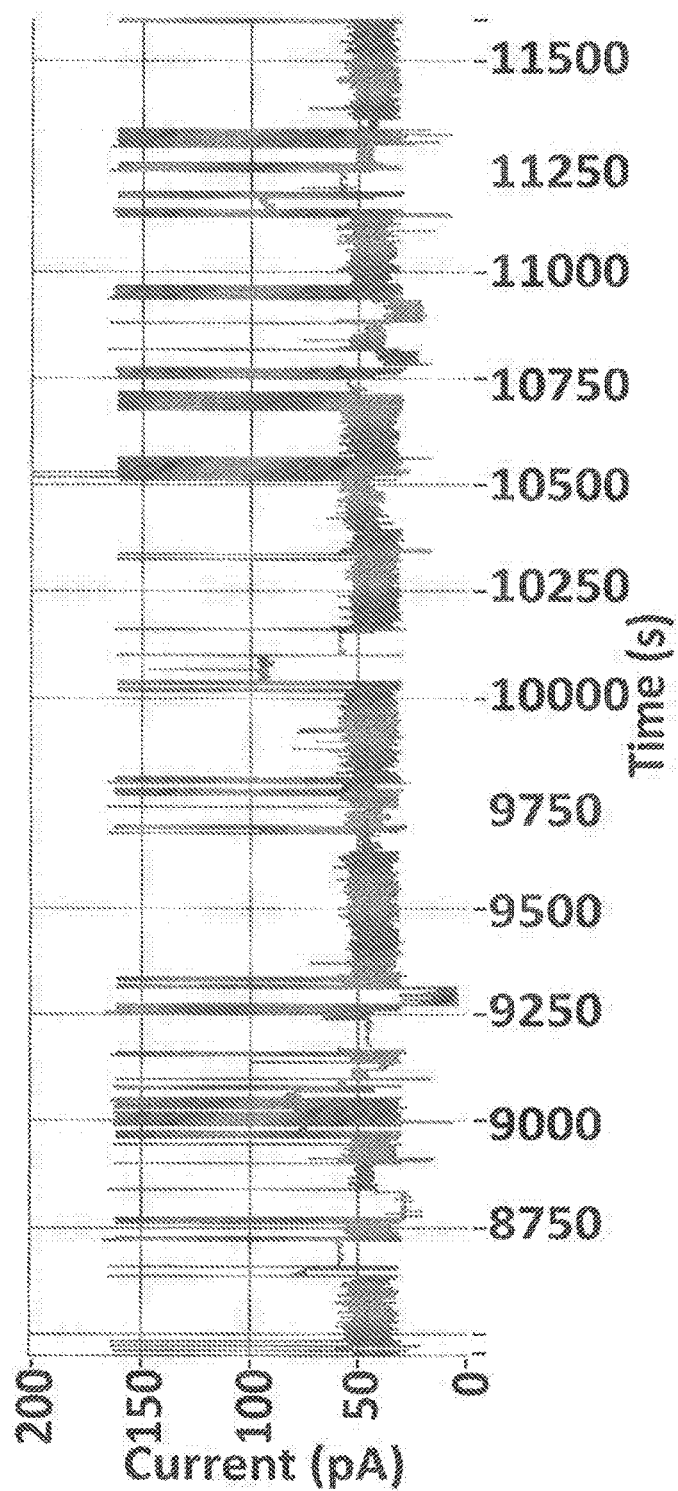
FIG. 9 shows an example current trace of when a helicase controlled the movement of DNA through a nanopore that was prepared using DNA produced by MuA tagmentation.

The DNA sample produced using the tagmentation protocol described previously was tested using a similar procedure as described in Example 4 using only T4 Dda—E94C/C109A/C136A/A360C as the helicase. As shown in FIG. 9, the resultant sample library can be added onto a chip directly and helicase controlled DNA movement was observed.

Example 6

Example describes loading of two different enzymes onto two DNA components, which were then ligated together and attached to genomic DNA. The example below describes the loading of two different enzymes, however, this procedure is equally applicable for attaching two enzymes which are the same.

Materials and Methods

Figure 10:
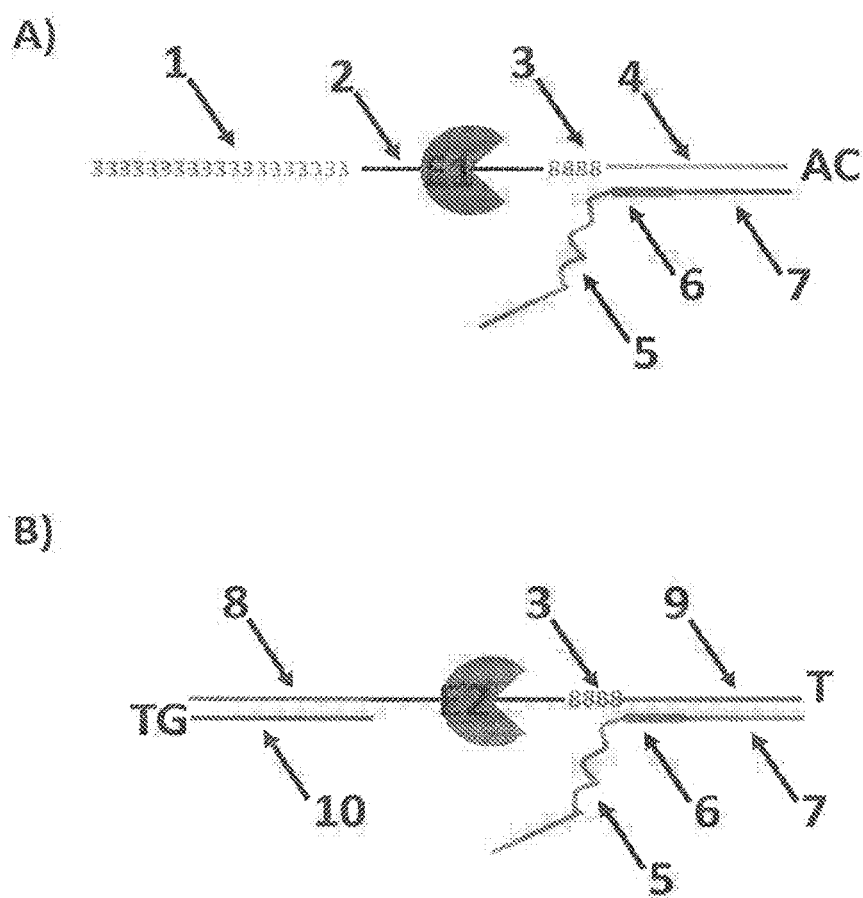
FIG. 10 shows the A-piece (see section A) and the END-piece (see section B) loading moieties which have E1 (A-piece) and E2 (END-piece) pre-bound. These two loading moieties are ligated to genomic DNA in Example 6. The A-piece has a region of 39 SpC3 spacers labelled 1. SEQ ID NO: 32 corresponded to the region labelled 2, this was the region to which E1 bound. The regions labelled 3 corresponded to four iSp18 spacers. The region labelled 4 corresponded to SEQ ID NO: 33. The regions labelled 5 corresponded to SEQ ID NO: 34. The regions labelled 6 corresponded to one iBNA-meC, two iBNA-A and two iBNA-meC. The regions labelled 7 corresponded to SEQ ID NO: 35. The region labelled 8 in the END-piece corresponded to SEQ ID NO: 36. The region labelled 9 corresponded to SEQ ID NO: 37. The region labelled 11 corresponded to SEQ ID NO: 38.

The same protocol as described in Example 2 was followed and two enzymes (E1=T4 Dda-(H82R/E94C/A360C) (SEQ ID NO: 24 with mutations H82R/E94C/A360C) and E2=T4 Dda—E94C/C109A/C136A/A360C (SEQ ID NO: 24 with mutations E94C/C109A/C136A/A360C) in FIG. 10) were separately loaded onto two DNA constructs (A-piece and END-piece in FIG. 10), and subsequently purified as described in Example 2. The A-piece comprised two DNA oligos hybridized together (see the figure legend of FIG. 10 for a full description of this oligonucleotide). The END-piece comprised three DNA oligos hybridized together (see the figure legend of FIG. 10 for a full description of this oligonucleotide).

The purified enzyme-loaded A-piece and END-piece DNA adapters were then ligated to a 3.6 kb section of genomic lambda dsDNA (template and complement SEQID), along with the hairpin adapter 3 (SEQ ID NO: 39 with a 5' phosphate which was attached at the 3' end to four iSpC3 spacers which are attached at the opposite end to the 5' end of SEQ ID NO: 40) using the protocol described below.

The 3.6 kb genomic DNA (0.34 µL, 5 nM final, SEQ ID NO: 41 hybridised to SEQ ID NO: 42) was mixed with A-piece E1-DNA (6.25 uL, 50 nM final) END-piece E2-DNA (3.125 uL, 25 nM final), hairpin 3 (1.25 uL, 25 nM final) with ligation buffer (5 uL, 2 mM ATPγS, 4 mM MgCl2, 10 mM Hepes pH8.0, 6% PEG 8000, 10 mM NaCl final), Quick T4 DNA Ligase NEB (2.5 uL, 200 U/uL final) and nuclease free water (8 uL). The sample was incubated for 10 mins at room temperature. Finally, a DNA strand with a cholesterol attached at one end was hybridised to the sample. The sample 4 was not purified further and used in nanopore electrophysiology as described in Example 4.

Results

Figure 11:
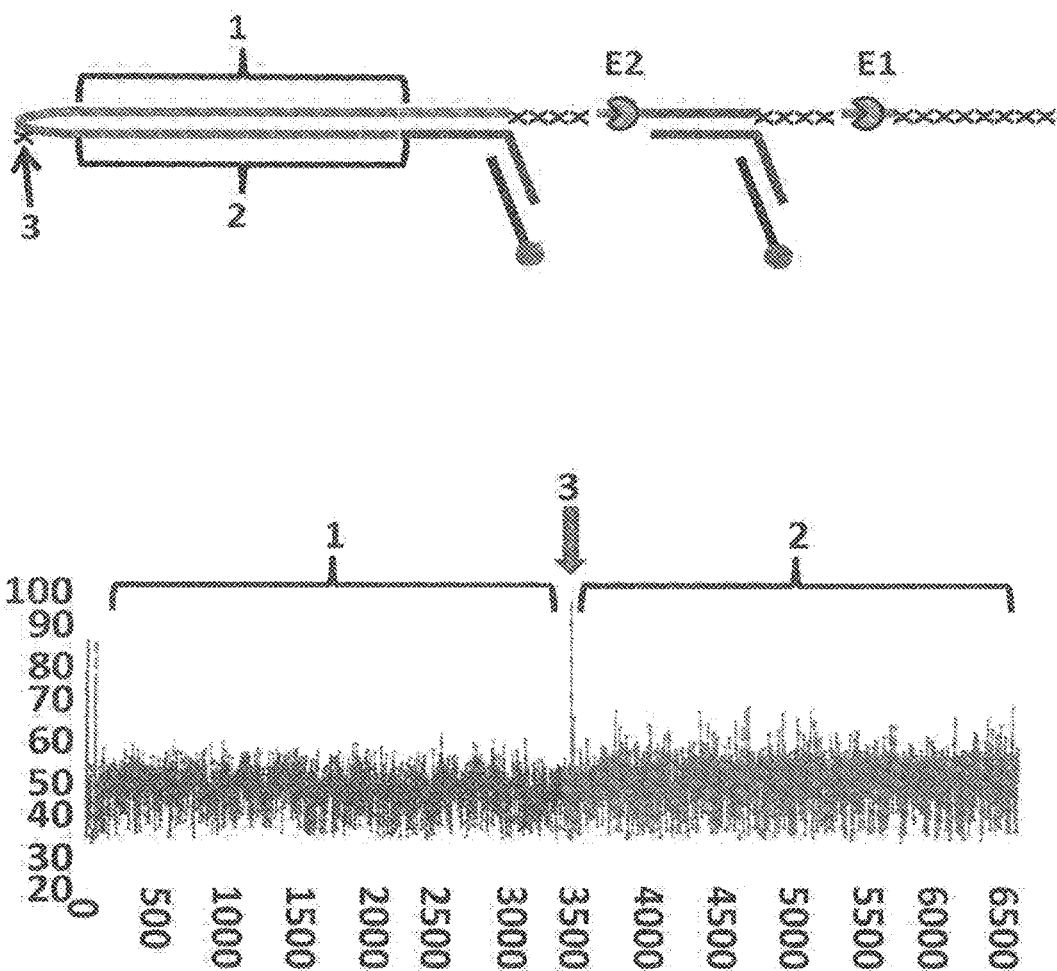
FIG. 11 shows an example plot of when helicases T4 Dda-(H82R/E94C/A360C) (SEQ ID NO: 24 with mutations H82R/E94C/A360C, E1) and T4 Dda—E94C/C109A/C136A/A360C (SEQ ID NO: 24 with mutations E94C/C109A/C136A/A360C, E2) controlled the translocation of the DNA construct in sample 4 (shown at the top of the figure) through an MspA nanopore. The x-axis corresponds to the movement index and the y-axis corresponds to the current (pA). For each DNA strand which moved through the pore the current was measured as a function of time. The moving DNA resulted in stepwise changes in the measured current levels. The observed current levels were fitted to obtain a mean current for each step and assigned an incrementing movement index point. The mean current against movement index therefore closely approximated the original current signal and was used to characterise the translocated DNA. The plot showed a single DNA strand moving through the nanopore under the control of the two helicases, the labelled regions 1 and 2 corresponded to the translocation of region 1 and 2 of the DNA construct. The trace shows the movement index observed when the construct was translocated through the pore under the control of both T4 Dda-(H82R/E94C/A360C) and T4 Dda—E94C/C109A/C136A/A360C helicases. The arrow labelled 3 shows a spike in current as the spacers in the hairpin adapter translocated through the nanopore. The hairpin adapter and Y adaptor spacers are shown as an x in the DNA construct picture above the trace.

Helicase controlled DNA movement was observed for the DNA construct in sample 4 (see DNA construct shown in FIG. 11) using both T4 Dda-(H82R/E94C/A360C) and T4 Dda—E94C/C109A/C136A/A360C in tandem (see FIG. 11). The Figure shows the controlled translocation of regions 1 and 2 labelled in the figure, which corresponded to the genomic double stranded DNA. When the spacers which were present in the hairpin adapter translocated through the nanopore increased current flow was observed see arrow label 3. Therefore this sample helicase controlled DNA movement showed that the sample preparation procedure was successful as regions 1 and 2 translocated through the nanopore under the control of the enzymes and the increased current flow spike was used to clearly identify the transition between the regions.

Example 7

This example describes pre-loading a helicase and a polymerase onto a loading moiety, which was then ligated to a 3.6 kB strand of DNA. The polymerase was then used to make a copy of both the template and the complement strands of the 3.6 kB strand of DNA. A cartoon representation of the ligation and polymerisation steps is shown in FIG. 17.

Materials and Methods

Figure 12:
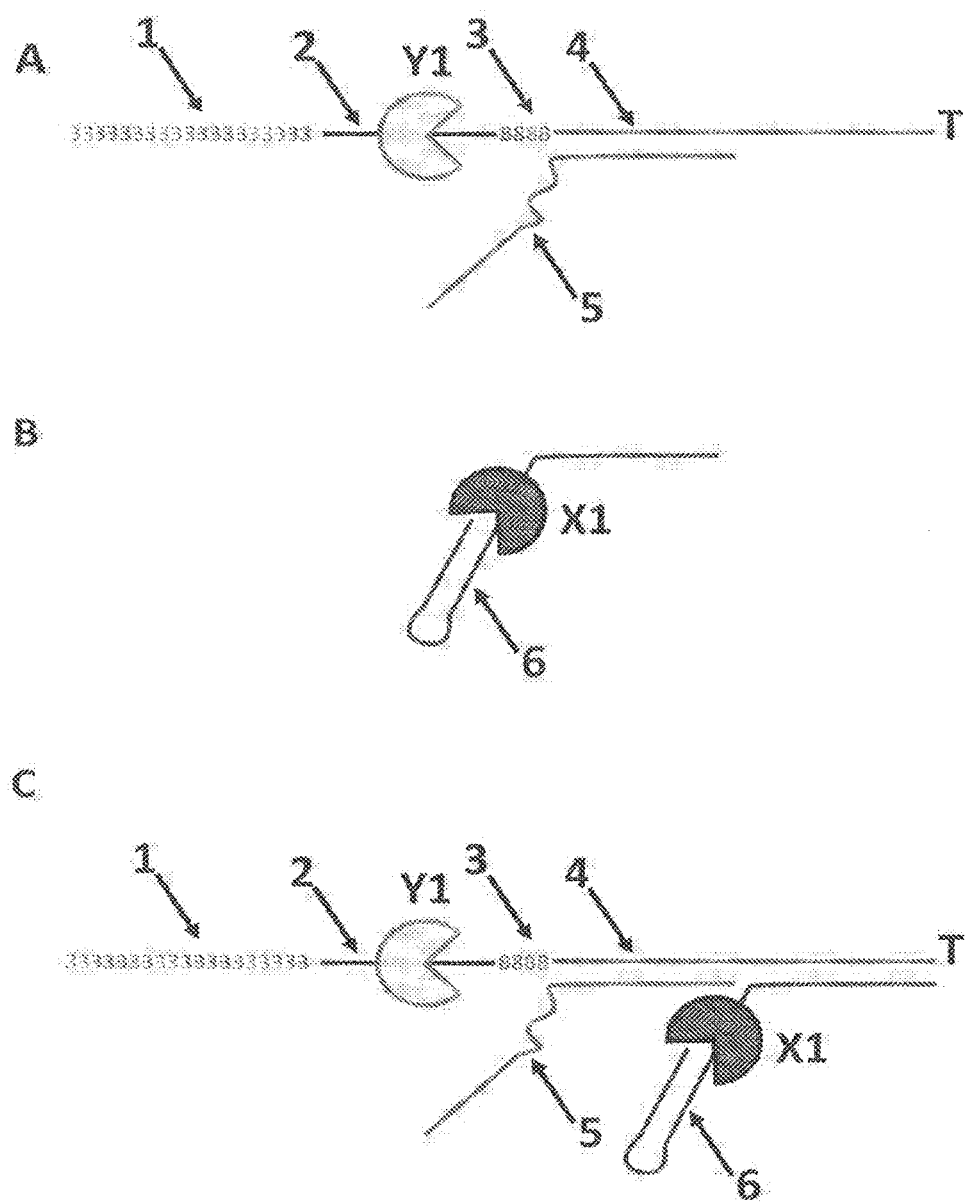
FIG. 12 shows the helicase-leader complex (see section A), the polymerase strand complex (see section B) and the final loading moiety the helicase/polymerase leader complex which had both a polymerase (labelled. Xl, Phi29-A411C/Q560C (SEQ ID NO: 9 with mutations A411C/Q560C)) and a helicase (labelled Y1, and T4 Dda—E94C/C109A/C136A/A360C (SEQ ID NO: 24 with mutations E94C/C109A/C136A/A360C)) pre-bound. This final loading moiety was ligated to a 3.6 kb DNA strand (SEQ ID NO: 46) in Example 7. The regions labelled 1 corresponded to 30 SpC3 spacers. SEQ ID NO: 27 corresponded to the regions labelled 2, this was the region to which T4 Dda—E94C/C109A/C136A/A360C bound. The regions labelled 3 corresponded to four iSp18 spacers. The regions labelled 4 corresponded to SEQ ID NO: 28. The regions labelled 5 corresponded to SEQ ID NO: 43. The regions labelled 6 corresponded to SEQ ID NO: 44 which was attached at its 3' end to four iSpC3 spacers which were attached at the opposite end to the 5' end of SEQ ID NO: 45. Phi29-A411C/Q560C bound to region 6.
Figure 15:
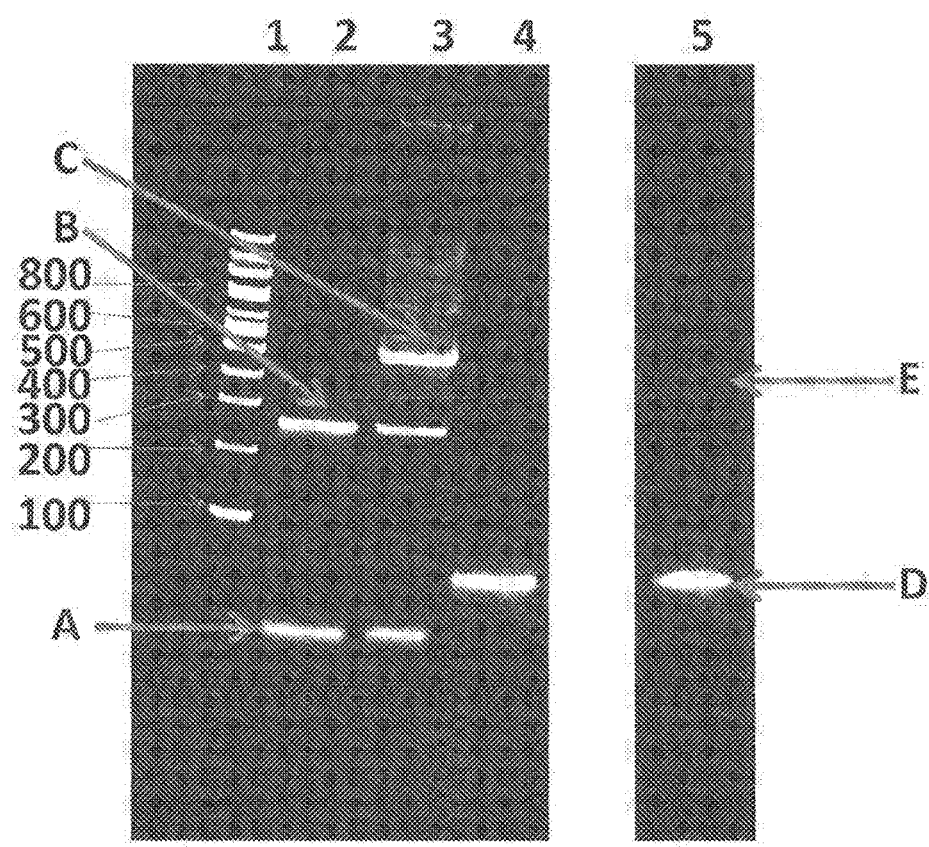
FIG. 15 shows a 4-20% TBE PAGE which was run at 200V for 60 minutes and then stained using SYBR. Each sample run on the gel was 400 nM (5 µL). Lane 1 corresponded to a 100 bp ladder (the number of base pairs that the bands correspond to is shown along the side of the gel). Lane 2 corresponded to helicase leader complex shown in FIG. 12A, without the helicase bound. Lane 3 corresponded to the helicase leader complex shown in FIG. 12A with the helicase bound. Lane 4 corresponded to the polymerase strand complex shown in FIG. 12B without the polymerase bound. Lane 5 corresponded to the polymerase strand complex shown in FIG. 12B with the polymerase bound. Band A corresponded to SEQ ID NO: 43. Band B corresponded to DNA strand X=30 iSpC3 spacers attached at the 3' end to the 5' end SEQ ID NO: 27 which is attached at the 3' end to 4 iSp18 spacers which are attached at the opposite end to the 5' end of SEQ ID NO: 28. Band C corresponded to the helicase (T4 Dda—E94C/C109A/C136A/A360C) bound to DNA strand X. Band D corresponded to the polymerase strand complex without the enzyme bound (SEQ ID NO: 44 which was attached at its 3' end to four iSpC3 spacers which were attached at the opposite end to the 5' end of SEQ ID NO: 45). Band E corresponded to Phi29-A411C/Q560C bound to the polymerase strand complex.
Figure 16:
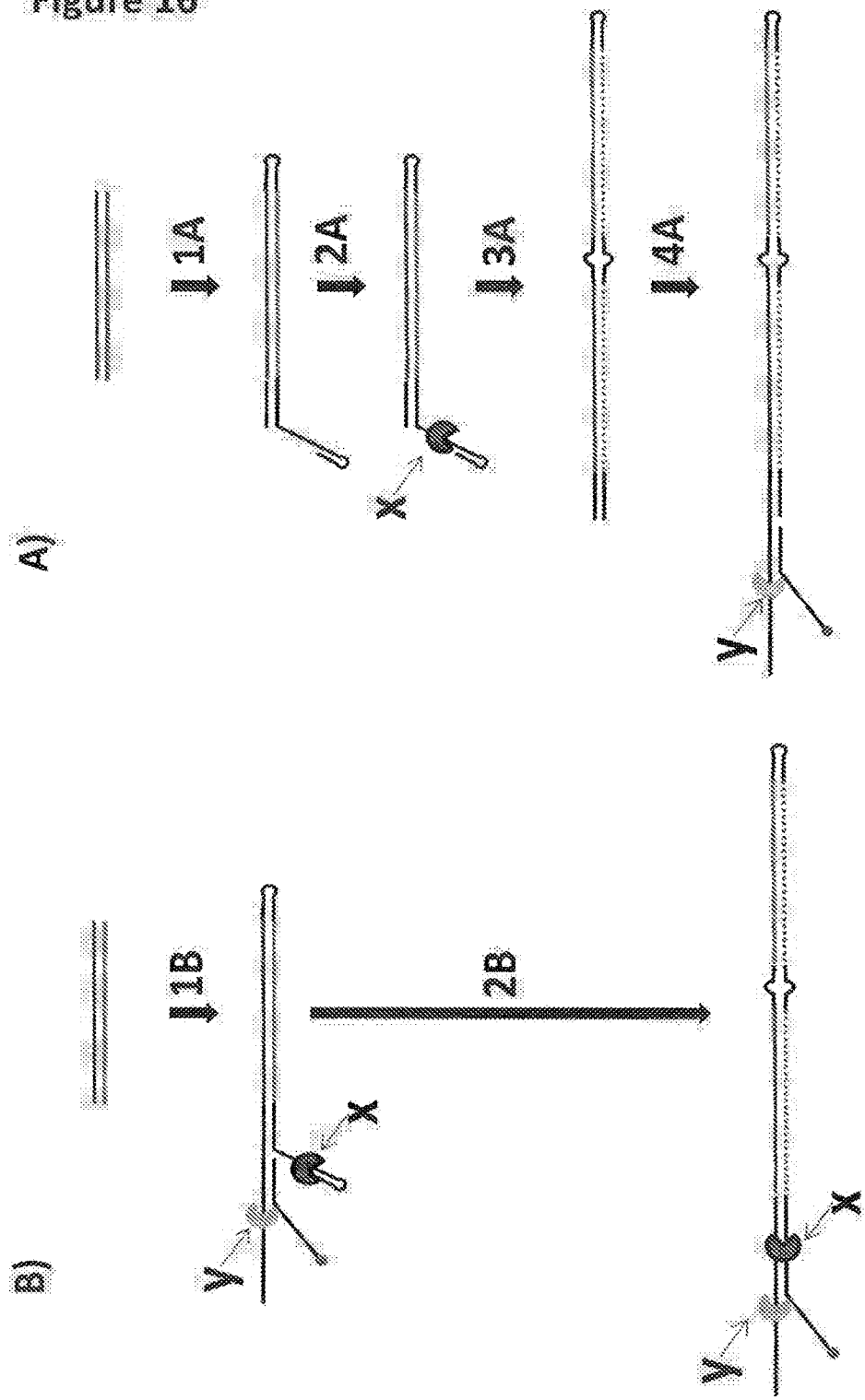
FIG. 16 shows in A) an example of a method for ligation of adapters and polymerisation of a double-stranded target polynucleotide without pre-binding the polymerase (labelled x) to a loading moiety prior to ligation and B) shows an example of the method of the invention of ligation of a loading moiety with both a pre-bound helicase (labelled y) and a pre-bound polymerase (labelled x) and then polymerisation of the double-stranded target polynucleotide. Step 1A shows ligation of adapters to either end of the double-stranded target polynucleotide. Step 2A shows binding of a polymerase (labelled x). Step 3A shows polymerisation of the double stranded target polynucleotide, the polynucleotide formed using the target as a template is shown as a dotted line. Step 4A shows end repair of the new double-stranded construct, A-tailing of the construct and ligation of a loading moiety with a pre-bound helicase (labelled y). Step 1B shows ligation of a loading moiety which contained both a pre-bound helicase (labelled y) and a pre-bound polymerase (labelled x). Step 2B shows polymerisation of the double-stranded target polynucleotide. No further steps were required in B, therefore, this process involved significantly fewer steps than the process shown in A.

The helicase-leader complex (diagram shown in FIG. 12 section A) was prepared as described in Example 2, except SEQ ID NO: 26 is replaced with SEQ ID NO: 43. FIG. 15 lane 3 shows this sample run on a TBE PAGE showing the enzyme had bound to the DNA (band labelled c).

The polymerase-strand complex (diagram shown in FIG. 12 section B) was prepared by pre-binding Phi29-A411C/Q560C (SEQ ID NO: 9 with mutations A411C/Q560C, labelled X1) onto the DNA hairpin strand (SEQ ID NO: 44 attached at its 3' end to four iSpC3 spacers which are attached at the opposite end to the 5' end of SEQ ID NO: 45). Phi29-A411C/Q560C was buffer exchanged using Zeba 0.5 ml desalting columns (89882, Piercenet) in accordance with the protocol (https://www.piercenet.com/instructions/2161515.pdf) into the following buffer (50 mM tris pH 8, 20 mM (NH4)2SO4, 10 mM MgCl2, 4% glycerol) and diluted to 400 nM. The DNA hairpin strand (SEQ ID NO: 44 attached at its 3' end to four iSpC3 spacers which are attached at the opposite end to the 5' end of SEQ ID NO: 45) was added to the Phi29-A411C/Q560C which produced a sample (400 nM) with a 1:1 ratio of Phi29-A411C/Q560C:DNA hairpin strand (this sample corresponded to band E in FIG. 15). This was incubated for 15 minutes at room temperature. TMAD (125 uM) was then added and the sample incubated for a further 15 minutes at room temperature. The sample was then buffer exchanged again as described previously except the buffer used was (10 mM HEPES pH8, 10 mM MgCl2). This sample was then mixed 1:1 with helicase-leader complex (the helicase-leader complex corresponded to band C in FIG. 15) to create the helicase/polymerase leader complex shown in section C of FIG. 12.

Figure 13:
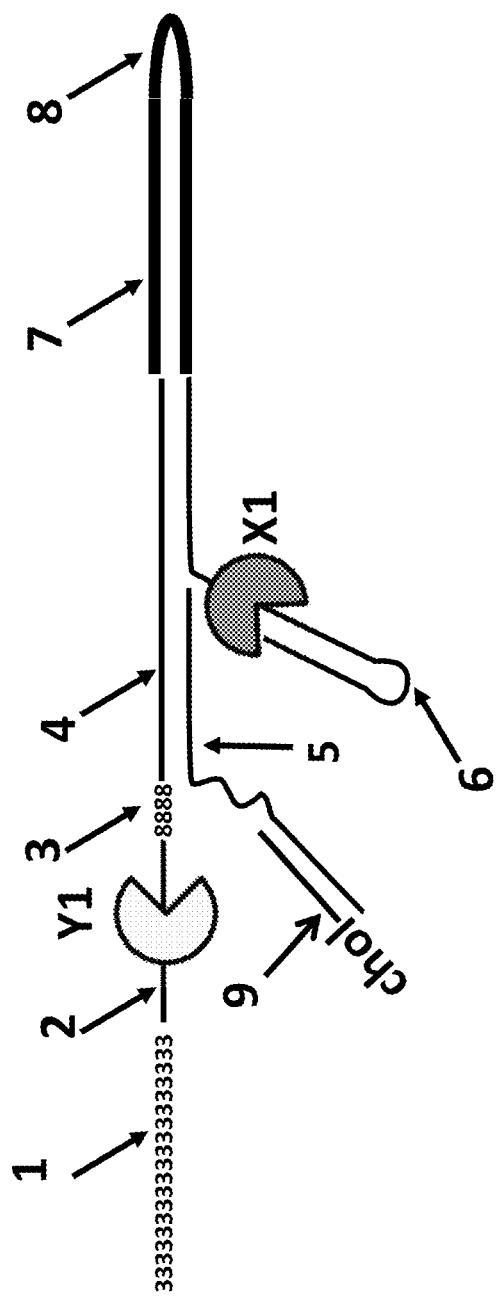
FIG. 13 shows the DNA construct which was produced after the ligation step and before the polymerisation step in Example 7. The region labelled 1 corresponded to 30 SpC3 spacers. SEQ ID NO: 27 corresponded to the region labelled 2, this was the region to which T4 Dda—E94C/C109A/C136A/A360C bound. The regions labelled 3 corresponded to four iSp18 spacers. The regions labelled 4 corresponded to SEQ ID NO: 28. The regions labelled 5 corresponded to SEQ ID NO: 43. The regions labelled 6 corresponded to SEQ ID NO: 44 which was attached at its 3' end to four iSpC3 spacers which were attached at the opposite end to the 5' end of SEQ ID NO: 45. Phi29-A411C/Q560C bound to region 6. Region 7 corresponded to SEQ ID NO: 46. Region 8 corresponded to SEQ ID NO: 47. Region 9 corresponded to SEQ ID NO: 31.

The helicase/polymerase leader complex was ligated onto the 3.6 kb DNA strand (SEQ ID NO: 46) at 2:1 excess, with 2:1 excess of hairpin (SEQ ID NO: 47). Ligation was carried out in 5×ATP ligation buffer (5×: 150 mM Tris pH8, 50 mM MgCl2, 5 mM ATP, 30% PEG 8000) in the presence of 10% T4 quick ligase. The sample was incubated for 15 mins at room temperature. The construct produced after the ligation step is shown in FIG. 13. For the polymerase fill-in step, dNTPs (0.5 mM) were added. The sample was then incubated at 30° C. for 1 hour. Finally, SEQ ID NO: 31 was added at a 5× excess to the sample and the sample incubated from a minimum of 15 mins at room temperature.

The final sample 5 was not purified further and used in nanopore electrophysiology as described in Example 4.

Results

Figure 14:
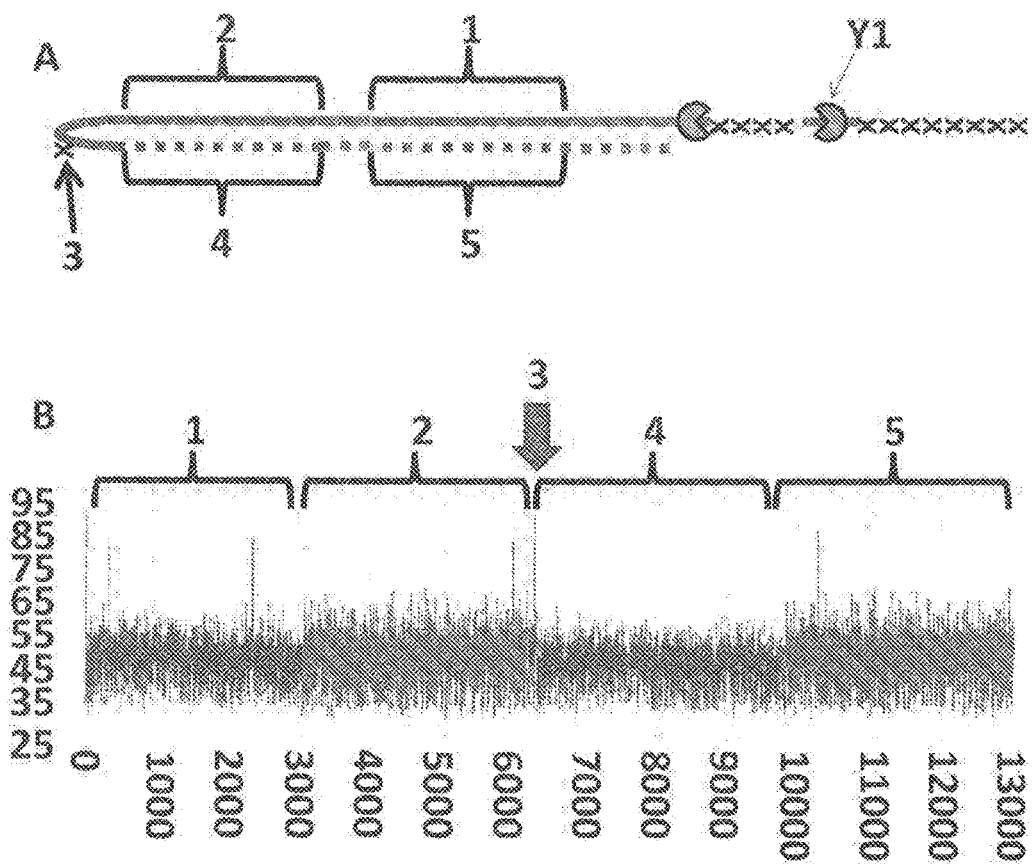
FIGS. 14 A and B show an example plot (shown in FIG. 14B) of when the helicase T4 Dda-E94C/C109A/C136A/A360C (labelled Y1) controlled the translocation of the DNA construct in sample 5 (shown in FIG. 14A) through an MspA nanopore. The x-axis in FIG. 14B corresponds to the movement index and the y-axis corresponds to the current (pA). For each DNA strand which moved through the pore the current was measured as a function of time. The moving DNA resulted in stepwise changes in the measured current levels. The observed current levels were fitted to obtain a mean current for each step and assigned an incrementing movement index point. The mean current against movement index therefore closely approximated the original current signal and was used to characterise the translocated DNA.

Helicase controlled DNA movement was observed for the DNA construct in sample 5 (see DNA construct shown in FIG. 13) using T4 Dda—E94C/C109A/C136A/A360C in (see FIG. 14). The Figure shows the controlled translocation of regions 1, 2, 4 and 5 labelled in the figure, which corresponded to the original 3.6 kB DNA strand (section 1 and 2) and the complementary strand produced by the polymerase (section 4 and 5). When the spacers which were present in the hairpin of the final construct (shown as x and labelled 3 in the top construct diagram of FIG. 14) translocated through the nanopore increased current flow was observed see arrow label 3. Therefore this sample helicase controlled DNA movement showed that the sample ligation and polymerisation preparation procedure was successful as regions 1, 2 and polymerised regions 4 and 5 translocated through the nanopore under the control of the enzyme and the increased current flow spike was used to clearly identify the transition between the original strand regions and the polymerised strand regions.

The invention claimed is:

1. A method for attaching one or more polynucleotide binding proteins to a target polynucleotide, comprising:
   (a) providing the one or more polynucleotide binding proteins bound to one or more loading moieties; and
   (b) covalently attaching the one or more loading moieties to the target polynucleotide.

2. A method according to claim 1, wherein the method comprises before step (a) binding the polynucleotide binding proteins to the one or more loading moieties.

3. A method according to claim 1, wherein the one or more polynucleotide binding proteins are polynucleotide handling enzymes.

4. A method according to claim 3, wherein the one or more polynucleotide handling enzymes are one or more polymerases, exonucleases, helicases, topoisomerases or a combination thereof.

5. A method according to claim 4, wherein the one or more helicases are Hel308 helicases, RecD helicases, XPD helicases or Dda helicases.

6. A method according to claim 5, wherein the one or more helicases are modified to reduce the size of an opening in the polynucleotide binding domain through which in at least one conformational state the polynucleotide can unbind from the helicase.

7. A method according to claim 1, wherein the one or more polynucleotide binding proteins remain bound to the one or more loading moieties at the end of the step (b).

8. A method according to claim 1, wherein (i) the one or more loading moieties are synthetic; and/or (ii) the one or more loading moieties comprise a loading polynucleotide; and/or (iii) the one or more loading moieties comprise a single stranded polynucleotide to which the one or more polynucleotide binding proteins are bound.

9. A method according to claim 1, wherein the target polynucleotide is a double stranded polynucleotide.

10. A method according to claim 9, wherein the at least one of the one or more loading moieties is a Y adaptor.

11. A method according to claim 9, wherein at least one of the one or more loading moieties is a bridging moiety.

12. A method according to claim 11, wherein the bridging moiety is a hairpin loop.

13. A method according to claim 1, wherein the one or more loading moieties comprise one or more anchors that are capable of coupling to a membrane.

14. A method according to claim 1, wherein the one or more loading moieties is a loading polynucleotide and step (b) comprises attaching the one or more loading moieties to the target polynucleotide using a ligase.

15. A method according to claim 14, wherein the method further comprises (c) removing the ligase from method conditions.

16. A method according to claim 14, wherein step (b) is performed in the absence of ATP or using gamma-S-ATP (ATPγS) instead of ATP.

17. A method of characterising a target polynucleotide, comprising:
   (a) carrying out a method according to claim 1;
   (b) contacting the target polynucleotide having the one or more attached polynucleotide binding proteins as provided in step (a) with a transmembrane pore such that the one or more polynucleotide binding proteins control the movement of the polynucleotide with respect to the pore; and
   (c) taking one or more measurements as the polynucleotide moves with respect to the pore wherein the measurements are indicative of one or more characteristics of the polynucleotide and thereby characterising the target polynucleotide.

18. A method according to claim 17, wherein the one or more characteristics are selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified.

19. A method according to claim 17, wherein the one or more characteristics of the target polynucleotide are measured by (i) electrical measurement and/or optical measurement or (ii) the electrical measurement which is a current measurement, an impedance measurement, a tunneling measurement or a field effect transistor (FET) measurement.

20. A kit for covalently attaching one or more polynucleotide binding proteins to a target polynucleotide, comprising (a) the one or more polynucleotide binding proteins bound to one or more loading moieties and (b) a ligase.

* * * * *